(12) United States Patent
Maag et al.

(10) Patent No.: US 11,401,246 B2
(45) Date of Patent: Aug. 2, 2022

(54) TRIAZOLE GLYCOLATE OXIDASE INHIBITORS

(71) Applicant: CANTERO THERAPEUTICS, INC., Palo Alto, CA (US)

(72) Inventors: Hans Maag, Kleines Wiesental (DE); Miguel Xavier Fernandes, San Cristobal de la Laguna (ES); Robert Zamboni, Beaconsfield (CA); Elham Akbariromani, Laval (CA); Marc-Andre Beaulieu, L'Assomption (CA); Yves Leblanc, Kirkland (CA); Pallavi Thakur, Montreal (CA)

(73) Assignee: CANTERO THERAPEUTICS, INC., Palo Alto, CA (US)

( * ) Notice: Subject to any disclaimer, the term of this patent is extended or adjusted under 35 U.S.C. 154(b) by 0 days.

(21) Appl. No.: 17/255,600

(22) PCT Filed: Jul. 5, 2019

(86) PCT No.: PCT/US2019/040690
§ 371 (c)(1),
(2) Date: Dec. 23, 2020

(87) PCT Pub. No.: WO2020/010309
PCT Pub. Date: Jan. 9, 2020

(65) Prior Publication Data
US 2021/0403439 A1    Dec. 30, 2021

Related U.S. Application Data

(60) Provisional application No. 62/694,918, filed on Jul. 6, 2018, provisional application No. 62/827,573, filed on Apr. 1, 2019.

(51) Int. Cl.
*C07D 249/04*    (2006.01)

(52) U.S. Cl.
CPC .................. *C07D 249/04* (2013.01)

(58) Field of Classification Search
None
See application file for complete search history.

(56) References Cited

U.S. PATENT DOCUMENTS

| | | |
|---|---|---|
| 7,022,702 B2 | 4/2006 | Zhang et al. |
| 7,288,556 B2 | 10/2007 | Zhang et al. |
| 8,431,574 B2 | 4/2013 | Blake et al. |
| 2008/0207587 A1 | 8/2008 | Kamboj et al. |
| 2014/0030369 A1 | 1/2014 | Yamashita |
| 2016/0262402 A1 | 9/2016 | Thompson et al. |
| 2021/0171474 A1* | 6/2021 | Wang .................. C07D 401/04 |
| 2021/0171503 A1 | 9/2021 | Maag et al. |

FOREIGN PATENT DOCUMENTS

| | | |
|---|---|---|
| JP | S63215680 A | 9/1988 |
| WO | WO-2013104573 A1 | 7/2013 |
| WO | WO-2014064802 A1 | 5/2014 |
| WO | WO-2014113485 A1 | 7/2014 |
| WO | WO-2015185717 A1 | 12/2015 |
| WO | WO-2016110885 A1 | 7/2016 |
| WO | WO-2016148193 A1 | 9/2016 |
| WO | WO-2017100266 A1 | 6/2017 |
| WO | WO-2019133770 A2 | 7/2019 |
| WO | WO-2019133813 A1 | 7/2019 |
| WO | WO-2019165159 A1 | 8/2019 |
| WO | WO-2020010309 A1 | 1/2020 |
| WO | WO-2020257487 A1 | 12/2020 |

OTHER PUBLICATIONS

Bourhis et al., Structure of human glycolate oxidase in complex with the inhibitor 4-carboxy-5-[4-chlorophenyl)-sulfanyl]-1,2,3-thiadiazole, Acta Crystallographica, 2009, F65, pp. 1246-1253.
Buckle et al., Studies on v-triazoles. 7. Antiallergic 9-oxo-1H,9H-benzopyrano[2,3-d]-v-triazoles, Journal of Medicinal chemistry, Feb. 1, 1983, vol. 26, No. 2,pp. 251-254.
Database Registry, Database accession No. 2104463-72-9, Chemical Abstracts Service, Columbus, Ohio, US, Jul. 28, 2017.
Database Registry, Database accession No. 2117454-53-0, Chemical Abstracts Service, Columbus, Ohio, US, Aug. 21, 2017.
Database Registry, Database accession No. 2122068-03-3, Chemical Abstracts Service, Columbus, Ohio, US, Aug. 29, 2017.
European Patent Office, Partial European Search Report for European Patent Application No. 18895918.3, dated May 14, 2021, 11 pages.
International Search Report for PCT/US2018/067863, dated May 9, 2019, 4 pages.
International Search Report for PCT/US2019/040690, dated Jan. 2, 2020, 8 pages.
Leeson et al., The influence of drug-like concepts on decision-making in medicinal chemistry. Nature Reviews Drug Discovery, Nov. 2007, vol. 6, pp. 881-890.
Leonardi et al., Coenzyme A: back in action, Progress in Lipid Research, 2005, vol. 44 pp. 125-153.
Pubchem CID 22219773, created Dec. 5, 2017, 9 pages.
Pubchem CID 59519495, created Aug. 20, 2012, 6 pages.
Rock et al., The murine pantothenate kinase (Pank1) gene encodes two differentially regulated pantothenate kinase isozymes, Gene, 2002, vol. 291, pp. 35-43.
Shultz, Setting expectations in molecular optimizations: Strengths and limitations of commonly used composite parameters, Bioorganic & Medicinal chemistry Letters, 2013, vol. 23, pp. 5980-5991.

(Continued)

*Primary Examiner* — Zinna Northington Davis
(74) *Attorney, Agent, or Firm* — Mintz, Levin, Cohn, Ferris, Glovsky and Popeo, P.C.

(57) ABSTRACT

The present invention provides triazole carboxylic acids and related compounds, as well as pharmaceutically acceptable salts thereof, which are useful as glycolate oxidase inhibitors. Pharmaceutical compositions and methods for treating primary hyperoxaluria, type I (PH) and kidney stones are also described.

23 Claims, 1 Drawing Sheet

(56) References Cited

OTHER PUBLICATIONS

Written Opinion of the International Searching Authority (ISA/US) for PCT/US2018/067863, dated May 9, 2019, 6 pages.
Written Opinion of the International Searching Authority (ISA/US) for PCT/US2019/040690, dated Jan. 2, 2020, 10 pages.
Zhang et al., Feedback Regulation of Murine Pantothenate Kinase 3 by Coenzyme A and Coenzyme A Thioesters, the Journal of biological Chemistry, Sep. 23, 2005, vol. 280, pp. 32594-32601.
Database Registry, Database accession No. RN 678541-52-1, Chemical Abstracts Service, Columbus, Ohio, May 2, 2004.
Database Registry, Database accession No. RN 2091856-74-3, Chemical Abstracts Service, Columbus, Ohio, Apr. 18, 2017.
Zhang et al., Feedback Regulation of Murine Pantothenate Kinase 3 by Coenzyme A and Coenzyme A thioesteers, the Journal of Biological Chemistry, Sep. 23, 2005, vol. 280, No. 38, pp. 32594-32601.
Coe et al., Kidney Stone Disease, The Journal of Clinical Investigation, 2005, vol. 115, No. 10, pp. 2598-2608.
Frishberg et al., Mutations in HA01 encoding glycolate oxidase cause isolated glycolic aciduria, J Med Genet., Jul. 15, 2014, pp. 1-4.
Holmes et al., Contribution of dietary oxalate to urinary oxalate excretion, Kidney International, 2001, vol. 59, pp. 270-276.
Johri et al., An Update and practical guide to Renal Stone Management, Nephron Clinical Practice, Jul. 2, 2010, c115-c171.
Kaufman et al., *Oxalobacter formigenes* May Reduce the Risk of Calcium Oxalate Kidney Stones, Journal of the American Society of Nephrology, 2008, vol. 19, pp. 1197-1203.
Marengo et al., Oxalate in renal stone disease: The terminal metabolite that just won't go away, Nature Clinical Practice Nephrology, Jul. 2008, vol. 4, No. 7, pp. 368-377.
Moe, Kidney stones: pathophysiology and medical management, Lancet, Jan. 28, 2006, vol. 367, pp. 333-344.
Pak et al., Relative effect of urinary calcium and oxalate on saturation of calcium oxalate, Kidney International, 2004, vol. 66, pp. 2032-2037.
Randall et al., Quantitative Structure-Activity Relationships Involving the Inhibition of Glycolic Acid Oxidase by Derivatives of Glycolic and Blyoxylic Acids, Journal of Medicinal Chemistry, 1979, vol. 22, pp. 608-614.
Rooney et al., Inhibitors of Glycolic Acid Oxidase. 4-Substituted 3-Hydroxy-1H-pyrrole-2,5-diione Derivatives,Journal of Medicinal Chemistry, 1983, vol. 26, pp. 700-714.
Sakhaee, Recent advance in the pathophysiology of nephrolithiasis, Kidney International, 2009, vol. 75, pp. 585-595.
Salido et al., Primary hyperoxalurias: disorders of glyoxylae detoxification, Biochimica et Biophysica Acta, 2012, 1822, pp. 1453-1464.
Stenberg et al., Three-dimensional structures of glycolate oxidase with bound active-site inhibitors, Protein Science, 1997, vol. 6, pp. 1009-1015.
Williams et al., Inhibitors of Glycolic Acid Oxidase. 4-Substituted 2,4-Dioxobutanoic Acid Derivative, Journal of Medicinal chemistry, 1983, vol. 26, pp. 1196-1200.

\* cited by examiner

TRIAZOLE GLYCOLATE OXIDASE INHIBITORS

CROSS-REFERENCES TO RELATED APPLICATIONS

The present application is the U.S. National Stage Entry under § 371 of International Application No. PCT/US2019/040690, filed Jul. 5, 2019, which claims priority to U.S. Provisional Application No. 62/694,918, filed on Jul. 6, 2018, and U.S. Provisional Application No. 62/827,573, filed on Apr. 1, 2019, which contents are incorporated herein by reference in their entireties.

BACKGROUND OF THE INVENTION

Kidney stone disease (KSD) has a prevalence of approximately 10% in developed countries with lifetime recurrence rates of up to 50% [Johri, et al. (2010) *Nephron Clin Pract.* 116: c159], KSD patients present with hematuria and renal colic and medical treatment is essentially symptomatic. The administration of drugs to facilitate stone passage is effective for small stones (<5 mm). For bigger stones, extracorporeal sound waves or minimally invasive surgery are used to break the stone into small pieces that can more easily pass the urinary tract [Coe et al. (2005) *J. Clin. Invest.* 115: 2598].

Approximately 75% of kidney stones contain primarily calcium oxalate and elevated levels of urinary oxalate are found in up to 50% of KSD patients. Furthermore, increased levels of urinary oxalate increase the risk of forming kidney stones [Moe (2006) *Lancet* 367: 333; Sakhaee (2009) *Kidney Int.* 75: 585; Kaufman et al. (2008) *J Am Soc Nephrol.* 19: 1197], In mammals, calcium has vital physiological roles in so many processes that its levels are tightly regulated. Oxalate, however, is a metabolic end-product with no known physiological role. Oxalate is a divalent anion that must be eliminated with the urine and tends to precipitate as tissue-damaging insoluble calcium oxalate crystals.

Primary hyperoxalurias (PH) are a group of rare metabolic diseases, with autosomal recessive inheritance, affecting the glyoxylate or the hydroxyproline pathways. All of them have in common an overproduction of oxalate. So far, three forms of primary hyperoxaluria have been identified. They are referred as primary hyperoxaluria types 1, 2, and 3. Primary hyperoxaluria type 1 (PH1) is caused by mutation of liver-specific enzyme alanine-glyoxylate aminotransferase (AGT). Primary hyperoxaluria type 2 (PH2) is caused by mutation of glyoxylate reductase-hydroxypyruvate reductase (GRHPR). Primary hyperoxaluria type 3 (PH3) is caused by mutation of 4-hydroxy-2-oxoglutarate aldolase (HOGA1). PH1 eventually leads to renal failure after several years. PH2 and PH3 have a less severe course. Approximately 80% of PH patients suffer PH1, the most severe PH type. Considering its statistical predominance, most studies on PH essentially refer to PH1 [Salido et al. (2012) *Biochim Biophys Acta.* 1822: 1453].

Since calcium levels are so tightly regulated in the organism, changing them in urine is extremely difficult, and it may also produce undesired effects in vital physiological processes. Minor increases in urinary oxalate can produce large effect on calcium oxalate crystal formation, and elevated levels of urinary oxalate are a major risk factor for the formation of calcium oxalate kidney stones [Pak, et al. (2004) *Kidney Int.* 66: 2032], Consequently, a small decrease in oxalate concentration could lower the calcium oxalate level below saturation, and thus prevent calcium oxalate stone formation. Irrespective of the urinary oxalate levels in individuals with kidney stone disease, primary hyperoxaluria, or secondary hyperoxaluria, lowering UOx levels will decrease the contribution of oxalate to calcium oxalate formation, and thus lower the probability of stone formation and/or alleviate the severity of excessive calcium oxalate deposition related conditions [Marengo et al. (2008) *Nat Clin Pract Nephrol.* 4: 368].

The development of an effective drug that reduces urinary oxalate levels can be a valuable therapeutic option in the prophylaxis and treatment of conditions related to calcium oxalate. Common approaches for treatment of urolithiasis due to calcium oxalate include surgical removal of stones, dietary changes increase fluid intake and to restrict oxalate intake, urine alkalization, diuretics, and crystallization inhibitors such as citrate, bicarbonate, and magnesium [Moe, supra]. However, none of these therapeutic approaches tackles the origin of the conditions. No drug which specifically inhibits the endogenous biosynthetic formation of oxalate is commercially available for the prophylaxis and treatment of calcium oxalate deposition related conditions.

In humans, dietary oxalate contributes only 10-50% to the amount of excreted urinary oxalate [Holmes, et al. (2001) *Kidney Int.* 59: 270], Most urinary oxalate is derived from the endogenous metabolism, mainly in liver. In humans, the major precursor of oxalate is glyoxylate. Therefore, approaches to reduce the production of oxalate must block the conversion of glyoxylate into oxalate, or block the production of glyoxylate from its precursors. In humans, the major precursor of glyoxylate is glycolate in a reaction catalyzed by the peroxisomal liver enzyme glycolate oxidase (GO), also termed hydroxyacid oxidase 1. Pharmacological inhibition of GO activity with small molecules will diminish endogenous oxalate production and lead to a reduction of calcium oxalate levels in the urine, thus providing a specific approach for prophylaxis and treatment of calcium oxalate deposition and related conditions. There is evidence that GO is a safe therapeutic target in humans. A report describes a finding where a defective splice variant of human GO in an individual simply causes isolated asymptomatic glycolic aciduria with no apparent ill effects [Frishberg, et al. (2014) *J Med Genet.* 51: 526].

BRIEF SUMMARY OF THE INVENTION

Provided herein are compounds according to Formula I,

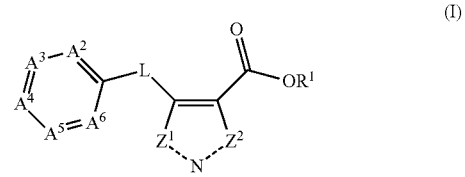

and pharmaceutically acceptable salts thereof, wherein:
L is selected from O and S;
$A^2$ is selected from $CR^2$ and N;
$A^3$ is selected from $CR^3$ and N;
$A^4$ is selected from $CR^4$ and N;
$A^5$ and $A^6$ are independently selected from CH and N;
the dashed line connected to $Z^1$ is a double bond, $Z^1$ is N, the dashed line connected to $Z^2$ is a single bond, and $Z^2$ is $NR^5$; or the dashed line connected to $Z^1$ is a single bond, $Z^1$ is $NR^5$, the dashed line connected to $Z^2$ is a double bond, and $Z^2$ is N;

$R^1$ is selected from H, unsubstituted $C_{1-6}$ alkyl, substituted $C_{1-6}$ alkyl, —($C_{1-6}$ alkylene)-OC(O)—($C_{1-6}$ alkyl), and —($C_{1-6}$ alkylene)-OC(O)—($C_{1-6}$ alkoxy);

$R^2$ is selected from H and halogen;

$R^3$ and $R^4$ are independently selected from H, halogen, $C_{1-12}$ alkyl, $C_{1-12}$ alkoxy, $C_{6-12}$ aryl, $C_{3-8}$ cycloalkyl, 3- to 12-membered heterocyclyl, and 5- to 12-membered heteroaryl;

$R^3$ is optionally substituted with one or more $R^{3a}$;

$R^4$ is optionally substituted with one or more $R^{4a}$; and each $R^{3a}$ and $R^{4a}$ is independently selected from $C_{1-12}$ alkyl, $C_{1-12}$ alkoxy, $C_{1-12}$ haloalkyl, $C_{1-12}$ haloalkoxy, halogen, —OH, —$CO_2H$, —$SO_3$, —CN, —$NO_2$, —$N_3$, $C_{2-12}$ alkenyl, $C_{2-12}$ alkynyl, $C_{3-8}$ cycloalkyl, $C_{3-8}$ halocycloalkyl, ($C_{6-12}$ aryl)-M-, 3- to 12-membered heterocyclyl, 5- to 12-membered heteroaryl, —$N(R^a)_2$, —$C(O)N(R^a)_2$, —$OC(O)N(R^a)_2$, —$S(O)_2N(R^a)_2$, —$NR^aC(O)R^b$, —$C(O)R^b$, and —$OC(O)R^b$;

$R^5$ is selected from H, unsubstituted $C_{1-6}$ alkyl, substituted $C_{1-6}$ alkyl, $C_{2-7}$ acyl, —($C_{1-6}$ alkylene)-OC(O)—($C_{1-6}$ alkyl), and —($C_{1-6}$ alkylene)-OC(O)—($C_{1-6}$ alkoxy);

each M is independently selected from a covalent bond, $NR^a$, O, S, $C_{1-6}$ alkylene, and 2- to 6-membered heteroalkylene;

each $R^a$ is independently selected from H and $C_{1-6}$ alkyl; and each $R^b$ is independently selected from $C_{1-6}$ alkyl and $C_{1-6}$ alkoxy;

provided that if L is O, $A^2$ is $CR^2$, $A^3$ is $CR^3$, $A^4$ is $CR^4$, and $A^5$ and $A^6$ are CH, then:
at least one of $R^2$, $R^3$, and $R^4$ is other than H,
$R^2$ is other than chloro or fluoro when $R^3$ and $R^4$ are H,
$R^3$ is other than chloro, fluoro, methyl, methoxy, trifluoromethyl, or —OH when $R^2$ and $R^4$ are H,
$R^4$ is other than methyl, ethyl, isopropyl, tert-butyl, methoxy, ethoxy, acetoxy, fluoro, or hydroxy when $R^2$ and $R^3$ are H, and
$R^4$ is other than fluoro when $R^2$ is fluoro and $R^3$ is H;

provided that if L is O, $A^2$ is $CR^2$, $A^3$ is N, $A^4$ is $CR^4$, and $A^5$ and $A^6$ are CH, then at least one of $R^2$ and $R^4$ is other than H; and provided that if L is S, $A^2$ is $CR^2$, $A^3$ is $CR^3$, $A^4$ is $CR^4$, and $A^5$ and $A^6$ are CH, then:
$R^4$ is other than methoxy, 4-bromophenyl, or 4-fluorophenyl when $R^2$ and $R^3$ are H, and
$R^3$ is other than 4-bromophenyl or 4-fluorophenyl when $R^2$ and $R^4$ are H.

Also provided herein are pharmaceutical compositions containing one or more triazole compounds as described herein (e.g., a compound of Formula I, Formula Ia, Formula Ib, Formula Ic, or Formula II) and a pharmaceutically acceptable excipient.

Also provided are methods for treating primary hyperoxaluria, type I (PH1). The methods include administering to a subject in need thereof a therapeutically effective amount of a compound described herein (e.g., a compound of Formula I, Formula Ia, Formula Ib, Formula Ic, or Formula II).

Also provided are methods for treating kidney stones. The methods include administering to a subject in need thereof a therapeutically effective amount of a compound described herein (e.g., a compound of Formula I, Formula Ia, Formula Ib, Formula Ic, or Formula II).

DETAILED DESCRIPTION OF THE INVENTION

I. General

Figure 1:
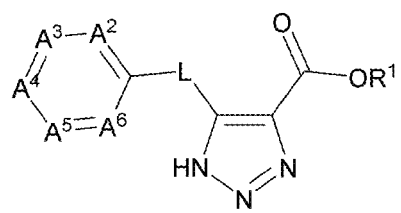
FIG. 1 shows the structure of exemplary glycolate oxidase inhibitors provided herein.

The present invention provides effective therapeutic approaches for inhibiting biosynthetic formation of oxalate and for treating PH1 and other conditions related to deposition of calcium oxalate. New triazole compounds which are useful as glycolate oxidase inhibitors are provided, as well as methods for making and using the triazole compounds.

II. Definitions

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. "Substituted alkyl" groups can be substituted with one or more groups selected from halo, hydroxy, amino, alkylamino, amido, acyl, nitro, cyano, and alkoxy.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the term "alkoxy," by itself or as part of another substituent, refers to a moiety having the formula —OR, wherein R is an alkyl group as defined herein. Examples of alkoxy groups include, but are not limited to, methoxy, ethoxy, and isopropyloxy.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. "Substituted cycloalkyl" groups can be substituted with one or more groups selected from halo, hydroxy, amino, alkylamino, amido, acyl, nitro, cyano, and alkoxy. The term "lower cycloalkyl" refers to a cycloalkyl radical having from three to seven carbons including, for example, cyclopropyl, cyclobutyl, cyclopentyl, cyclohexyl, and cycloheptyl.

As used herein, the term "heteroalkyl," by itself or as part of another substituent, refers to an alkyl group of any suitable length and having from 1 to 3 heteroatoms such as N, O and S. For example, heteroalkyl can include ethers, thioethers and alkyl-amines. Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen of the alkyl group to form a hydroxy, thio, or amino group. Alternatively, the heteroatom portion can be the connecting atom, or be inserted between two carbon atoms.

As used herein, the term "heteroalkylene" refers to a heteroalkyl group, as defined above, linking at least two other groups (i.e., a divalent heteroalkyl radical). The two moieties linked to the heteroalkylene group can be linked to the same atom or different atoms of the heteroalkylene group.

As used herein the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclic groups can be saturated (e.g., azetidinyl, pyrrolidinyl, piperidinyl, morpholine, oxetanyl, tetrahydrofuranyl, or tetrahydropyranyl) or unsaturated (e.g., 2,3-dihydrofuranyl, 2,5-dihydrofuranyl, 3,4-dihydropyranyl, 3,6-dihydropyranyl, or 1,4-dihydropyridinyl). Heterocyclyl groups can be unsubstituted or substituted. "Substituted heterocyclyl" groups can be substituted with one or more groups selected from halo, hydroxy, amino, oxo (═O), alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "aryl," by itself or as part of another substituent, refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. "Substituted aryl" groups can be substituted with one or more groups selected from halo, hydroxy, amino, alkylamino, amido, acyl, nitro, cyano, and alkoxy.

As used herein, the term "arylalkyl" refers to an aryl group that is bonded to a compound via an alkylene group as described herein. Examples of arylalkyl groups include, but are not limited to, benzyl and phenethyl.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. "Substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the terms "halo" and "halogen," by themselves or as part of another substituent, refer to a fluorine, chlorine, bromine, or iodine atom.

As used herein, the term "cyano," by itself or as part of another substituent, refers to a carbon atom triple-bonded to a nitrogen atom (i.e., the moiety —C≡N).

As used herein, the term "carbonyl," by itself or as part of another substituent, refers to —C(O)—, i.e., a carbon atom double-bonded to oxygen and bound to two other groups in the moiety having the carbonyl.

As used herein, the term "amino," by itself or as part of another substituent, refers to a moiety —NR$_3$, wherein each R group is H or alkyl. An amino moiety can be ionized to form the corresponding ammonium cation.

As used herein, the term "hydroxy," by itself or as part of another substituent, refers to the moiety —OH.

As used herein, the term "carboxy," by itself or as part of another substituent, refers to the moiety —C(O)OH. A carboxy moiety can be ionized to form the corresponding carboxylate anion.

As used herein, the term "amido," by itself or as part of another substituent, refers to a moiety —NRC(O)R or —C(O)NR$_2$, wherein each R group is H or alkyl.

As used herein, the term "nitro," by itself or as part of another substituent, refers to the moiety —NO$_2$.

As used herein, the term "oxo," by itself or as part of another substituent, refers to an oxygen atom that is double-bonded to a compound (i.e., O═).

As used herein, the term "salt" refers to acid or base salts of the compounds of the invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid, fumaric acid, and the like) salts, quaternary ammonium (methyl iodide, ethyl iodide, and the like) salts. It is understood that the pharmaceutically acceptable salts are non-toxic.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

As used herein, the terms "treat," "treatment," and "treating" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; reduction in the rate of symptom progression; decreasing the frequency or duration of the symptom or condition. In some situations, treating can including preventing the onset of the injury, pathology, condition, or symptom. The treatment or amelioration of symptoms can be based on any objective or subjective parameter; including, e.g., the result of a physical examination.

As used herein, the terms "primary hyperoxaluria, type I" and "PH1" are interchangeable and refer to a condition caused by the deficiency of alanine:glyoxylate aminotransferase (AGT), a liver enzyme. This deficiency causes impaired glyoxylate metabolism in the liver and an ultimate increase in oxalate synthesis, contributing to the formation of calcium oxalate kidney stones.

As used herein, the term "kidney stone" refers to a small, solid particle that occur in the kidneys, renal pelvis, ureter, urinary bladder, and/or urethra. Commonly, kidney stones contain or consist of calcium salt particles including, but not limited to, calcium oxalate particles and calcium phosphate particles (e.g., apatite particles or brushite particles). Kidney stones can also contain or consist of uric acid, struvite (i.e., $NH_4MgPO_4 \cdot 6H_2O$ particles), and cystine (i.e., particles containing oxidized cysteine disulfide dimer). Kidney stones typically range in size from less than a millimeter in their largest dimension to 5 or more centimeters in their largest dimension. Kidney stones often form in the kidney or renal pelvis and, when they are small enough (e.g., less than 5 mm), they can pass through the ureter, bladder, and urethra to be eliminated from the body via urination. Kidney stones often cause severe pain in the side and back, below the ribs, and severe pain in the lower abdomen and groin. Other symptoms of kidney stones include, but are not limited to, pain upon urination, abnormally colored urine (e.g., pink, red, or brown), cloudy urine, foul-smelling urine, nausea and vomiting, a persistent need to urinate, low urine volume, fever, and chills. The presence of kidney stones in the urinary system can be confirmed using imaging techniques such as abdominal X-ray, CT scan, and ultrasound.

The terms "glycolate oxidase" and "GO" are used interchangeably to refer to the liver peroxisomal enzyme glycolate oxidase 1 (GO1), also known as hydroxyacid oxidase 1 (HAO1). The human enzyme is cataloged under NCBI Accession No. NP_060015.1 and UniProtKB Reference No. Q9UJM8. The mouse enzyme is cataloged under GenBank Accession No. EDL28373.1 and UniProtKB Reference No. Q9WU19. The enzyme catalyzes the conversion of glycolic acid to glyoxylic acid, an oxalic acid precursor.

As used herein, the term "administering" refers to oral, topical, parenteral, intravenous, intraperitoneal, intramuscular, intralesional, intranasal, subcutaneous, or intrathecal administration to a subject, as well administration as a suppository or the implantation of a slow-release device, e.g., a mini-osmotic pump, in the subject.

As used herein, the term "subject" refers to a person or other animal to whom a compound or composition as described herein is administered. In some embodiments, the subject is human. In some embodiments, the subject is a human having a mutation in the AGXT gene encoding alanine-glyoxylate amino transferase (AGT).

As used herein, the terms "effective amount" and "therapeutically effective amount" refer to a dose of a compound such as a glycolate oxidation inhibitor that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); Goodman & Gilman's *The Pharmacological Basis of Therapeutics*, 11th Edition, 2006, Brunton, Ed., McGraw-Hill; and Remington: *The Science and Practice of Pharmacy*, 21st Edition, 2005, Hendrickson, Ed., Lippincott, Williams & Wilkins).

As used herein, the terms "about" and "around" indicate a close range around a numerical value when used to modify that specific value. If "X" were the value, for example, "about X" or "around X" would indicate a value from 0.9X to 1.1X, e.g., a value from 0.95X to 1.05X, or a value from 0.98X to 1.02X, or a value from 0.99X to 1.01X. Any reference to "about X" or "around X" specifically indicates at least the values X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.1X, and values within this range.

III. Glycolate Oxidase Inhibitors

Provided herein are compounds according to Formula I:

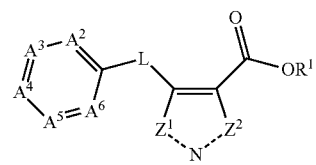

(I)

and pharmaceutically acceptable salts thereof, wherein:
L is selected from O and S;
$A^2$ is selected from $CR^2$ and N;
$A^3$ is selected from $CR^3$ and N;
$A^4$ is selected from $CR^4$ and N;
$A^5$ and $A^6$ are independently selected from CH and N;
the dashed line connected to $Z^1$ is a double bond, $Z^1$ is N, the dashed line connected to $Z^2$ is a single bond, and $Z^2$ is $NR^5$; or
the dashed line connected to $Z^1$ is a single bond, $Z^1$ is $NR^5$, the dashed line connected to $Z^2$ is a double bond, and $Z^2$ is N;
$R^1$ is selected from H, unsubstituted $C_{1-6}$ alkyl, substituted $C_{1-6}$ alkyl, —($C_{1-6}$ alkylene)-OC(O)—($C_{1-6}$ alkyl), and —($C_{1-6}$ alkylene)-OC(O)—($C_{1-6}$ alkoxy);
$R^2$ is selected from H and halogen;
$R^3$ and $R^4$ are independently selected from H, halogen, $C_{1-12}$ alkyl, $C_{1-12}$ alkoxy, $C_{6-12}$ aryl, $C_{3-8}$ cycloalkyl, 3- to 12-membered heterocyclyl, and 5- to 12-membered heteroaryl;
$R^3$ is optionally substituted with one or more $R^{3a}$;
$R^4$ is optionally substituted with one or more $R^{4a}$; and
each $R^{3a}$ and $R^{4a}$ is independently selected from $C_{1-12}$ alkyl, $C_{1-12}$ alkoxy, $C_{1-12}$ haloalkyl, $C_{1-12}$ haloalkoxy, halogen, —OH, —$CO_2H$, —$SO_3$, —CN, —$NO_2$, —$N_3$, $C_{2-12}$ alkenyl, $C_{2-12}$ alkynyl, $C_{3-8}$ cycloalkyl, $C_{3-8}$ halocycloalkyl, ($C_{6-12}$ aryl)-M-, 3- to 12-membered heterocyclyl, 5- to 12-membered heteroaryl, —$N(R^a)_2$, —$C(O)N(R^a)_2$, —$OC(O)N(R^a)_2$, —$S(O)_2N(R^a)_2$, —$NR^aC(O)R^b$, —$C(O)R^b$, and —$OC(O)R^b$;

$R^5$ is selected from H, unsubstituted $C_{1-6}$ alkyl, substituted $C_{1-6}$ alkyl, $C_{2-7}$ acyl, —($C_{1-6}$ alkylene)-OC(O)—($C_{1-6}$ alkyl), and —($C_{1-6}$ alkylene)-OC(O)—($C_{1-6}$ alkoxy);

each M is independently selected from a covalent bond, $NR^a$, O, S, $C_{1-6}$ alkylene, and 2- to 6-membered heteroalkylene;

each $R^a$ is independently selected from H and $C_{1-6}$ alkyl; and each $R^b$ is independently selected from $C_{1-6}$ alkyl and $C_{1-6}$ alkoxy;

provided that if L is O, $A^2$ is $CR^2$, $A^3$ is $CR^3$, $A^4$ is $CR^4$, and $A^5$ and $A^6$ are CH, then:
at least one of $R^2$, $R^3$, and $R^4$ is other than H,
$R^2$ is other than chloro or fluoro when $R^3$ and $R^4$ are H,
$R^3$ is other than chloro, fluoro, methyl, methoxy, trifluoromethyl, or —OH when $R^2$ and $R^4$ are H,
$R^4$ is other than methyl, ethyl, isopropyl, tert-butyl, methoxy, ethoxy, acetoxy, fluoro, or hydroxy when $R^2$ and $R^3$ are H, and
$R^4$ is other than fluoro when $R^2$ is fluoro and $R^3$ is H;

provided that if L is O, $A^2$ is $CR^2$, $A^3$ is N, $A^4$ is $CR^4$, and $A^5$ and $A^6$ are CH, then at least one of $R^2$ and $R^4$ is other than H; and provided that if L is S, $A^2$ is $CR^2$, $A^3$ is $CR^3$, $A^4$ is $CR^4$, and $A^5$ and $A^6$ are CH, then:
$R^4$ is other than methoxy, 4-bromophenyl, or 4-fluorophenyl when $R^2$ and $R^3$ are H, and
$R^3$ is other than 4-bromophenyl or 4-fluorophenyl when $R^2$ and $R^4$ are H.

In some embodiments, compounds having a structure according to Formula Ia, and pharmaceutically acceptable salts thereof, are provided:

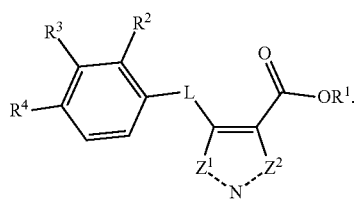

(Ia)

In some embodiments, compounds having a structure according to Formula Ib, and pharmaceutically acceptable salts thereof, are provided:

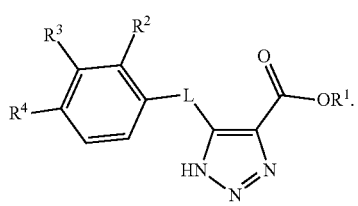

(Ib)

In some embodiments, compounds having a structure according to Formula Ic, and pharmaceutically acceptable salts thereof, are provided:

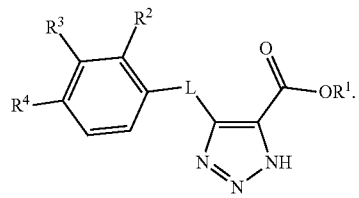

(Ic)

One of skill in the art will appreciate that compounds according to Formula Ia may exist in tautomeric forms according to Formula Ib and Formula Ic. As used herein, the term "tautomer" refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). For the purposes of the present disclosure, the depiction of any particular triazole is intended to encompass both tautomeric forms of the triazole, generalized by the $Z^1$—N—$Z^2$ grouping in Formula I.

In some embodiments, L is O in compounds according to Formula I and Formula Ia. In some embodiments, L is S in compounds according to Formula I and Formula Ia.

In some embodiments, $R^2$ and $R^3$ are independently selected from H and halogen.

In some embodiments, $R^2$ is halogen and $R^3$ is H. In some such embodiments, $R^4$ is H.

In some embodiments, $R^2$ is H and $R^3$ is halogen. In some such embodiments, $R^4$ is H.

In some embodiments, $R^2$ is H and $R^3$ and $R^4$ are halogen.

In some embodiments, $R^4$ is substituted with one or more $R^{4a}$ selected from $C_{1-12}$ alkyl, $C_{1-12}$ alkoxy, $C_{1-12}$ haloalkyl, $C_{1-12}$ haloalkoxy, halogen, —OH, —$CO_2H$, —$SO_3$, —CN, —$NO_2$, —$N_3$, $C_{2-12}$ alkenyl, $C_{2-12}$ alkynyl, $C_{3-8}$ cycloalkyl, $C_{3-8}$ halocycloalkyl, $C_{6-12}$ aryl, $C_{7-18}$ arylalkyl, 3- to 12-membered heterocyclyl, 5- to 12-membered heteroaryl, —$N(R^a)_2$, —$C(O)N(R^a)_2$, —$OC(O)N(R^a)_2$, —$S(O)_2N(R^a)_2$, —$NR^aC(O)R^b$, —$C(O)R^b$, and —$OC(O)R^b$. In some embodiments two $R^{4a}$ groups on the same carbon atom of $R^4$ are taken together to form a cycloalkyl group (i.e., a spirocycloalkyl group such a spirocyclopropyl) or a halocycloalkyl group (i.e., a spirohalocycloalkyl group such as 1,1-difluorospirocycloprop-2-yl).

In some embodiments, $R^2$ and $R^3$ are H in compounds of Formula Ia. In some such embodiments, $R^4$ is selected from halogen, $C_{1-12}$ alkyl, $C_{6-12}$ aryl, 3- to 12-membered heterocyclyl, and 5- to 12-membered heteroaryl, each of which is optionally substituted with one or more $R^{4a}$. In some embodiments, $R^4$ in compounds of Formula I and Formula Ia is chloro, bromo, or iodo. In some embodiments, $R^4$ in Compounds of Formula I and Formula Ia is 3- to 12-membered heterocyclyl, which can be unsubstituted or substituted with $R^{4a}$. For example, $R^4$ can be unsubstituted or substituted aziridinyl, unsubstituted or substituted azetidinyl, unsubstituted or substituted pyrrolidinyl, unsubstituted or substituted piperidinyl, unsubstituted or substituted azepanyl, unsubstituted or substituted imidazolidinyl, unsubstituted or substituted piperazinyl, unsubstituted or substituted tetrahydrofuranyl, unsubstituted or substituted tetrahydropyranyl, unsubstituted or substituted oxazolidinyl, isoxazolidinyl, unsubstituted or substituted thiazolidinyl, or unsubstituted or substituted morpholine. In some embodiments, $R^4$ is selected from morpholino (i.e., morpholin-4-yl), morpholin-2-yl, morpholin-3-yl, piperazin-1-yl, piperazine-2-yl, and piperazine-3-yl. Heterocyclyl groups can be substituted with one or more $R^{4a}$ groups. A nitrogen atom in a piperazinyl group can be substituted with acetyl, as in the case of 4-acetylpiperazin-1-yl for example.

In some embodiments, $R^4$ in compounds of Formula I and Formula Ia is 5- to 12-membered heteroaryl, which is optionally substituted with one or more $R^{4a}$. $R^4$ can be, for example unsubstituted or substituted pyrrolyl, unsubstituted or substituted pyridinyl, unsubstituted or substituted imidazolyl, unsubstituted or substituted pyrazolyl, unsubstituted or substituted triazolyl, unsubstituted or substituted tetrazolyl, unsubstituted or substituted pyrazinyl, unsubstituted or substituted triazinyl, unsubstituted or substituted indolyl, unsubstituted or substituted isoindolyl, unsubstituted or substituted quinolinyl, unsubstituted or substituted thiophenyl, unsubstituted or substituted furanyl, unsubstituted or substituted thiazolyl, unsubstituted or substituted oxazolyl, unsubstituted or substituted pyrimidinyl. In some embodiments, $R^4$ is selected from pyrazolyl, pyridinyl, thiophenyl, furanyl, pyrazinyl, thiazolyl, oxazolyl, and imidazopyridinyl, each of which is optionally substituted with one or more $R^{4a}$. In some such embodiments, $R^{4a}$ is selected from halogen, $C_{1-12}$ alkyl, and $C_{3-8}$ cycloalkyl. $R^{4a}$ can be, for example, fluoro, chloro, bromo, methyl, ethyl, n-propyl, isopropyl, n-butyl, isobutyl, sec-butyl, tert-butyl, n-pentyl, branched pentyl, n-hexyl, branched hexyl, n-heptyl, branched heptyl, n-octyl, or branched octyl cyclopropyl, cyclobutyl, cyclopentyl, cyclohexyl, or cyclooctyl.

In some embodiments, $R^4$ in compounds of Formula I and Formula Ia is selected from phenyl and biphenyl, each of which is optionally substituted with one or more $R^{4a}$. In some such embodiments, $R^{4a}$ is selected from $C_{1-12}$ alkyl, $C_{1-12}$ alkoxy, $C_{1-12}$ haloalkyl, $C_{1-12}$ haloalkoxy, halogen, —CN, 5- to 12-membered heteroaryl, and —C(O)N($R^a$)$_2$.

In some embodiments, $R^4$ is unsubstituted phenyl in compounds of Formula Ia. In some embodiments, $R^4$ is phenyl substituted with —CN or halogen. $R^{4a}$ in such instances can be, for example, —CN, bromo, or chloro. In some embodiments, $R^4$ is phenyl substituted with $C_{1-12}$ alkyl, $C_{1-12}$ haloalkyl, or $C_{1-12}$ haloalkoxy. $R^{4a}$ in such instances can be, for example, methyl, ethyl, n-propyl, isopropyl, n-butyl, isobutyl, sec-butyl, tert-butyl, n-pentyl, branched pentyl, n-hexyl, branched hexyl, n-heptyl, branched heptyl, n-octyl, branched octyl, n-nonyl, branched nonyl, n-decyl, branched decyl, n-undecyl, branched undecyl, n-dodecyl, or branched dodecyl. $R^{4a}$ can be chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, 1,1,1,3,3,3-hexafluoropropyl, or the like. $R^{4a}$ can be chloromethoxy, dichloromethoxy, trichloromethoxy, fluoromethoxy, difluoromethoxy, trifluoromethoxy, 2,2,2-trichloroethoxy, 2,2,2-trifluoroethoxy, pentachloroethoxy, pentafluoroethoxy, 1,1,3,3,3-hexachloropropoxy, 1,1,1,3,3,3-hexafluoropropoxy, or the like. The $R^{4a}$ group can be bonded to the 2-position, the 3-position, or the 4-position of the $R^4$ phenyl group.

In some embodiments, $R^4$ is phenyl substituted with —C(O)N($R^a$)$_2$. $R^{4a}$ in such instances can be, for example, carbamoyl (i.e., —C(O)NH$_2$) bonded to the 2-position, 3-position, or 4-position of the $R^4$ phenyl group. In some embodiments, $R^4$ is phenyl substituted with 5- to 12-membered heteroaryl. $R^{4a}$ in such instances can be, for example, isoxazolyl, oxazolyl, imidazolyl, pyrazolyl, pyridinyl, oxazinyl, pyrimidinyl, pyrazinyl, pyridazinyl, each of which can be bonded to the 2-position, 3-position, or 4-position of the $R^4$ phenyl group. In some embodiments, $R^{4a}$ is 4-(pyridinyl), e.g., 4-(pyridin-4-yl).

In some embodiments, $R^4$ is biphenyl substituted with $C_{1-12}$ alkyl, $C_{1-12}$ haloalkyl, or $C_{1-12}$ haloalkoxy. $R^4$ can be, for example, [1,1'-biphenyl]-4-yl substituted with $R^{4a}$ at the 2'-position, 3'-position, or 4'-position. $R^{4a}$ in such instances can be, for example, chloromethoxy, dichloromethoxy, trichloromethoxy, fluoromethoxy, difluoromethoxy, trifluoromethoxy, 2,2,2-trichloroethoxy, 2,2,2-trifluoroethoxy, pentachloroethoxy, pentafluoroethoxy, 1,1,1,3,3,3-hexachloropropoxy, 1,1,1,3,3,3-hexafluoropropoxy, or the like.

Compounds of Formula I or Formula Ia where L is O can include any of the $R^4/R^{4a}$ combinations set forth above. Likewise, compounds of Formula I or Formula Ia where L is S can include any of the $R^4/R^{4a}$ combinations set forth above. In some embodiments, $R^4$ in compounds of Formula I and Formula Ia is halogen and L is O. In some embodiments, $R^4$ in compounds of Formula I and Formula Ia is halogen and L is S. In some embodiments, $R^4$ in Compounds of Formula I and Formula Ia is 3- to 12-membered heterocyclyl and L is O. In some embodiments, $R^4$ in Compounds of Formula I and Formula Ia is 3- to 12-membered heterocyclyl and L is S. In some embodiments, $R^4$ in Compounds of Formula I and Formula Ia is 5- to 12-membered heteroaryl and L is O. In some embodiments, $R^4$ in Compounds of Formula I and Formula Ia is 5- to 12-membered heteroaryl and L is S.

In some embodiments, $R^4$ is unsubstituted phenyl and L is O in compounds of Formula Ia. In some embodiments, $R^4$ is unsubstituted phenyl and L is S in compounds of Formula Ia. In some embodiments, $R^4$ is phenyl substituted with —CN or halogen and L is O. In some embodiments, $R^4$ is phenyl substituted with —CN or halogen and L is S. In some embodiments, $R^4$ is phenyl substituted with $C_{1-12}$ alkyl, $C_{1-12}$ haloalkyl, or $C_{1-12}$ haloalkoxy and L is O. In some embodiments, $R^4$ is phenyl substituted with $C_{1-12}$ alkyl, $C_{1-12}$ haloalkyl, or $C_{1-12}$ haloalkoxy and L is S. In some embodiments, $R^4$ is phenyl substituted with —C(O)N($R^a$)$_2$ and L is O. In some embodiments, $R^4$ is phenyl substituted with —C(O)N($R^a$)$_2$ and L is S. In some embodiments, $R^4$ is phenyl substituted with 5- to 12-membered heteroaryl and L is O. In some embodiments, $R^4$ is phenyl substituted with 5- to 12-membered heteroaryl and L is S. In some embodiments, $R^4$ is biphenyl substituted with $C_{1-12}$ alkyl, $C_{1-12}$ haloalkyl, or $C_{1-12}$ haloalkoxy and L is O. In some embodiments, $R^4$ is biphenyl substituted with $C_{1-12}$ alkyl, $C_{1-12}$ haloalkyl, or $C_{1-12}$ haloalkoxy and L is S.

The ring containing $A^2$, $A^3$, $A^4$, $A^5$, and $A^6$ in compounds of Formula I can be any one of a number of nitrogen-containing heterocycles including, for example, pyridinyl, pyridazinyl, pyrimidinyl, pyrazinyl, 1,2,3-triazinyl, 1,2,4-triazinyl, and 1,3,5-triazinyl. In some embodiments, $A^3$ is N. In some such embodiments, $A^2$ is $CR^2$, $A^4$ is $CR^4$, $A^5$ is CH, and $A^6$ is CH, i.e., the ring containing $A^2$, $A^3$, $A^4$, $A^5$, and $A^6$ is a pyridin-3-yl group. In some embodiments, $R^2$ is H. In some embodiments, the ring containing $A^2$, $A^3$, $A^4$, $A^5$, and $A^6$ is a 4-substituted pyridin-3-yl group, i.e., $A^3$ is N; $A^2$, $A^5$, and $A^6$ are CH; and $A^4$ is $CR^4$. In some such embodiments, $R^4$ is selected from halogen, unsubstituted or substituted $C_{1-12}$ alkyl, unsubstituted or substituted $C_{6-12}$ aryl, and unsubstituted or substituted $C_{3-8}$ cycloalkyl. In some embodiments, $R^4$ is fluoro, chloro, bromo, unsubstituted phenyl, and $R^{4a}$-substituted phenyl. $R^{4a}$ can be, for example, $C_{1-12}$ alkyl, $C_{1-12}$ alkoxy, $C_{1-12}$ haloalkyl, or $C_{1-12}$ haloalkoxy. In some embodiments, $R^4$ is phenyl and $R^{4a}$ is chloromethyl, dichloromethyl, trichloromethyl, fluoromethyl, difluoromethyl, trifluoromethyl, chloromethoxy, dichloromethoxy, trichloromethoxy, fluoromethoxy, difluoromethoxy, or trifluoromethoxy. The $R^{4a}$ group can be bonded to the 2-position, the 3-position, or the 4-position of the $R^4$ phenyl group. In some embodiments, the ring containing $A^2$, $A^3$, $A^4$, $A^5$, and $A^6$ in compounds of Formula I is a nitrogen-containing heterocycle (e.g., an optionally substituted pyridinyl-3-yl moiety) as described above, wherein L is O. In some embodiments, the ring containing $A^2$, $A^3$, $A^4$, $A^5$, and $A^6$ in compounds of Formula I is a nitrogen-containing heterocycle as described above, wherein L is S.

Compounds of Formula I and Formula Ia include acids, wherein $R^1$ is H, as well as esters. In some embodiments, the ester is a compound wherein $R^1$ is unsubstituted $C_{1-6}$ alkyl, substituted $C_{1-6}$ alkyl. $R^1$ can be, for example, methyl, ethyl, n-propyl, isopropyl, n-butyl, isobutyl, sec-butyl, tert-butyl, n-pentyl, branched pentyl, n-hexyl, branched hexyl, benzyl, phenethyl, or the like. In some embodiments, $R^1$ is unsubstituted methyl or methyl substituted with a heterocyclic moiety such as a 5-methyl-2-oxo-1,3-dioxol-4-yl group. In some embodiments, the ester is an (acyloxy)alkyl ester wherein $R^1$ is —($C_{1-6}$ alkylene)-OC(O)—($C_{1-6}$ alkyl). In some embodiments, the ester is an [(alkoxycarbonyl)oxy]alkyl ester wherein $R^1$ is —($C_{1-6}$ alkylene)-OC(O)—($C_{1-6}$ alkoxy) (e.g., ((isopropoxycarbonyl)oxy)methyl). Acids and esters according to Formula I can have any combination of $A^2$, $A^3$, $A^4$, $A^5$, $A^6$, L, $R^1$, $R^2$, $R^3$, and $R^4$ as set forth above. In some embodiments an ester, wherein $R^1$ is unsubstituted $C_{1-6}$ alkyl, substituted $C_{1-6}$ alkyl, —($C_{1-6}$ alkylene)-OC(O)—($C_{1-6}$ alkyl), or —($C_{1-6}$ alkylene)-OC(O)—($C_{1-6}$ alkoxy), can act as prodrug. In such instances, an active compound in which $R^1$ is H is generated upon ester hydrolysis following administration to a subject. $R^1$ and $R^5$ can include further prodrug moieties in the compounds of the present disclosure including, but not limited to, cleavable carbonate, carbamate, anhydride, and disulfide moieties.

The compounds provided herein may be further substituted. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\alpha$; —$(CH_2)_{0-4}OR^\alpha$; —$O(CH_2)_{0-4}R^\alpha$, —$O$—$(CH_2)_{0-4}C(O)OR^\alpha$; —$(CH_2)_{0-4}CH(OR^\alpha)_2$; —$(CH_2)_{0-4}SR^\alpha$; —$(CH_2)_{0-4}$phenyl, which phenyl may be substituted with $R^\alpha$; —$(CH_2)_{0-4}O(CH_2)_{0-1}$phenyl, which phenyl may be substituted with $R^\alpha$; —CH=CH-phenyl, which phenyl may be substituted with $R^\alpha$; —$(CH_2)_{0-4}O(CH_2)_{0-1}$-pyridyl, which pyridyl may be substituted with $R^\alpha$; —$NO_2$; —CN; —$N_3$; —$(CH_2)_{0-4}N(R^\alpha)_2$; —$(CH_2)_{0-4}N(R^\alpha)C(O)R^\alpha$; —$N(R^\alpha)C(S)R^\alpha$; —$(CH_2)_{0-4}N$ $(R^\alpha)C(O)NR^\alpha_2$; —$N(R^\alpha)C(S)NR^\alpha_2$; —$(CH_2)_{0-4}N(R^\alpha)C(O)OR^\alpha$; —$N(R^\alpha)N(R^\alpha)C(O)R^\alpha$; —$N(R^\alpha)N(R^\alpha)C(O)NR^\alpha_2$; —$N(R^\alpha)N(R^\alpha)C(O)OR^\alpha$; —$(CH_2)_{0-4}C(O)R^\alpha$; —$C(S)R^\alpha$; —$(CH_2)_{0-4}C(O)OR^\alpha$; —$(CH_2)_{0-4}C(O)SR^\alpha$; —$(CH_2)_{0-4}C(O)OSiR^\alpha_3$; —$(CH_2)_{0-4}OC(O)R^\alpha$; —$OC(O)(CH_2)_{0-4}SR$—$SC(S)SR^\alpha$; —$(CH_2)_{0-4}SC(O)R^\alpha$; —$(CH_2)_{0-4}C(O)NR^\alpha_2$; —$C(S)NR^\alpha_2$; —$C(S)SR^\alpha$; —$SC(S)SR^\alpha$, —$(CH_2)_{0-4}OC(O)NR^\alpha_2$; —$C(O)N(OR^\alpha)R^\alpha$; —$C(O)C(O)R^\alpha$; —$C(O)CH_2C(O)R^\alpha$; —$C(NOR^\alpha)R^\alpha$; —$(CH_2)_{0-4}SSR^\alpha$; —$(CH_2)_{0-4}S(O)_2R^\alpha$; —$(CH_2)_{0-4}S(O)_2OR^\alpha$; —$(CH_2)_{0-4}OS(O)_2R^\alpha$; —$S(O)_2NR^\alpha_2$; —$(CH_2)_{0-4}S(O)R^\alpha$; —$N(R^\alpha)S(O)_2NR^\alpha_2$; —$N(R^\alpha)S(O)_2R^\alpha$; —$N(OR^\alpha)R^\alpha$; —$C(NH)NR^\alpha_2$; —$P(O)_2R^\alpha$; —$P(O)R^\alpha_2$; —$OP(O)R^\alpha_2$; —$OP(O)(OR^\alpha)_2$; $SiR^\alpha_3$; —$(C_{1-4}$ straight or branched)alkylene)O—$N(R^\alpha)_2$; or —$(C_{1-4}$ straight or branched)alkylene)C(O)O—$N(R^\alpha)_2$. Each $R^\alpha$ is independently hydrogen; $C_{1-6}$ alkyl; —$CH_2Ph$, —$O(CH_2)_{0-1}Ph$; —$CH_2$-(5- to 6-membered heteroaryl); $C_{3-8}$ cycloalkyl; $C_{6-10}$ aryl; 4- to 10-membered heterocyclyl; or 6- to 10-membered heteroaryl; and each $R^\alpha$ may be further substituted as described below.

Suitable monovalent substituents on $R^\alpha$ are independently halogen, —$(CH_2)_{0-2}R^\beta$; —$(CH_2)_{0-2}OH$; —$(CH_2)_{0-2}OR^\beta$; —$(CH_2)_{0-2}CH(OR^\beta)_2$; —CN; —$N_3$; —$(CH_2)_{0-2}C(O)R^\beta$; —$(CH_2)_{0-2}C(O)OH$; —$(CH_2)_{0-2}C(O)OR^\beta$; —$(CH_2)_{0-2}SR^\beta$; —$(CH_2)_{0-2}SH$; —$(CH_2)_{0-2}NH_2$; —$(CH_2)_{0-2}NHR^\beta$; —$(CH_2)_{0-2}NR^\beta_2$; —$NO_2$; $SiR^\beta_3$; —$OSiR^\beta_3$; —$C(O)SR^\beta$; —$(C_{1-4}$ straight or branched alkylene)C(O)OR$^\beta$; or —$SSR^\beta$; wherein each $R^\beta$ is independently selected from $C_{1-4}$ alkyl; —$CH_2Ph$; —$O(CH_2)_{0-1}Ph$; $C_{3-8}$ cycloalkyl; $C_{6-10}$ aryl; 4- to 10-membered heterocyclyl; or 6- to 10-membered heteroaryl. Suitable divalent substituents on a saturated carbon atom of $R^\alpha$ include =O and =S.

Suitable divalent substituents on a saturated carbon atom of an "optionally substituted" group include the following: =O; =S; =NNR$^\gamma_2$; =NNHC(O)R$^\gamma$; =NNHC(O)OR$^\gamma$; =NNHS(O)$_2$R$^\gamma$; =NR$^\gamma$; =NOR$^\gamma$; —O(C(R$^\gamma_2$))$_{2-3}$O—; or —S(C(R$^\gamma_2$))$_{2-3}$S—; wherein each independent occurrence of $R^\gamma$ is selected from hydrogen; $C_{1-6}$ alkyl, which may be substituted as defined below; $C_{3-8}$ cycloalkyl; $C_{6-10}$ aryl; 4- to 10-membered heterocyclyl; or 6- to 10-membered heteroaryl. Suitable divalent substituents that are bound to vicinal substitutable carbons of an "optionally substituted" group include: —O(CR$^\beta_2$)$_{2-3}$O—; wherein each independent occurrence of $R^\beta$ is selected from hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^\gamma$ include halogen; —$R^\delta$; —OH; —OR$^\delta$; —CN; —C(O)OH; —C(O)OR$^\delta$; —NH$_2$; —NHR$^\delta$; —NR$^\delta_2$; or —NO$_2$; wherein each $R^\delta$ is independently $C_{1-4}$ alkyl; —$CH_2Ph$; —$O(CH_2)_{0-1}Ph$; 4- to 10-membered heterocyclyl; or 6- to 10-membered heteroaryl.

Suitable substituents on a substitutable nitrogen of an "optionally substituted" group include —$R^\epsilon$; —NR$^\epsilon_2$; —C(O)R$^\epsilon$; —C(O)OR$^\epsilon$; —C(O)C(O)R$^\epsilon$; —C(O)CH$_2$C(O)R$^\epsilon$; —S(O)$_2$R$^\epsilon$; —S(O)$_2$NR$^\epsilon_2$; —C(S)NR$^\epsilon_2$; —C(NH)NR$^\epsilon_2$; or —N(R$^\epsilon$)S(O)$_2$R$^\epsilon$; wherein each $R^\epsilon$ is independently hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^\epsilon$ are independently halogen; —$R^\delta$; —OH; —OR$^\delta$; —CN; —C(O)OH; —C(O)OR$^\delta$; —NH$_2$; —NHR$^\delta$; —NR$^\delta_2$; or —NO$_2$; wherein each $R^\delta$ is independently $C_{1-4}$ alkyl; —$CH_2Ph$; —$O(CH_2)_{0-1}Ph$; $C_{6-10}$ aryl; 4- to 10-membered heterocyclyl; or 6- to 10-membered heteroaryl.

In some cases, "substituted" may refer to replacement of a hydrogen atom with a substituent as described herein.

However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group.

In some embodiments, the compound is selected from

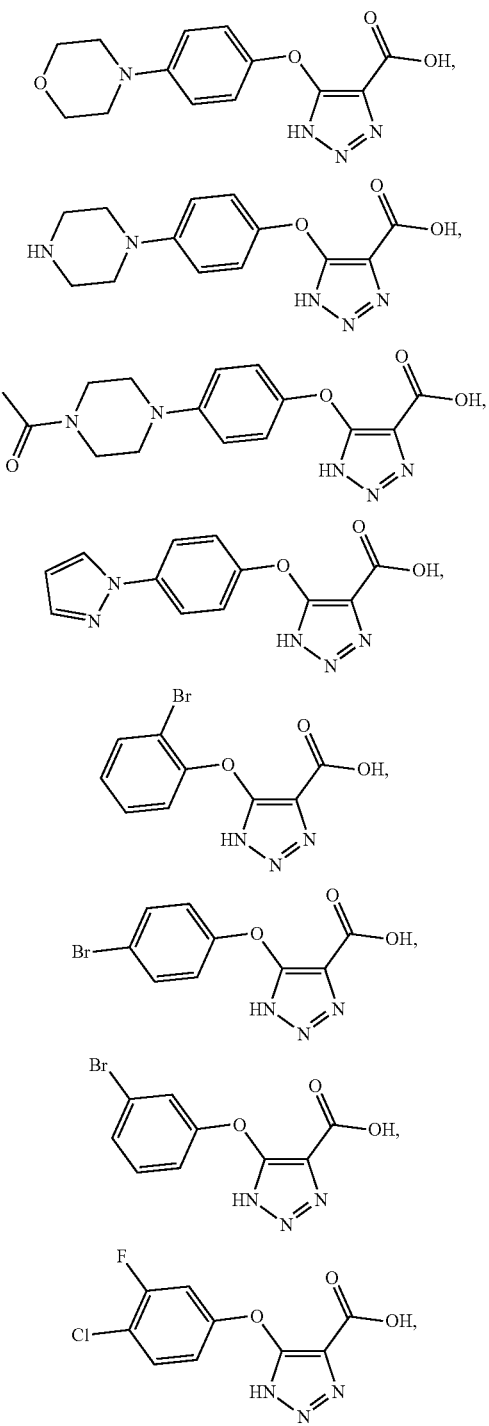

-continued

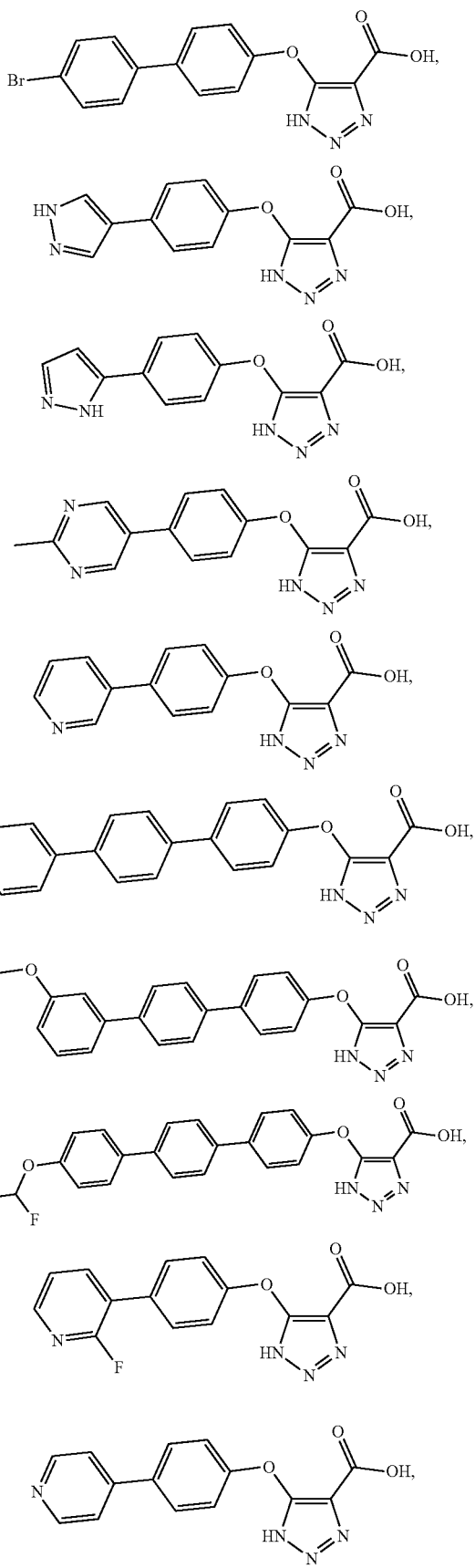

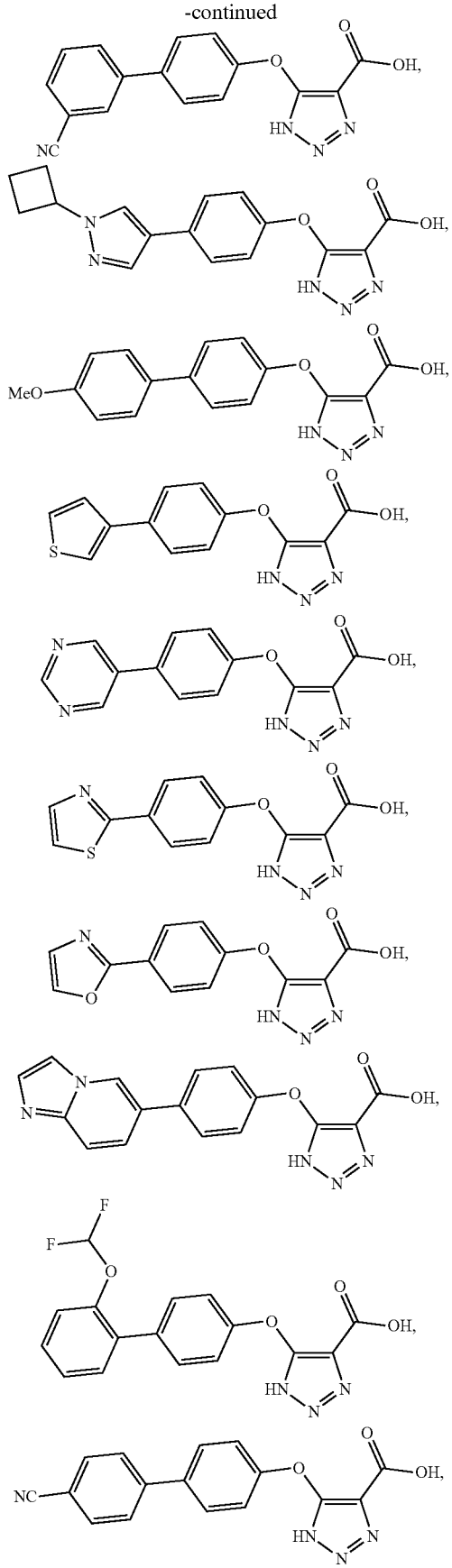
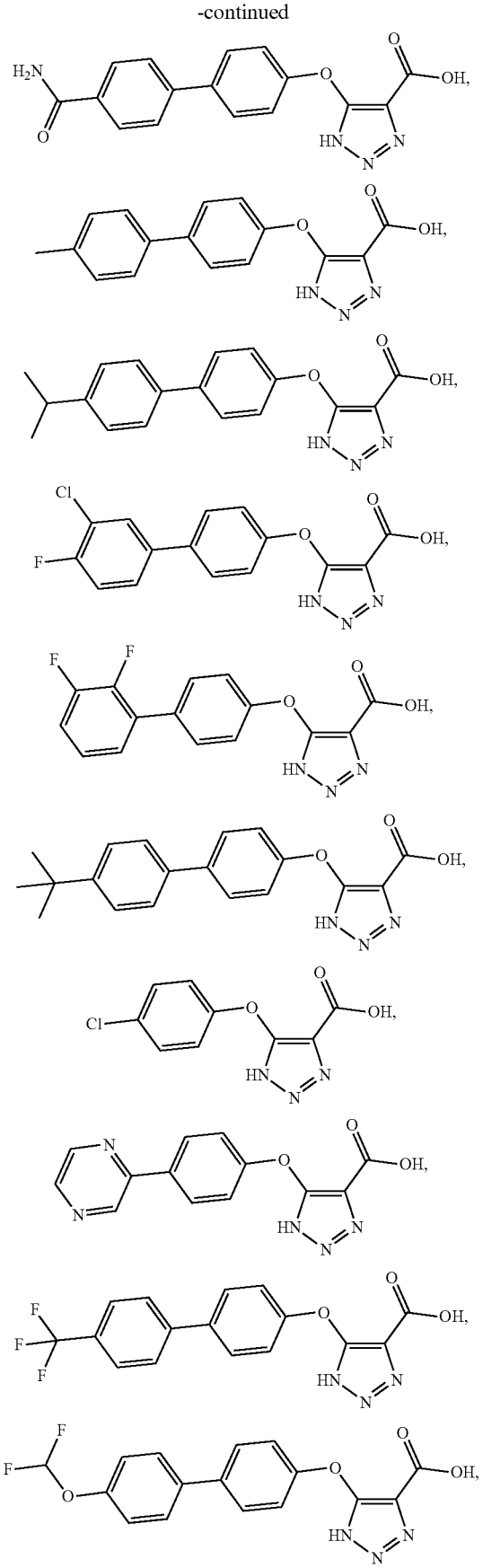

-continued
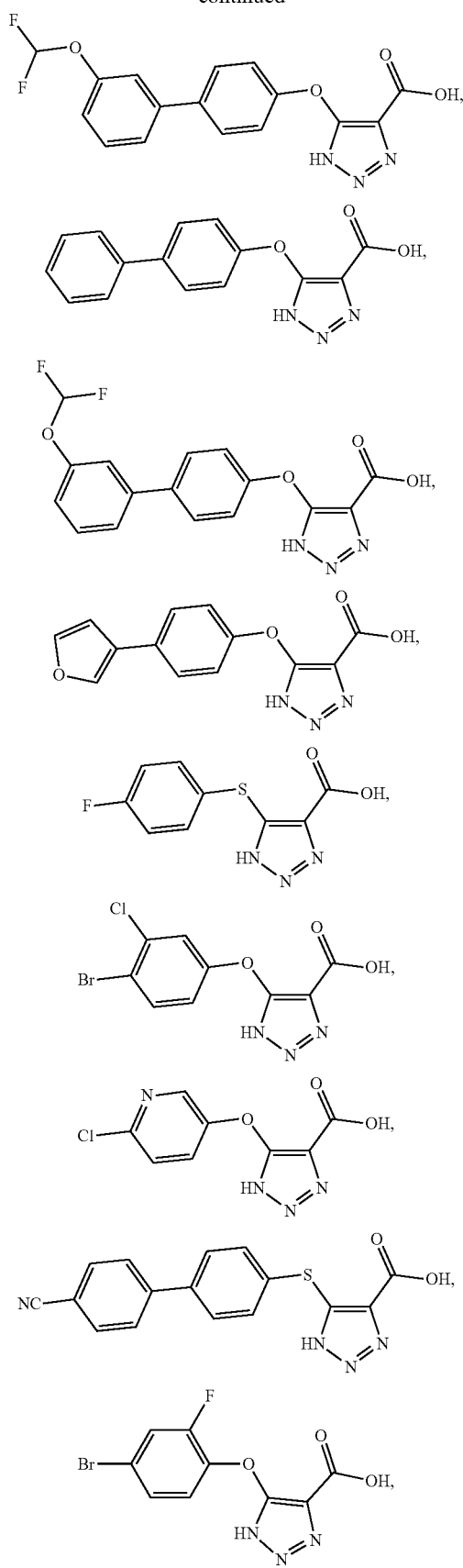
-continued
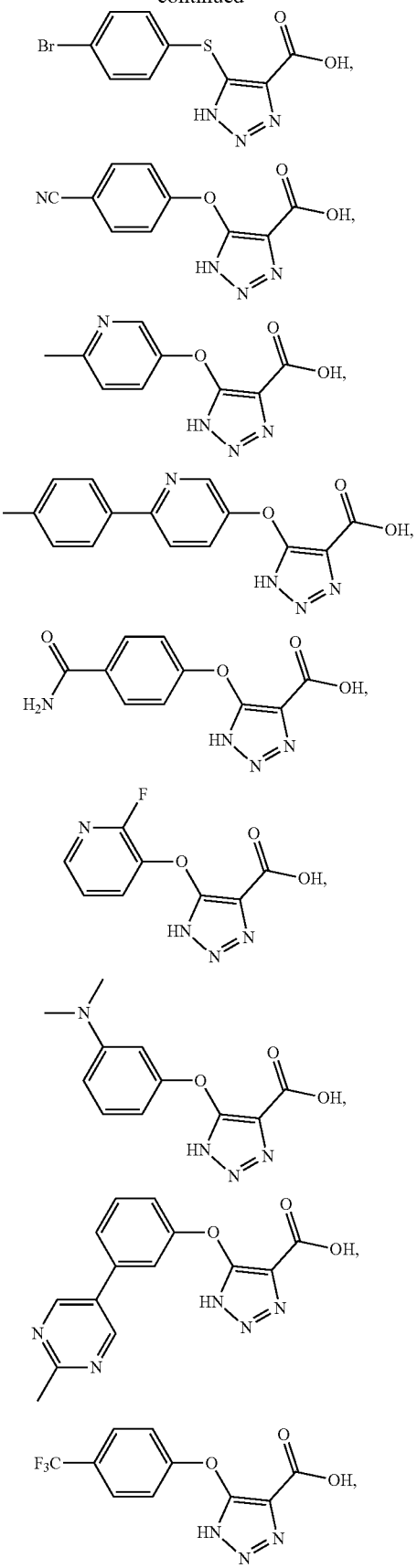

-continued
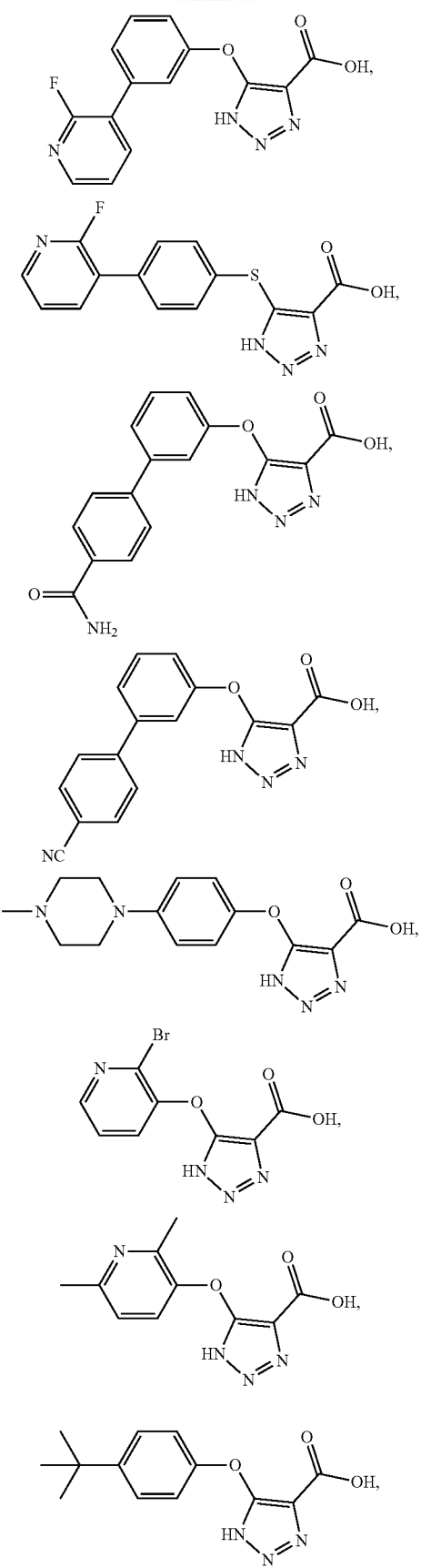
-continued
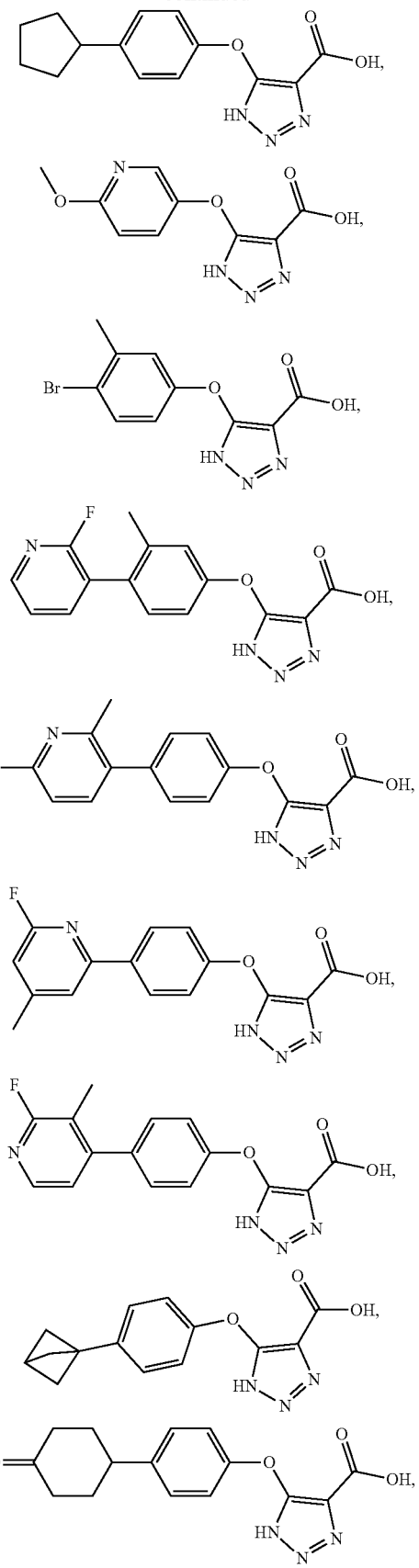

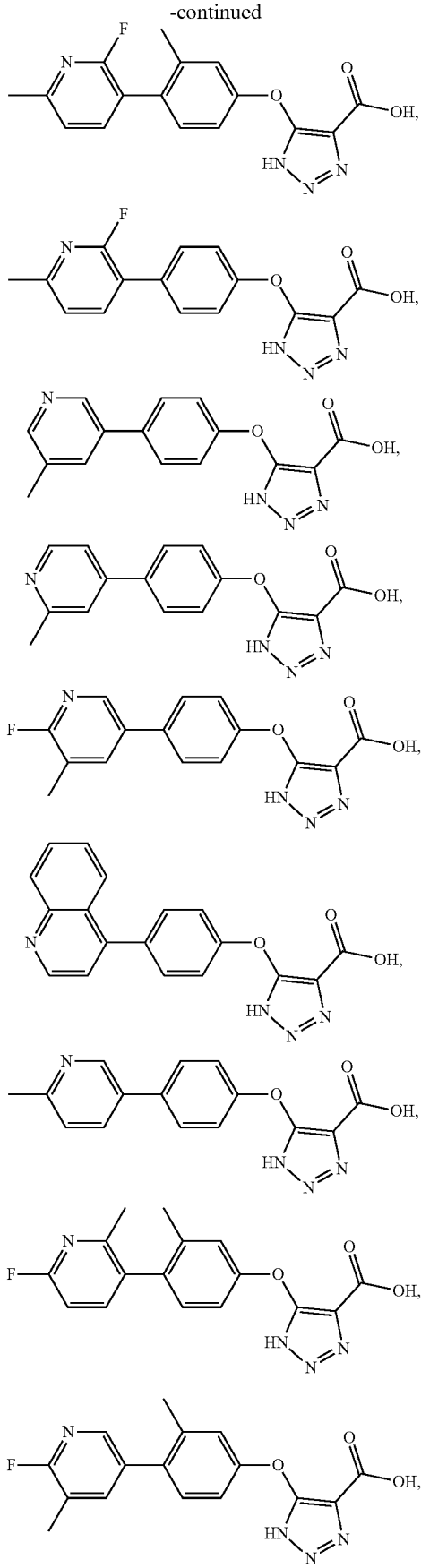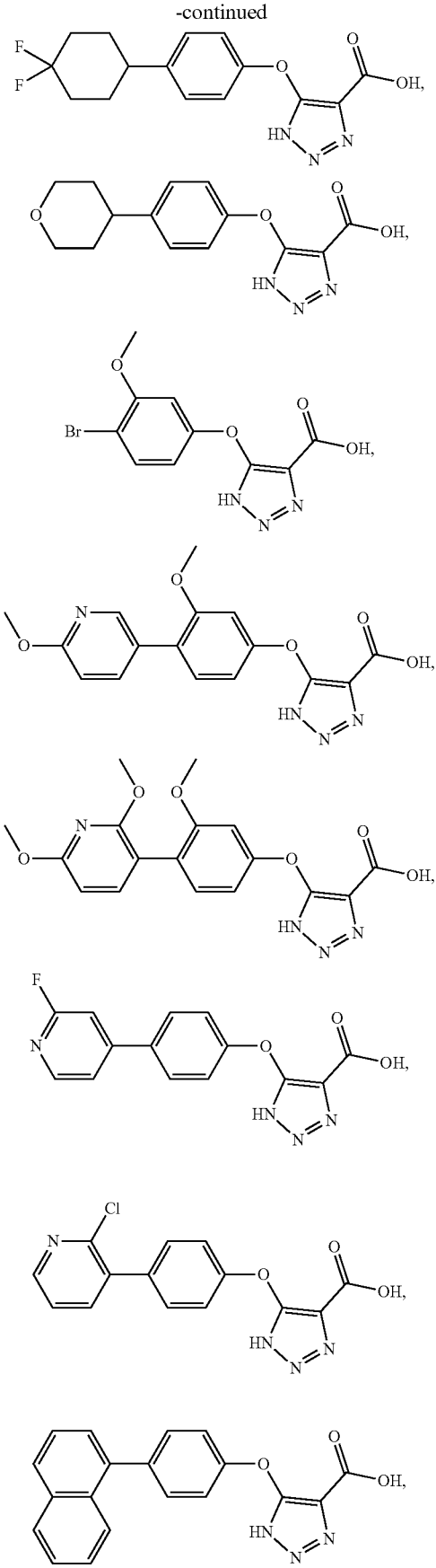

-continued
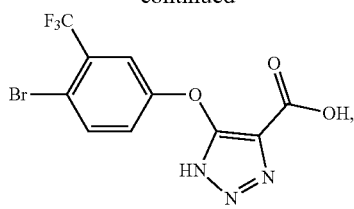
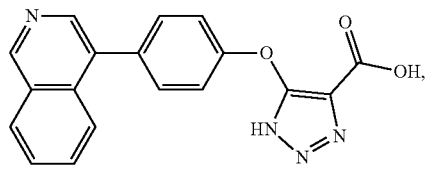
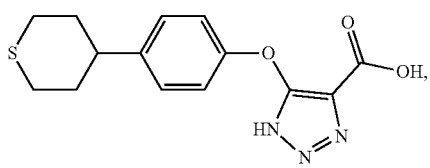
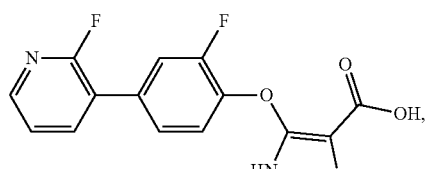
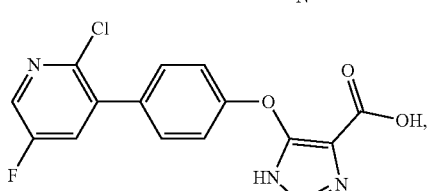
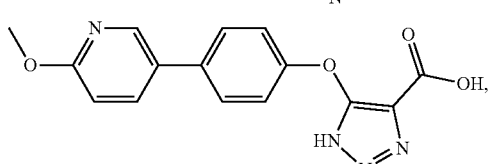
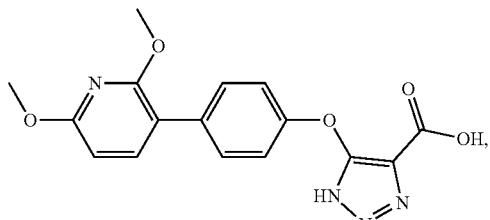
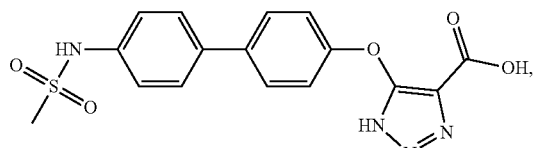
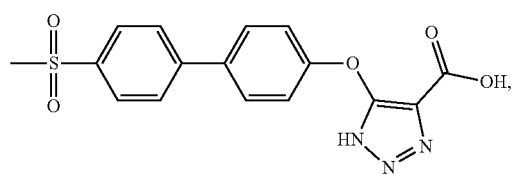
-continued
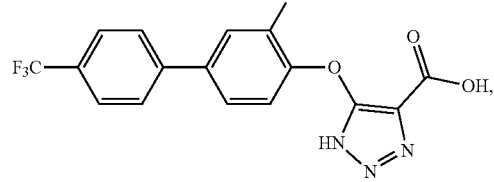
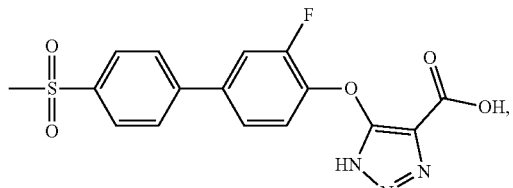
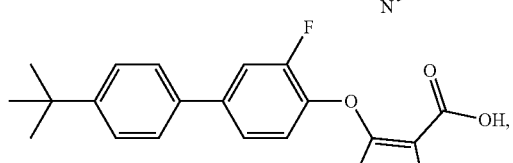
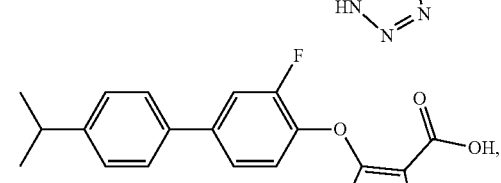
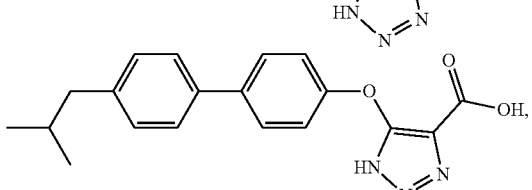
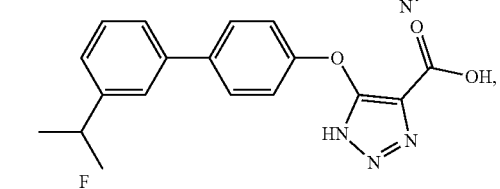
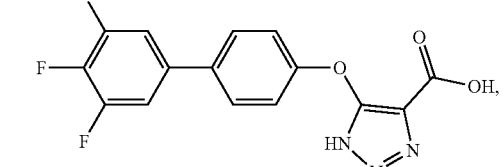
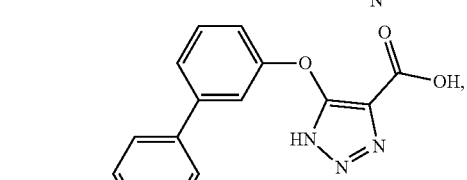
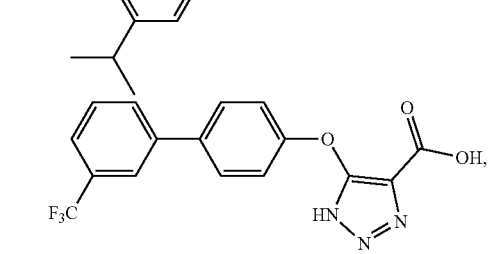

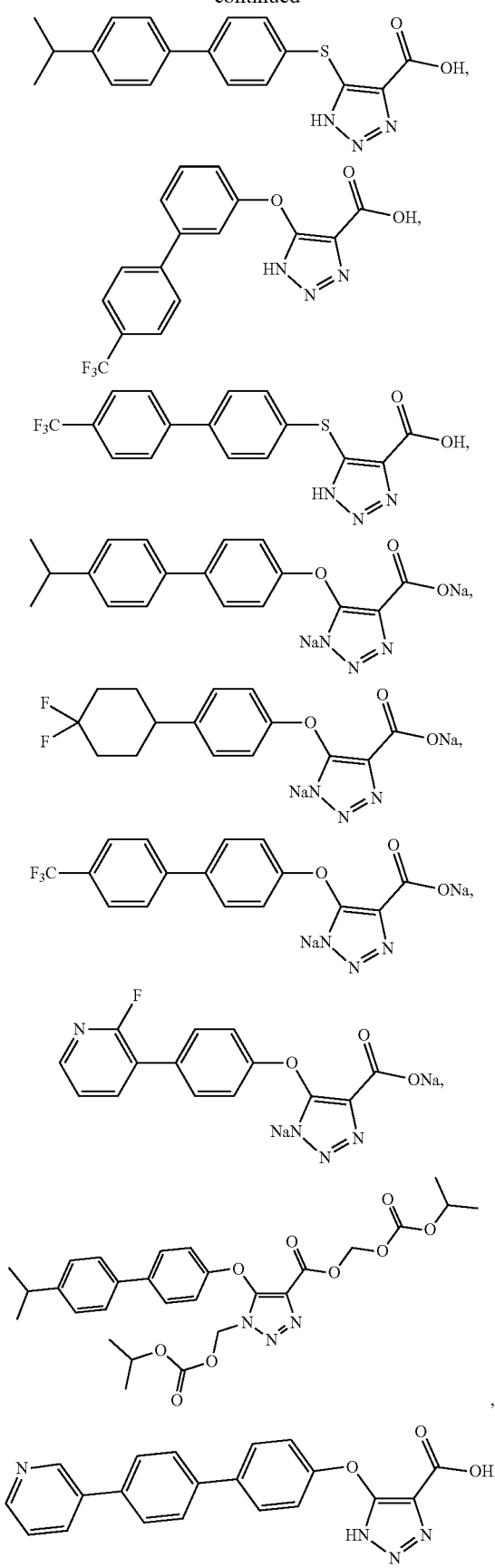
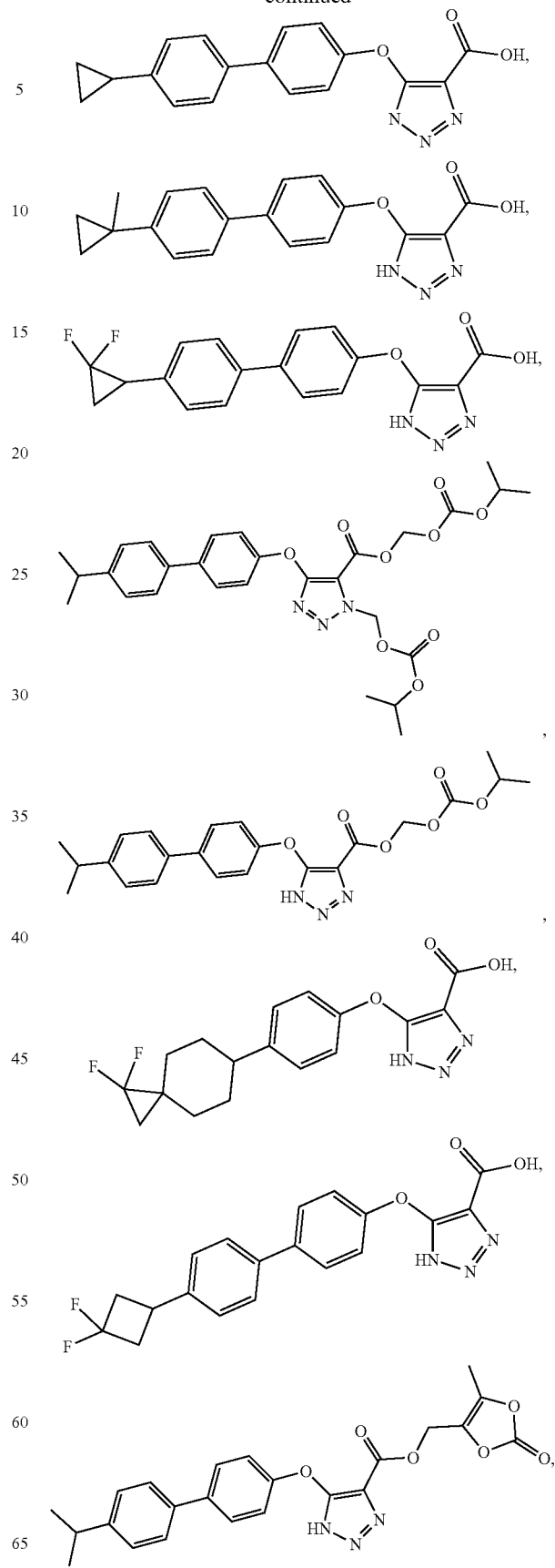

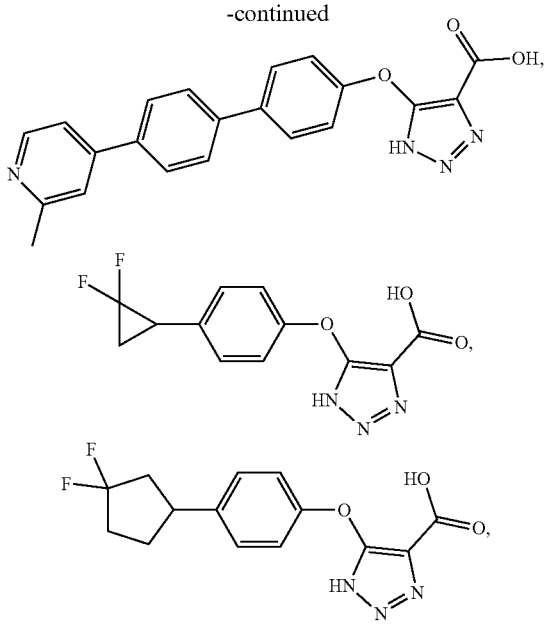

and pharmaceutical acceptable salts thereof.

The compounds may be prepared using the methods disclosed herein and routine modifications thereof, which will be apparent given the disclosure herein and methods well known in the art. Conventional and well-known synthetic methods may be used in addition to the routes described below. The synthesis of typical compounds described herein may be accomplished as described in the following examples. If available, reagents may be purchased commercially, e.g., from Sigma Aldrich or other chemical suppliers. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

The starting materials for the following reactions are generally known compounds or can be prepared by known procedures including modifications thereof. For example, many of the starting materials are available from commercial suppliers such as Aldrich Chemical Co. (Milwaukee, Wis., USA), Bachem (Torrance, Calif., USA), Emka-Chemie or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplemental (Elsevier Science Publishers, 1989) Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

As shown below in Scheme 1, dicarboxylic ester (A) can be reacted with an alkyl azide (B) to form hydroxy-substituted triazole (B). Subsequent conversion to halide-substituted triazole (D) and displacement with phenol or thiophenol (E) provides protected triazole (F). The triazole can be deprotected to provide ester product (G), e.g., wherein $R^1$ is an alkyl group or arylalkyl group, which can then be hydrolyzed to form the corresponding acid product, wherein $R^1$ is H.

Scheme 1

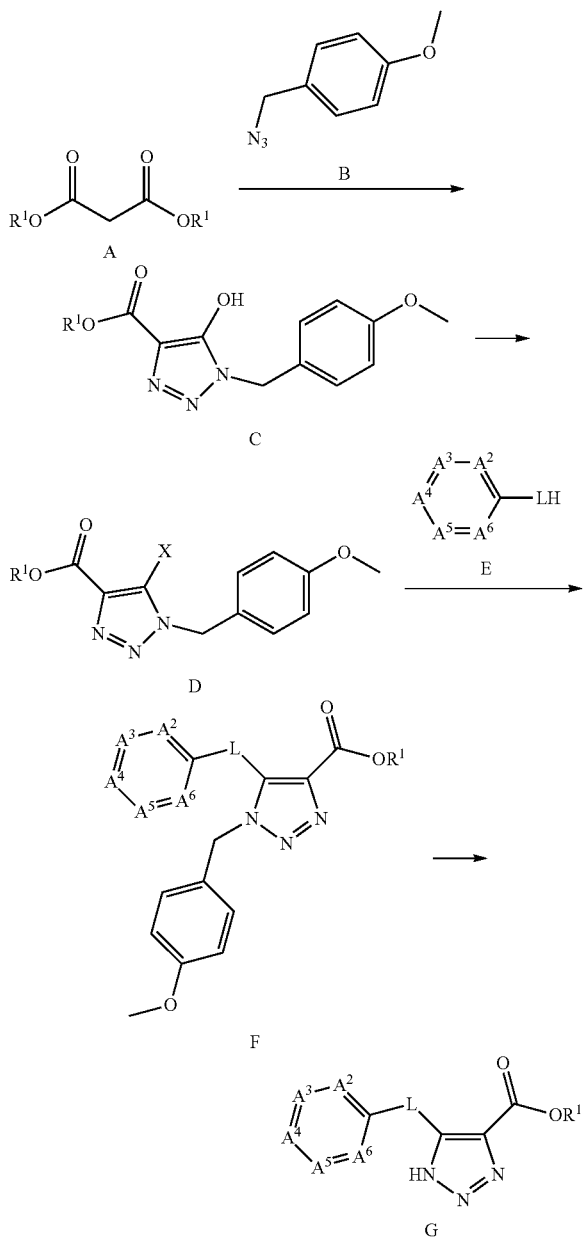

Another route for the preparation of compounds according to Formula I is depicted in Scheme 2. A haloaryl-substituted triazole (J) can be reacted with an R⁴-substituted boronic acid (K) in the presence of a organometallic catalyst (e.g., a palladium catalyst such as [1,1'-bis-(diphenylphosphino)ferrocene]dichloropalladium(II)) under Suzuki-type reaction conditions to provide protected triazole (M). The triazole can be deprotected to provide ester product (Q), e.g., wherein R¹ is an alkyl group or arylalkyl group, which can then be hydrolyzed to form the corresponding acid product, wherein R¹ is H.

Alternatively, haloaryl-substituted triazole (J) can be converted to the corresponding pinacolborane (U) as shown in Scheme 3. Coupling with an R⁴-substituted halide (V) can then be conducted using a palladium catalyst or other suitable catalyst to provide protected triazole (Y). The triazole can be deprotected to provide ester product (Z), e.g., wherein R¹ is an alkyl group or arylalkyl group, which can then be hydrolyzed to form the corresponding acid product, wherein R¹ is H.

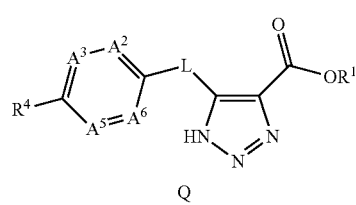

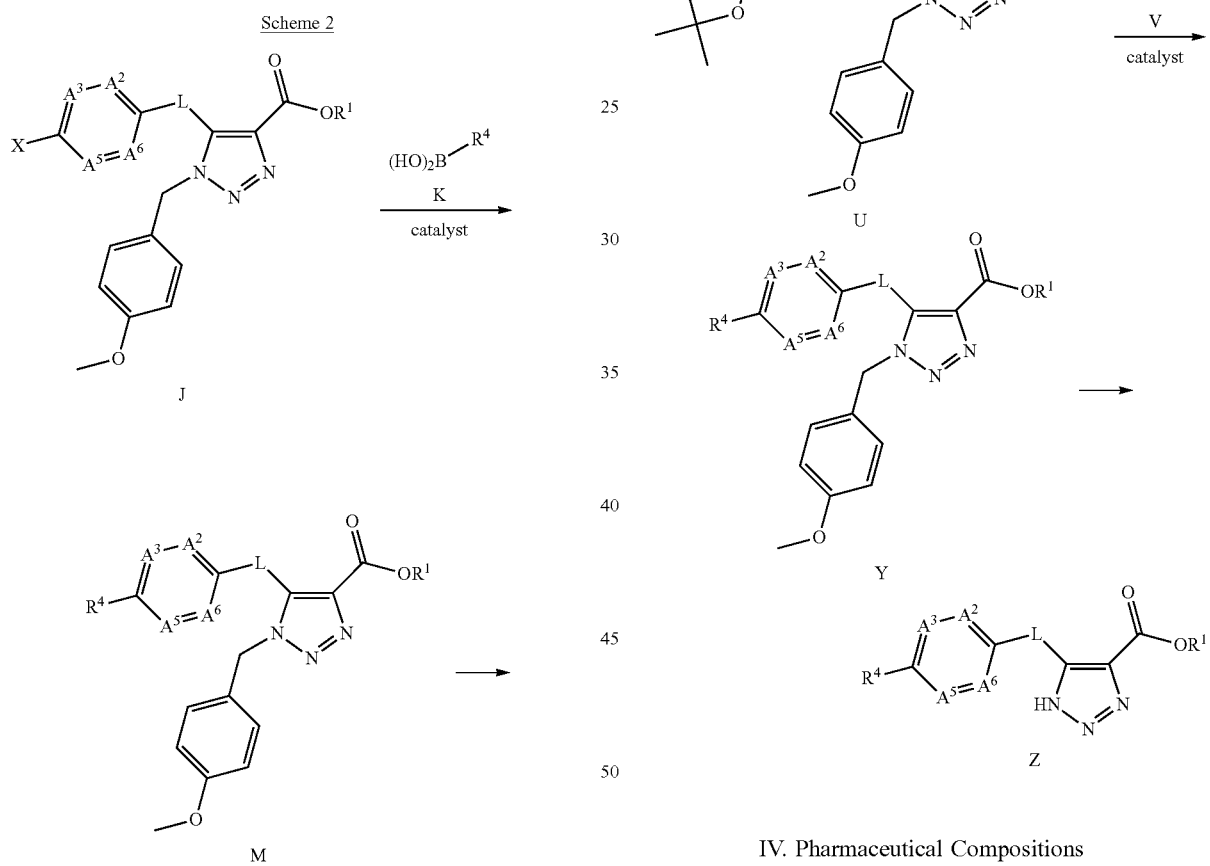

IV. Pharmaceutical Compositions

Also provided are pharmaceutical compositions containing compounds as described herein (e.g., a compound of Formula I, Formula Ia, Formula Ib, Formula Ic, or Formula II) and one or more pharmaceutically acceptable excipients. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active ingredient in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or *arachis* oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing GO inhibitors can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semi-permeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Transdermal delivery of GO inhibitors can be accomplished by means of iontophoretic patches and the like. The compound can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

In some embodiments, the pharmaceutical composition includes a GO inhibitor as described herein and one or more additional active agents for treating kidney stones. Examples of such active agents include, but are not limited to, thiazides (e.g., bendroflumethiazide, chlorothiazide, chlorthalidone, hydrochlorothiazide, indapamide, methyclothiazide, metolazone, polythiazide, and the like); citrate salts (e.g., sodium citrate, potassium citrate, and the like); phosphate salts (e.g, monopotassium phosphate, dipotassium phosphate, and the like); vitamin $B_6$ compounds (e.g., pyridoxine, pyridoxal, pyridoxamine, and the like); cystine-binding thiol compounds (e.g., α-mercaptopropionylglycine, D-penicillamine, captopril, and the like); purine analog xanthine oxidase inhibitors (e.g., allopurinol, oxypurinol, and the like); and other xanthine oxidase inhibitors (e.g., febuxostate, topiroxostat, and the like).

V. Methods for Treating PH1 and Kidney Stones

Compounds of Formula I (e.g., compounds of Formula Ia) and Formula II are useful as glycolate oxidase inhibitors, and methods for inhibiting glycolate oxidase are also provided herein. The methods include contacting glycolate oxidase with a compound according to Formula I (e.g., a compound of Formula Ia) or Formula II to a subject in need thereof. Inhibiting glycolate oxidase generally includes contacting the glycolate oxidase with an amount of the compound sufficient to reduce the activity of the glycolate oxidase as compared to the glycolate oxidase activity in the absence of the compound. For example, contacting glycolate oxidase with a compound according to Formula I, Formula Ia, Formula Ib, Formula Ic, or Formula II can result in from about 1% to about 99% glycolate oxidase inhibition (i.e., the activity of the inhibited glycolate oxidase ranges from 99% to 1% of the glycolate oxidase activity in the absence of the compound). The level of glycolate oxidase inhibition can range from about 1% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90%, or from about 90% to about 99%. The level of glycolate oxidase inhibition can range from about 5% to about 95%, or from about 10% to about 90%, or from about 20% to about 80%, or from about 30% to about 70%, or from about 40% to about 60%. In some embodiments, contacting glycolate oxidase with a compound as described herein will result in complete (i.e., 100%) glycolate oxidase inhibition.

In primary hyperoxaluria type I (PH1), mutation of alanine-glyoxylate transaminate (AGT) disrupts the glyoxylate detoxification pathway. Mutation of AGT prevents AGT from converting glyoxylate to pyruvate, and the resulting build-up of glyoxylate results in higher levels of oxalate and oxalate-containing kidney stones. Glycolate oxidase (GO) is a peroxisomal hepatic enzyme which catalyzes the oxidation of glycolate to glyoxylate, the AGT substrate. As such, GO plays a pivotal role in glyoxylate production while AGT plays a pivotal role in glyoxylate detoxification. The present invention provides compounds and methods for treating PH1 by targeting GO, the source of the AGT substrate. GO inhibitors as described herein can reduce glyoxylate levels in PH1 patients, thus compensating for the inability of mutant AGT—located downstream of GO in the glyoxylate detoxification pathway—to metabolize glyoxylate and preventing the harmful build-up of oxalate.

Also provided are methods for treating primary hyperoxaluria (PH1). PH1 has a prevalence of 1-3 per million individuals and an incidence of 1-9: 100,000 live births per year in Europe [Salido, supra]. PH1 is caused by mutations of the gene encoding peroxisomal enzyme AGT, which fails to detoxify glyoxylate and leads to a marked increase in oxalate synthesis by the liver. In PH1, excreted urinary oxalate (UOx) is elevated leading to the production of insoluble calcium oxalate (CaOx) crystals which tend to precipitate primarily in the kidney, forming kidney stones and diffuse nephrocalcinosis [Kaufman, supra]. This impairs renal function which progresses to end-stage renal disease (ESRD). Once renal function declines to a glomerular filtration rate (GFR) below 30 ml/min/1.73 m², the amount of oxalate produced by the liver can no longer be cleared by the kidneys, leading to systemic deposition of CaOx (oxalosis). First symptoms of PH1 include hematuria, abdominal pain, passage of a stone, or repeated urinary tract infections. The initial diagnosis is based on clinical and sonographic findings, and UOx assessment. AGT activity assessment in a liver biopsy and/or DNA analysis is required to confirm a PH1 diagnosis and to initiate conservative treatment (high fluid intake, pyridoxine, CaOx crystallization inhibitors), aimed at maintaining renal function. The most effective treatment for PH1 is liver transplantation (LTx), alone (pre-emptive) or combined with kidney transplantation [Cochat, et al. (2012) *Nephrol Dial Transplant.* 27: 1729].

In some embodiments, the methods for treating PH1 include administering a compound according to Formula I as described above (e.g., a compound of Formula Ia), a pharmaceutically acceptable salt thereof, or a pharmaceutical composition containing the compound or salt to a subject in need thereof. In some embodiments, the methods include administering a compound according to Formula II:

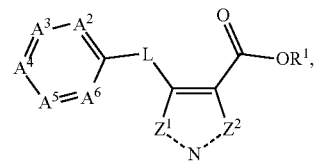

or a pharmaceutically acceptable salt thereof, wherein:

L is selected from O and S;

$A^2$ is selected from $CR^2$ and N;

$A^3$ is selected from $CR^3$ and N;

$A^4$ is selected from $CR^4$ and N;

$A^5$ and $A^6$ are independently selected from CH and N;

the dashed line connected to $Z^1$ is a double bond, $Z^1$ is N, the dashed line connected to $Z^2$ is a single bond, and $Z^2$ is $NR^5$; or the dashed line connected to $Z^1$ is a single bond, $Z^1$ is $NR^5$, the dashed line connected to $Z^2$ is a double bond, and $Z^2$ is N;

$R^1$ is selected from H, unsubstituted $C_{1-6}$ alkyl, substituted $C_{1-6}$ alkyl, —($C_{1-6}$ alkylene)-OC(O)—($C_{1-6}$ alkyl), and —($C_{1-6}$ alkylene)-OC(O)—($C_{1-6}$ alkoxy);

$R^2$ and $R^3$ are independently selected from H and halogen;

$R^4$ is selected from H, halogen, $C_{1-12}$ alkyl, $C_{1-12}$ alkoxy, $C_{6-12}$ aryl, $C_{3-8}$ cycloalkyl, 3- to 12-membered heterocyclyl, and 5- to 12-membered heteroaryl;

$R^4$ is optionally substituted with one or more $R^{4a}$; and each $R^{4a}$ is independently selected from $C_{1-12}$ alkyl, $C_{1-12}$ alkoxy, $C_{1-12}$ haloalkyl, $C_{1-12}$ haloalkoxy, halogen, —OH, —CO$_2$H, —SO$_3$, —CN, —NO$_2$, —N$_3$, $C_{2-12}$ alkenyl, $C_{2-12}$ alkynyl, $C_{3-8}$ cycloalkyl, $C_{3-8}$ halocycloalkyl, $C_{6-12}$ aryl, $C_{7-18}$ arylalkyl, 3- to 12-membered heterocyclyl, 5- to 12-membered heteroaryl, —N(R$^a$)$_2$, —C(O)N(R$^a$)$_2$, —OC(O)N(R$^a$)$_2$, —S(O)$_2$N(R$^a$)$_2$, —NR$^a$C(O)R$^b$, —C(O)R$^b$, and —OC(O)R$^b$;

each $R^a$ is independently selected from H and $C_{1-6}$ alkyl; and each $R^b$ is independently selected from $C_{1-6}$ alkyl and $C_{1-6}$ alkoxy;

$R^5$ is selected from H, unsubstituted $C_{1-6}$ alkyl, substituted $C_{1-6}$ alkyl, $C_{2-7}$ acyl, —($C_{1-6}$ alkylene)-OC(O)—($C_{1-6}$ alkyl), and —($C_{1-6}$ alkylene)-OC(O)—($C_{1-6}$ alkoxy);

provided that if L is S, $A^2$ is $CR^2$, $A^3$ is $CR^3$, $A^4$ is $CR^4$, and $A^5$ and $A^6$ are CH, then:

$R^4$ is other than methoxy, 4-bromophenyl, or 4-fluorophenyl when $R^2$ and $R^3$ are H, and $R^3$ is other than 4-bromophenyl or 4-fluorophenyl when $R^2$ and $R^4$ are H.

In some embodiments, the methods include administering a compound of Formula II wherein L is O, or a pharmaceutically acceptable salt thereof. In some embodiments, the methods include administering a compound selected from:

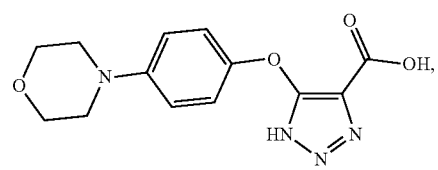

-continued
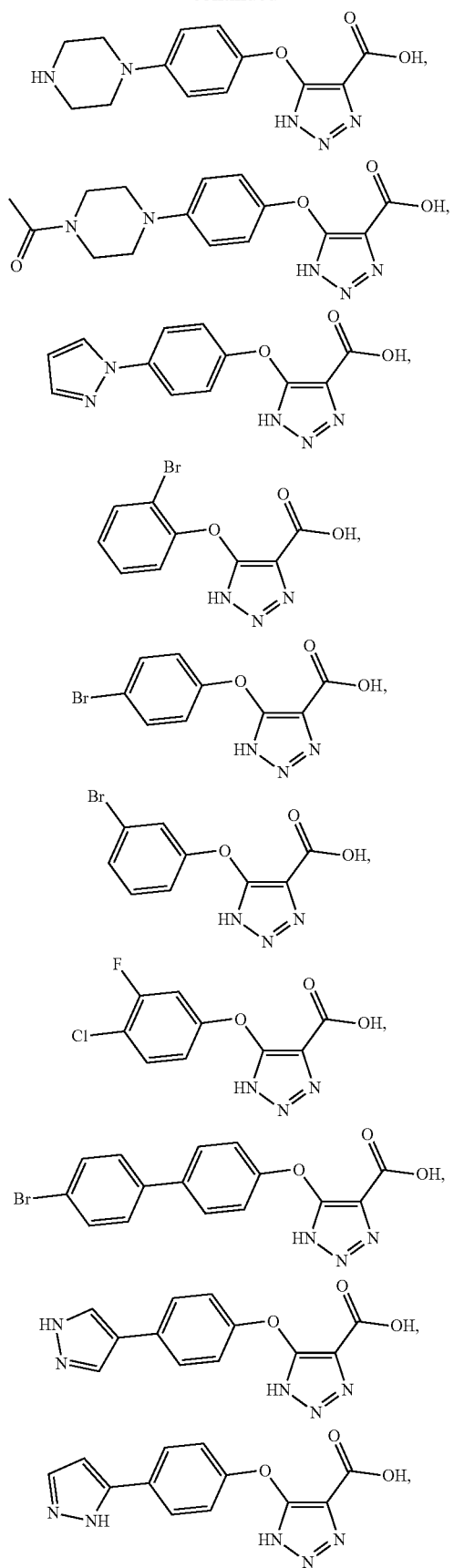
-continued
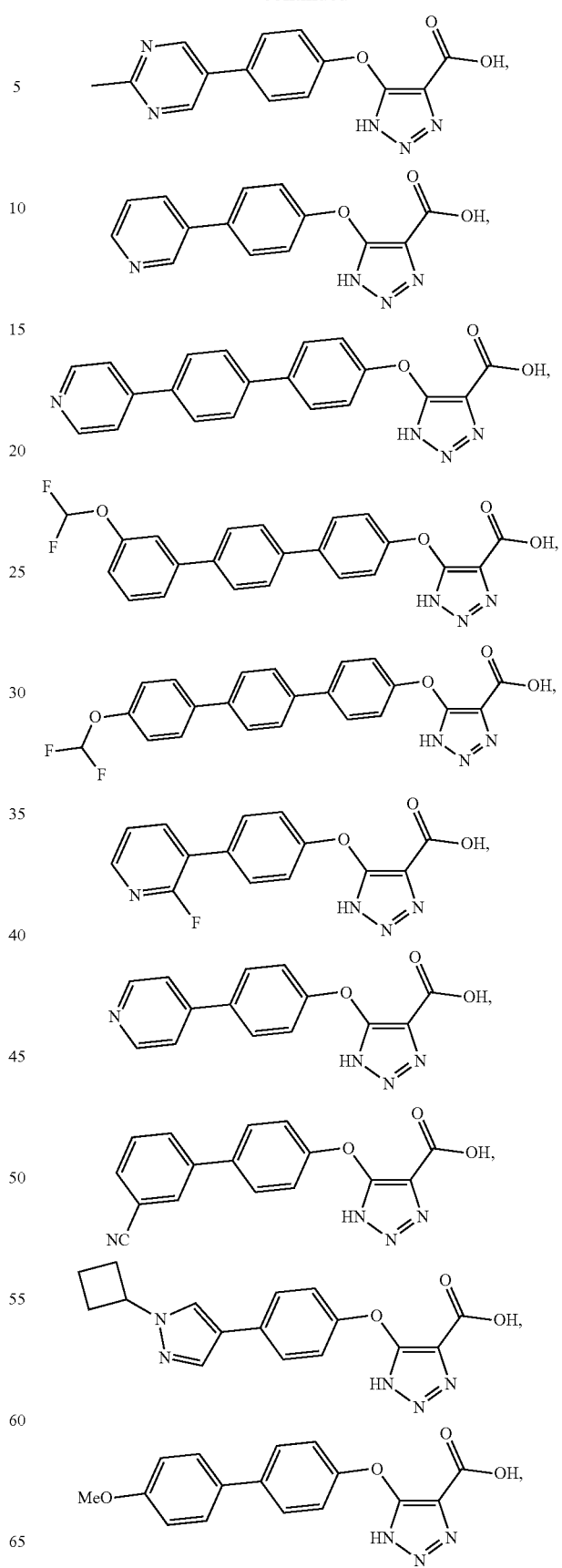

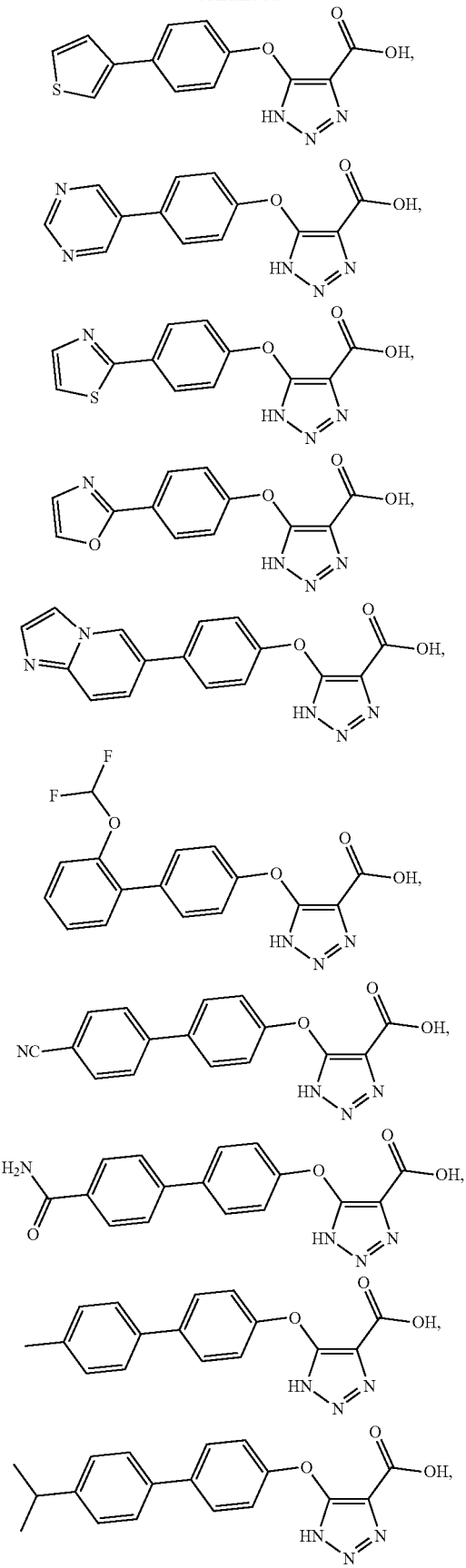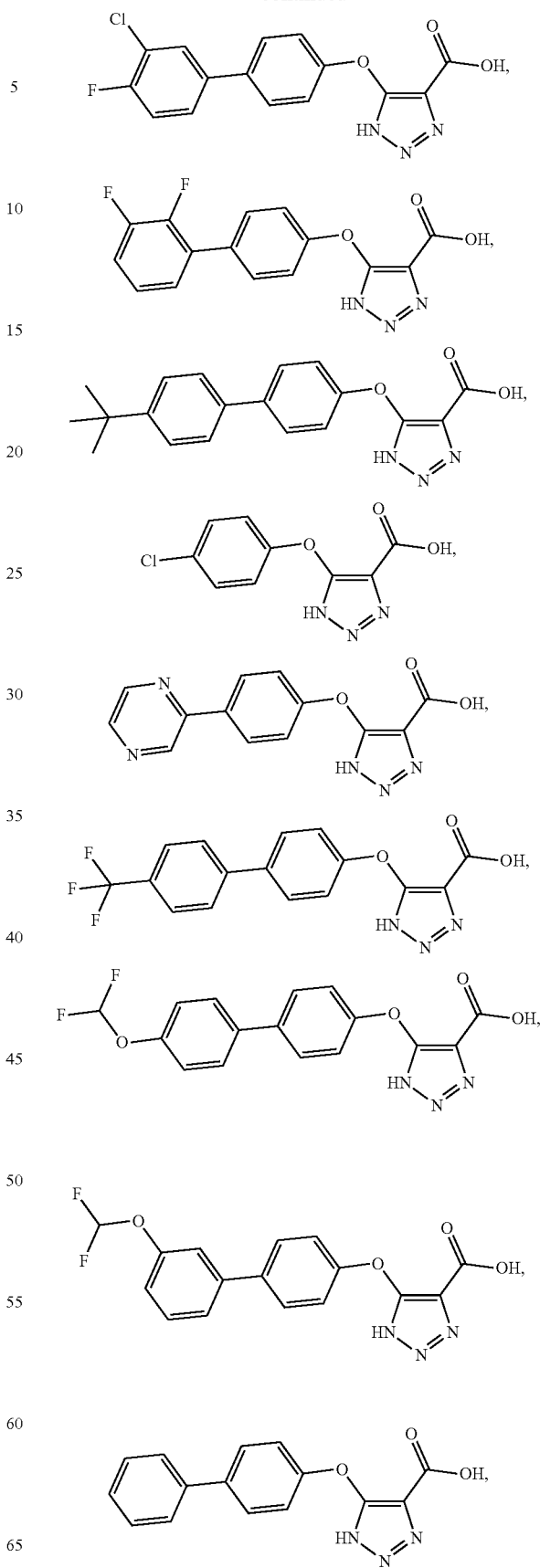

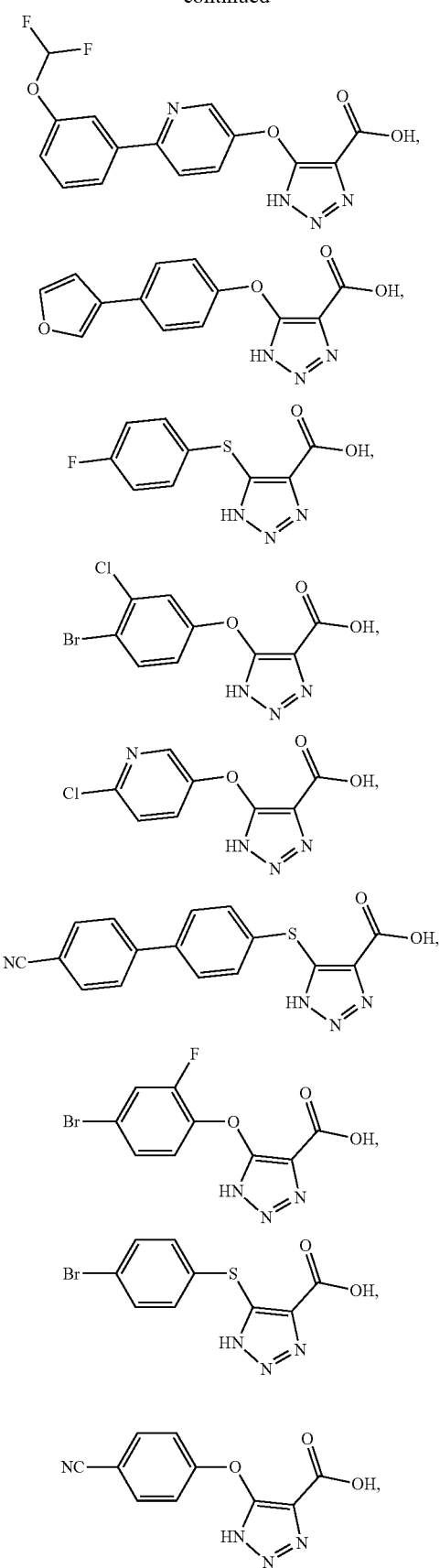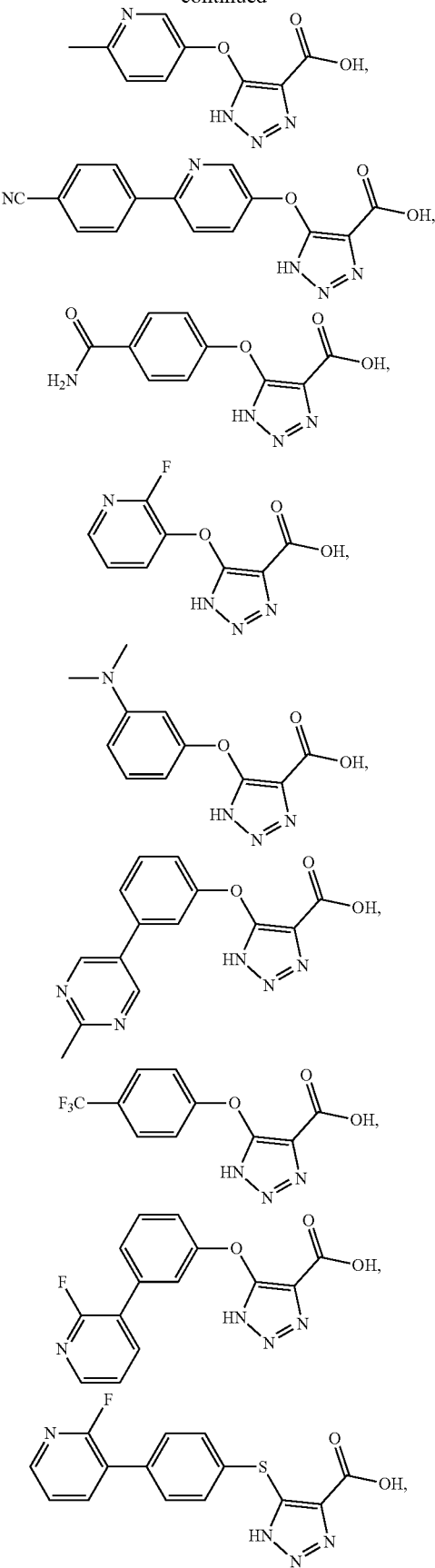

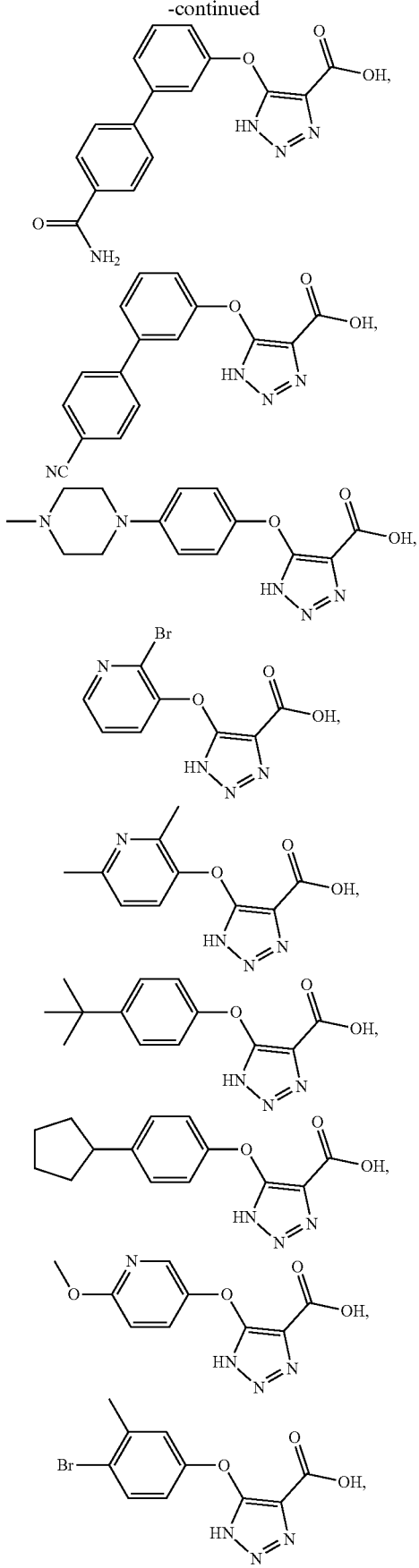
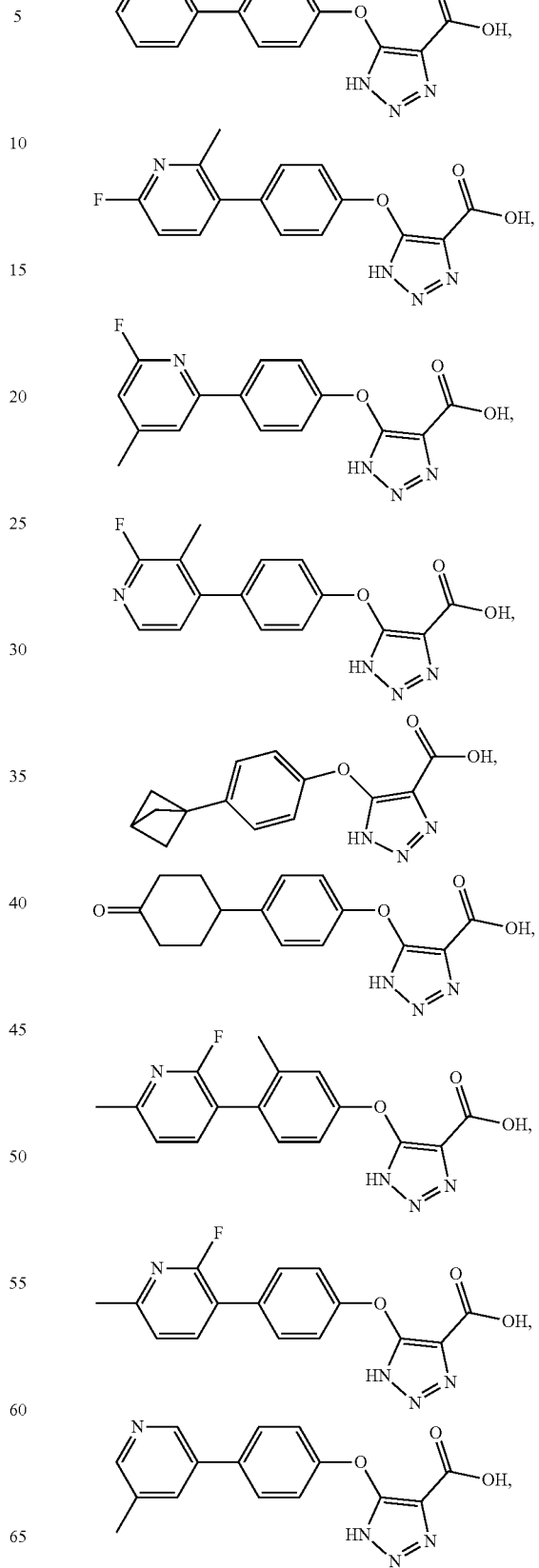

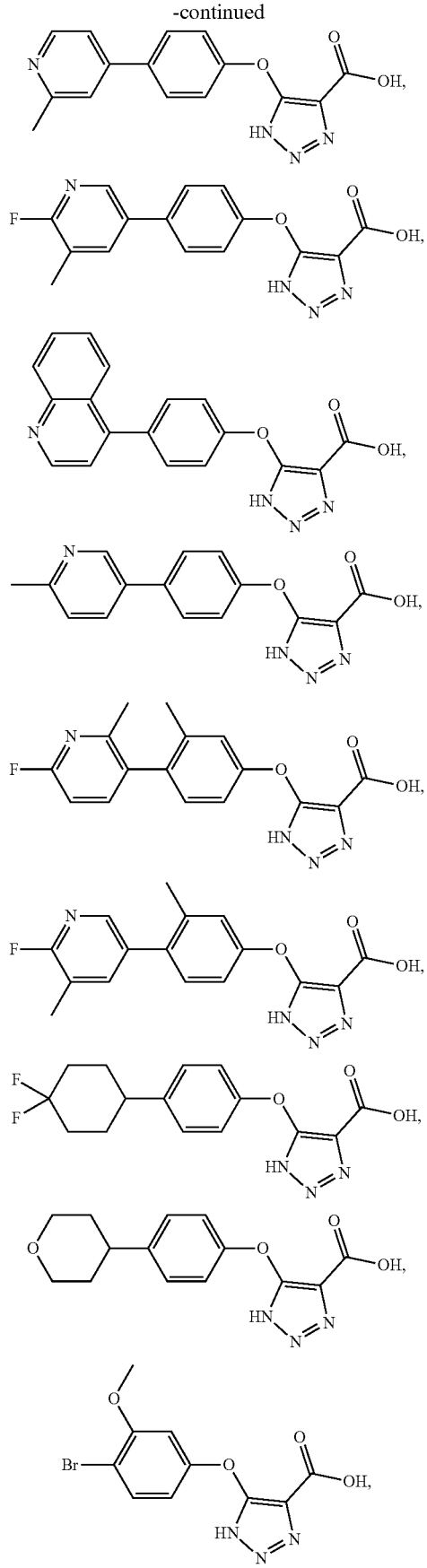

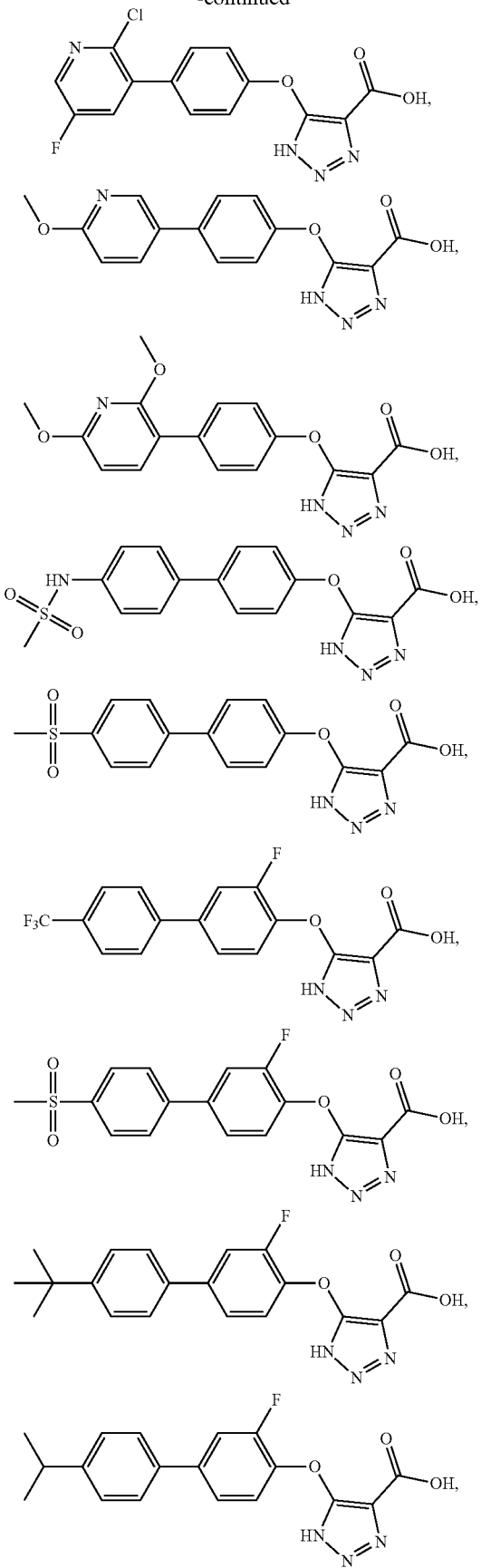
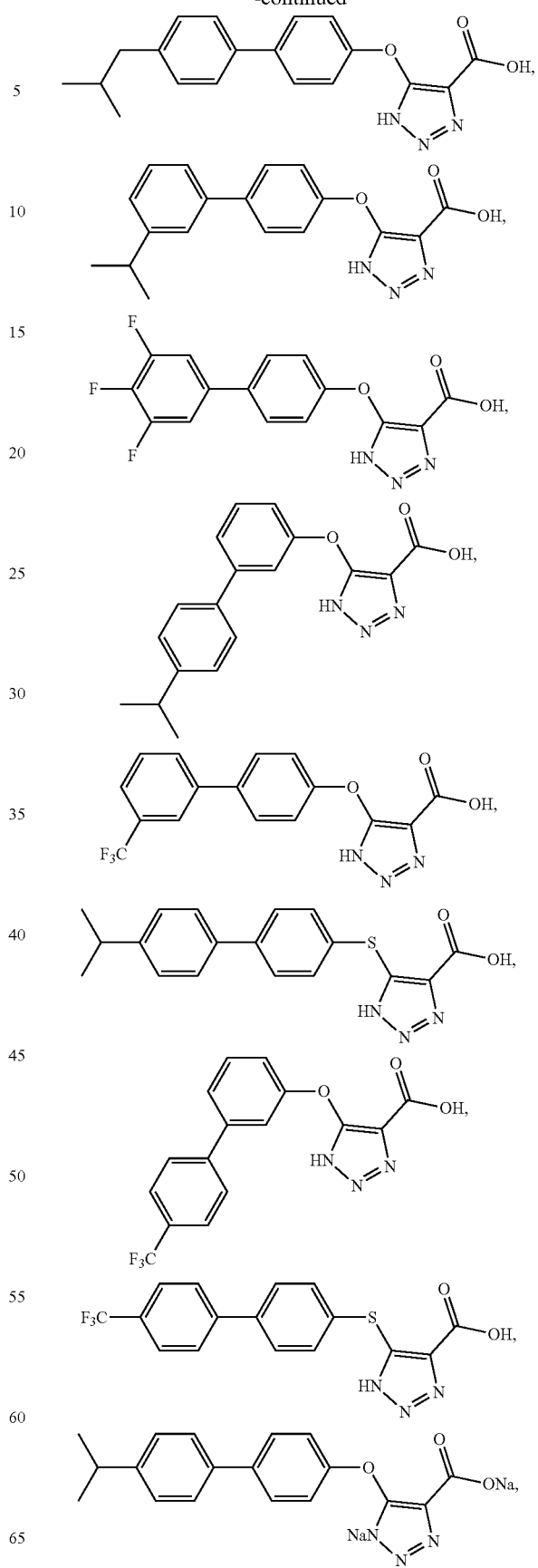

51
-continued
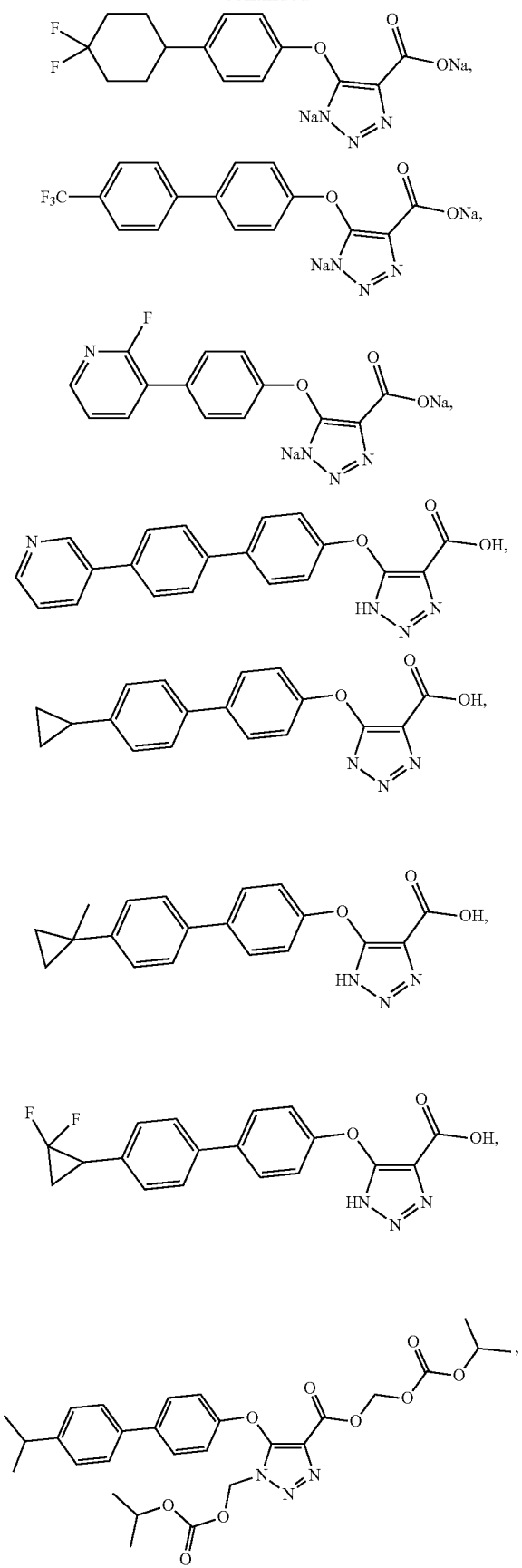
52
-continued
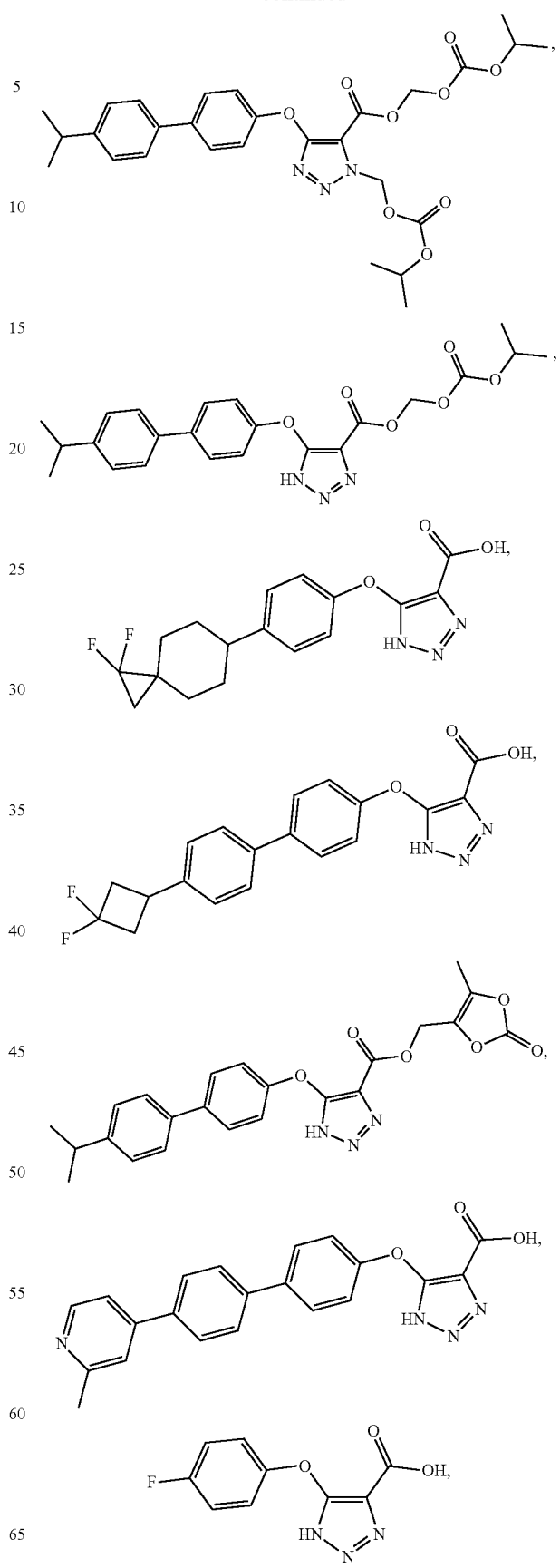

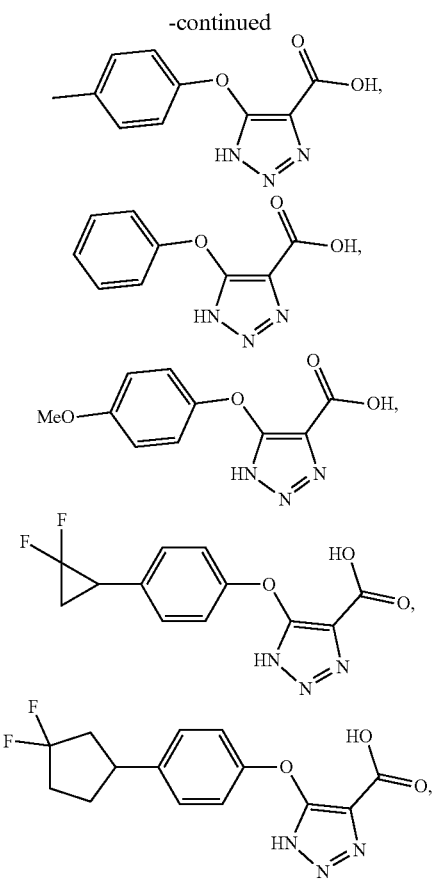

tautomers thereof, and pharmaceutically acceptable salts thereof.

Methods for treating kidney stones are also provided herein. The methods include administering a compound according to Formula I, Formula Ia, Formula Ib, Formula Ic, or Formula II as described above to a subject in need thereof.

GO inhibitors can be administered at any suitable dose in the methods of the invention. In general, a GO inhibitor will be administered at a dose ranging from about 0.1 milligrams to about 1000 milligrams per kilogram of a subject's body weight (i.e., about 0.1-1000 mg/kg). The dose of the GO inhibitor can be, for example, about 0.1-1000 mg/kg, or about 1-500 mg/kg, or about 25-250 mg/kg, or about 50-125 mg/kg. The dose of the GO inhibitor can be about 0.1-1 mg/kg, or about 1-50 mg/kg, or about 50-100 mg/kg, or about 100-150 mg/kg, or about 150-200 mg/kg, or about 200-250 mg/kg, or about 250-300 mg/kg, or about 350-400 mg/kg, or about 450-500 mg/kg, or about 500-550 mg/kg, or about 550-600 mg/kg, or about 600-650 mg/kg, or about 650-700 mg/kg, or about 700-750 mg/kg, or about 750-800 mg/kg, or about 800-850 mg/kg, or about 850-900 mg/kg, or about 900-950 mg/kg, or about 950-1000 mg/kg. The dose of the GO inhibitor can be about 1, 2, 3, 4, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 mg/kg. The GO inhibitor can be administered, orally, topically, parenterally, intravenously, intraperitoneally, intramuscularly, intralesionally, intranasally, subcutaneously, or intrathecally using a suitable vehicle, including any of the compositions described above. Alternatively, the GO inhibitor can be administered via a suppository or via implantation of a slow-release device, e.g., a mini-osmotic pump.

The dosages can be varied depending upon the requirements of the patient, the severity of the kidney stones and/or PH1 being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the kidney stones and/or PH1.

Administration of the GO inhibitor can be conducted for a period of time which will vary depending upon the nature of the particular disorder, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the disorder. The dosage of the GO-inhibitor can either be increased in the event the patient does not respond significantly to a particular dosage level, or the dose can be decreased if an alleviation of the symptoms is observed, or if unacceptable side effects are seen with a particular dosage. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be conducted, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the symptoms go into remission or generally improves, the dosage may be maintained or kept at lower than maximum amount. If kidney stones reappear or PH1 symptoms worsen, the first dosage regimen can be resumed until an improvement is seen, and the second dosing regimen can be implemented again. This cycle can be repeated multiple times as necessary.

VI. Examples

The following abbreviations are used in the examples below:
aq aqueous
bs broad singlet
CD$_3$OD methanol-d$_4$
CDCl$_3$ chloroform-d
conc. concentrated
CuSO$_4$ copper(II) sulfate
CV cartridge volume
DCM dichloromethane
DIPEA diisopropylethyl amine
DMF dimethylformamide
DMSO dimethylsulfoxide
Eq. equivalent
Et$_2$O diethylether
EA ethyl acetate EtOAc ethyl acetate
h hour(s)
Hex hexanes
HPLC high performance liquid chromatography
LRMS low resolution mass spec
M molar
MeOH methanol
min minute(s)
NaCl sodium chloride
$Na_2SO_4$ sodium sulfate
PMB paramethoxybenzyl
RBF round bottom flask
rt room temperature
$t_R$ retention time
satd. saturated
$SiO_2$ silica gel
THF tetrahydrofuran
TLC thin layer chromatography.

The compounds of this invention may be prepared in light of the specification using steps generally known to those of ordinary skill in the art. Those compounds may be analyzed by known methods, including but not limited to LC-MS (liquid chromatography mass spectrometry), HPLC (high performance liquid chromatography) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in the art in light of this specification for making the compounds of this invention. Unless otherwise indicated, all variables in the following Examples are as defined herein.

LRMS values were recorded on Waters micromass ZQ using direct injection of the samples in either methanol or acetonitrile. Analytical HPLC was carried out on Waters alliance using Agilent, Zorbax-SB-CN, 3.5 μm, 4.6×150 mm, mobile phase, acetonitrile in water (0 to 100%) contains ammonium acetate buffer; flow rate, 1.5 mL/min, run time, 20 min].

Example 1. Preparation of 5-(4-morpholinophenoxy)-1H-1,2,3-triazole-4-carboxylic Acid (8a)

Step 1: Methyl 5-hydroxy-1-(4-methoxybenzyl)-1H-1,2,3-triazole-4-carboxylate (3a). The title compound 3a was prepared as described for the ethyl ester analog 3b see: D. R. Buckle et al. J. Chem. Soc., Perkin Trans, I, 627 (1982). To MeOH (26 mL) was added portionwise sodium (0.348 g, 15.1 mmol) followed by dimethyl malonate 1a (2 g, 15.1 mmol). After 30 min, a solution of PMB-azide 2 (2.47 g, 15.1 mmol) in MeOH (3 mL) was added drop wise to the previous mixture. The mixture was gently heated at 75° C. for 18 hrs (light yellow-brown coloration). After the methanol was evaporated, 20 mL of water was added to the mixture and cooled with water ice bath and the pH set around 2 using 1 M HCl (15 mL). A solid was formed plus some waxy solid and the mixture was stirred in an ice bath. The mixture was sonicated for one hour then stirred again in ice bath to give a mixture at the bottom of the flask. The water was decanted and more water added to the mixture followed by decantation.

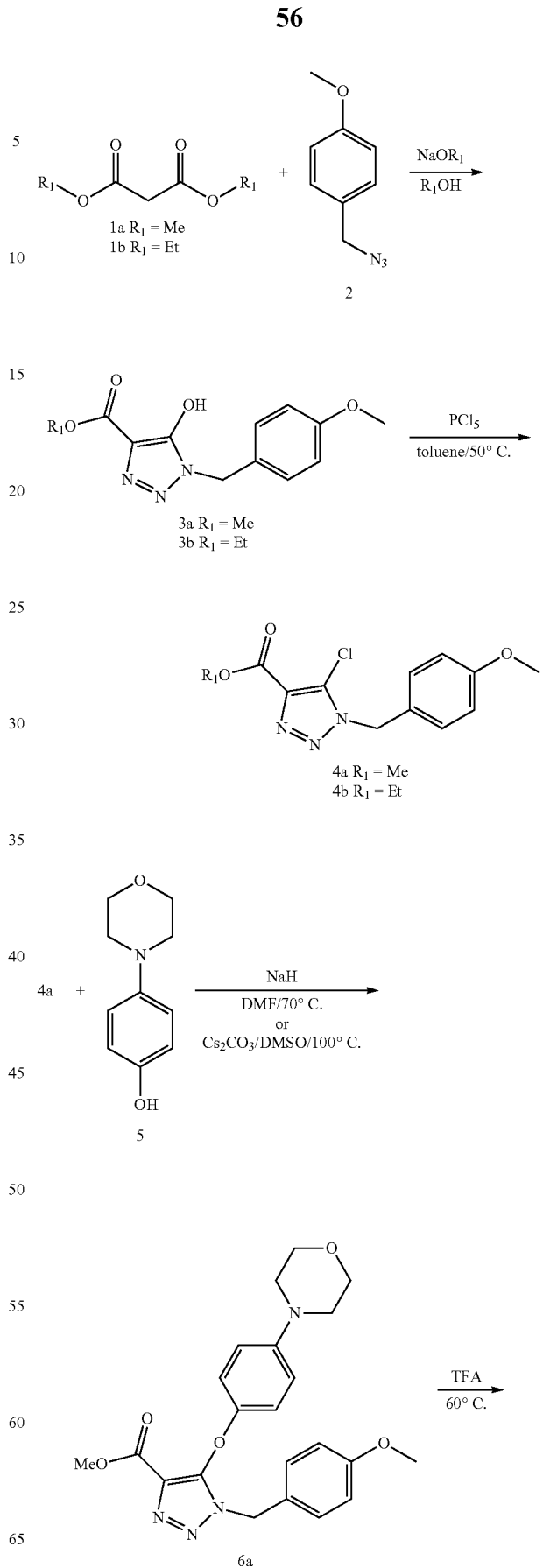

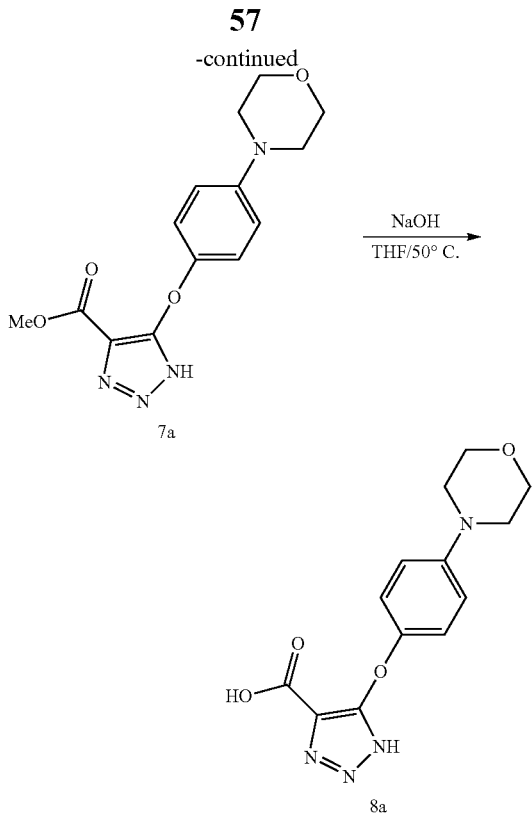

To the previous mixture was added EtOAc until total dissolution followed by evaporation under reduced pressure. To the resulting solid was added hexane followed by EtOAc to provide a cream solid which was filtered on a paper to give a the title compound 3a as a white solid (1.50 g, 5.69 mmol) (38%). ¹H NMR (400 MHz, CDCl₃) δ 7.29 (d, J=8.4 Hz, 2H), 6.84 (d, 8.4 Hz, 2H), 5.31 (s, 2H), 3.91 (s, 3H), 3.79 (s, 3H).

Step 2: Methyl 5-chloro-1-(4-methoxybenzyl)-1H-1,2,3-triazole-4-carboxylate (4a). The title compound 4a was prepared as described for the ethyl ester analog 4b. See: D. R. Buckle et al. J. Chem. Soc., Perkin Trans, I, 627 (1982). To a mixture of methyl 5-hydroxy-1-(4-methoxybenzyl)-1H-1,2,3-triazole-4-carboxylate 3a from step 1 (674 mg, 2.46 mmol) in toluene (7 mL) which was co-evaporated with toluene was added phosphorus pentachloride (577 mg, 2.77 mmol). The resulting mixture was heated at 40° C. until full dissolution (clear solution). The toluene was then evaporated and the mixture extracted with EtOAc and aq NaHCO₃. The organic phase was collected, dried over sodium sulfate, filtered and evaporated and the resulting yellow oil was used as such for the next step assuming quantitative yield (720 mg).

Step 3: Methyl 1-(4-methoxybenzyl)-5-(4-morpholinophenoxy)-1H-1,2,3-triazole-4-carboxylate (6a). Sodium hydride 60% (102 mg, 2.56 mmol) was added to 4-morpholin-4-yl-phenol 5 (458 mg, 2.56 mmol) in DMF (6 mL). After a period of 30 min at rt, was added a solution of methyl 5-chloro-1-(4-methoxybenzyl)-1H-1,2,3-triazole-4-carboxylate 4a from step 2 (720 mg, 2.56 mmol) in DMF. The resulting mixture was heated at 70° C. for two days (TLC 50/50 EA in hexane). The mixture was extracted with EtOAc-water, the organic phase was washed several time with water. The organic phase was collected and dried over sodium sulfate, filtered and evaporated. The mixture was purified on a 40 g silica gel column with 10% EtOAc in hexane to 50% EtOAc in hexane to provide the title compound 6a (240 mg, 0.566 mmol) (22%). ¹H NMR (400 MHz, acetone-d₆) δ 7.24 (d, J=8.8 Hz, 2H), 6.95-6.84 (m, 4H), 6.85-6.78 (m, 2H), 5.42 (s, 2H), 3.86-3.74 (m, 9H), 3.63 (s, 3H), 3.11-2.99 (m, 4H). MS: ES+ 446.86 (M+23)

Step 4: Methyl 5-(4-morpholinophenoxy)-1H-1,2,3-triazole-4-carboxylate 7a. To a solution of methyl 1-(4-methoxybenzyl)-5-(4-morpholinophenoxy)-1H-1,2,3-triazole-4-carboxylate 6a from step 3 (240 mg, 0.566 mmol) in TFA (5 mL) was heated at 60° C. for 1 hr and left at rt for 18 hrs. The mixture was extracted with EtOAc saturated sodium bicarbonate, dried over sodium sulfate, filtered and evaporated. The mixture was purified on a 24 g silica gel column with hexane to 100% EtOAc to provide the title compound 7a (160 mg, 0.526 mmol) (93%). ¹H NMR (400 MHz, acetone-d₆) δ 7.19-7.05 (m, 2H), 7.04-6.94 (m, 2H), 3.84 (s, 3H), 3.78 (m, 4H), 3.10 (m, 4H). MS: ES+ 304.9 (M+1).

Step 5: 5-(4-Morpholinophenoxy)-1H-1,2,3-triazole-4-carboxylic acid 8a. To a solution of methyl 5-(4-morpholinophenoxy)-1H-1,2,3-triazole-4-carboxylate 7a from step 4 (160 mg, 0.52 mmol) in THF (4 mL) was added 1 M sodium hydroxide (1.57 mL, 1.57 mmol). The reaction was heated at 50° C. for one day. The reaction mixture was extracted with EtOAc-THF and 1 M HCl, the organic phase was collected, dried over sodium sulfate, filtered and evaporated. The mixture was purified on a 12 g silica gel column with EtOAc to 5% MeOH in EA then 1% formic acid 10% MeOH in EtOAc. The desired fractions were evaporated and EA was added to the resulting solid followed by filtration to provide the title compound 8a (19 mg, 0.065 mmol) (12%). ¹H NMR (400 MHz, DMSO-d₆) δ 6.95 (2d, J=9.2 Hz, 4H), 3.82-3.64 (m, 4H), 3.09-2.92 (m, 4H). MS: ES+ 288.88 (M+1)

Example 2. Preparation of 5-(4-(piperazin-1-yl)phenoxy)-1H-1,2,3-triazole-4-carboxylic Acid (8b)

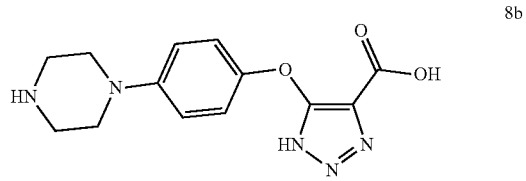 [SMILES: O=C(O)c1nn[nH]c1Oc1ccc(N2CCNCC2)cc1]

Step 1: tert-Butyl 4-(4-((1-(4-methoxybenzyl)-4-(methoxycarbonyl)-1H-1,2,3-triazol-5-yl)oxy)phenyl)piperazine-1-carboxylate (6b). Sodium hydride 60% (142 mg, 3.55 mmol) was added to 1-Boc-4-(4-hydroxy-phenyl)-piperazine (988 mg, 3.55 mmol) in DMF (9 mL). After a period of 30 min at rt, was added a solution of methyl 5-chloro-1-(4-methoxybenzyl)-1H-1,2,3-triazole-4-carboxylate 4a (1000 mg, 3.55 mmol) in DMF. The resulting mixture was heated at 70° C. for two days (TLC 50/50 EtOAc in hexane). The mixture was extracted with EtOAc-water, the organic phase was washed several time with water. The organic phase was dried over sodium sulfate, filtered and evaporated. The mixture was purified on a 40 g silica gel column with 10% EtOAc in hexane to 50% EtOAc in hexane to provide the title compound 6b (160 mg, 0.305 mmol) (9%). ¹H NMR (400 MHz, CDCl₃) δ 7.20 (d, J=8.6 Hz, 2H), 6.80 (dd, J=9.1, 4.8 Hz, 4H), 6.70 (d, J=9.2 Hz, 2H), 5.33 (s, 2H), 3.76 and 3.74 (2s, 6H), 3.57 (m, 4H), 3.04 (m, 4H), 1.64-1.25 (s, 9H).

Step 2: Methyl 5-(4-(piperazin-1-yl)phenoxy)-1H-1,2,3-triazole-4-carboxylate (7b). To a solution of tert-butyl 4-(4-((1-(4-methoxybenzyl)-4-(methoxycarbonyl)-1H-1,2,3-triazol-5-yl)oxy)phenyl)piperazine-1-carboxylate 6b from step 1 (160 mg, 0.305 mmol) in TFA (5 mL) was heated at 60° C. for 2 hrs and left at rt for 2 hrs. The mixture was evaporated and extracted with EtOAc-saturated sodium bicarbonate, dried over sodium sulfate, filtered and evaporated. The mixture was purified on a 12 g silica gel column with EtOAc to 70% MeOH in EtOAc to provide the title compound 7b (30 mg, 0.99 mmol) (32%). $^1$H NMR (400 MHz, CDCl$_3$) δ 7.09 (m, 2H), 6.88 (m, 24H), 3.89 (m, 3H), 3.10 (m, 4H), 3.04 (m, 4H).

Step 3: 5-(4-(Piperazin-1-yl)phenoxy)-1H-1,2,3-triazole-4-carboxylic acid (8b). To a solution of methyl 5-(4-(piperazin-1-yl)phenoxy)-1H-1,2,3-triazole-4-carboxylate 7b (30 mg, 0.10 mmol) in THF (4 mL) was added 1 M sodium hydroxide (0.3 mL, 0.3 mmol). The reaction was heated at 55° C. for 18 hrs. The THF was evaporated and the reaction mixture was acidified with 1 M HCl until pH 7. A solid was formed and filtered. The filtrate was treated with warm EtOAc and warm water. The EtOAc did not contain material and the water was evaporated to provide a white solid. To the solid was added water and the water decanted to remove the salts. The solid was dried on vacuum pump to provide the title compound 8b. $^1$H NMR (400 MHz, DMSO-d$_6$) δ 6.83 (s, 4H), 3.00 (m, 4H), 2.89 (m, 4H).

Example 3. Preparation of 5-(4-(4-acetylpiperazin-1-yl)phenoxy)-1H-1,2,3-triazole-4-carboxylic Acid (8c)

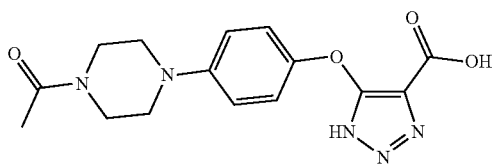

The title compound was prepared as described in previous example 1 and 2 except it was purified first on a 40 g C$_{1-8}$ silica gel reverse phase column isocratic 1% TFA in water to 100% ACN (compound elutes in 15% ACN) followed by purification on a 12 g silica gel with 100% EtOAc to 20% MeOH (containing 1% formic acid) in EtOAc. $^1$H NMR (400 MHz, CD$_3$OD) δ 7.02 (m, 4H), 3.68 (m, 4H), 3.13 (m, 4H), 2.07 (s, 3H).

Example 4. Preparation of 5-(4-(1H-pyrazol-1-yl)phenoxy)-1H-1,2,3-triazole-4-carboxylic Acid (8d)

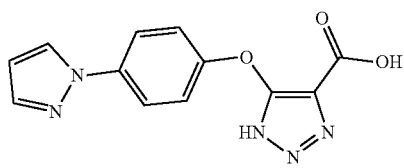

Step 1: Ethyl 5-(4-(1H-pyrazol-1-yl)phenoxy)-1-(4-methoxybenzyl)-1H-1,2,3-triazole-4-carboxylate (6d). In a seal tube, cesium carbonate (220 mg, 675 umol) was added to a stirred mixture of 4-(1H-pyrazol-1-yl)phenol (100 mg, 0.624 mmol) in DMSO (1.0 mL) at room temperature and under an argon atmosphere. After stirring for a period of 5 minutes, a solution of the ethyl 5-chloro-1-(4-methoxybenzyl)-1H-1,2,3-triazole-4-carboxylate 4b (230 mg, 0.700 mmol) was added. The glass vessel was tightly sealed and the mixture was heated at 100° C. for a period of 18 hours. After cooling to rt, water, brine and EtOAc were added to the reaction mixture. The phases were separated and the aqueous layer was extracted twice with EtOAc. The combined organic extracts were washed once with brine, dried over sodium sulfate, filtered and concentrated under reduced pressure. The crude product was taken up in DCM and was purified by flash chromatography on silica gel, eluting with DCM to 100% EtOAc to provide ethyl 5-(4-(1H-pyrazol-1-yl)phenoxy)-1-(4-methoxybenzyl)-1H-1,2,3-triazole-4-carboxylate (157 mg, 54%). $^1$H NMR (600 MHz, CDCl$_3$) δ 7.83 (s, 1H), 7.68 (s, 1H), 7.56 (d, J=8.6 Hz, 2H), 7.18 (d, J=8.3 Hz, 2H), 6.81 (d, J=8.4 Hz, 2H), 6.75 (d, J=8.3 Hz, 2H), 6.44 (s, 1H), 5.36 (s, 2H), 4.22-4.13 (m, 2H), 3.69 (s, 3H), 1.16-1.07 (m, 3H).

Step 2: Ethyl 5-(4-(1H-pyrazol-1-yl)phenoxy)-1H-1,2,3-triazole-4-carboxylate (7d). The title compound was prepared from ethyl 5-(4-(1H-pyrazol-1-yl)phenoxy)-1-(4-methoxybenzyl)-1H-1,2,3-triazole-4-carboxylate 6d as described in previous example 1 and 2. $^1$H NMR (600 MHz, CDCl$_3$) δ 7.89-7.84 (m, 1H), 7.82-7.78 (m, 1H), 7.68-7.62 (m, 2H), 7.30-7.22 (m, 2H), 6.52-6.43 (m, 1H), 4.45-4.33 (m, 2H), 1.36-1.29 (m, 3H). MS: ES+ 300.1 (M+1).

Step 3: 5-(4-(1H-Pyrazol-1-yl)phenoxy)-1H-1,2,3-triazole-4-carboxylic acid (8d). The title compound was prepared from ethyl 5-(4-(1H-pyrazol-1-yl)phenoxy)-1H-1,2,3-triazole-4-carboxylate 7d as described in previous example 1 and 2. $^1$H NMR (600 MHz, DMSO-d$_6$) δ 15.25 (brs, 1H), 13.26 (brs, 1H), 8.45 (d, J=2.4 Hz, 1H), 7.82 (d, J=9.0 Hz, 2H), 7.73 (d, J=1.4 Hz, 1H), 7.21 (d, J=9.0 Hz, 2H), 6.57-6.47 (m, 1H). MS: ES+272.0 (M+1).

Example 5. Preparation of 5-(2-bromophenoxy)-1H-1,2,3-triazole-4-carboxylic Acid (8e)

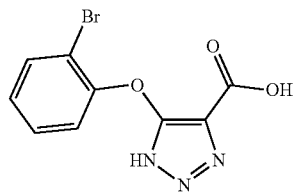

The compound was prepared as described in the previous example 1 and 2 using ethyl 5-chloro-1-(4-methoxybenzyl)-1H-1,2,3-triazole-4-carboxylate 4b. $^1$H NMR (400 MHz, CD$_3$OD) δ 7.63 (dd, J=8.0, 1.5 Hz, 1H), 7.31 (m, 1H), 7.07 (m, 2H). MS: ES− 283.95 (M−1).

Example 6. Preparation of 5-(4-bromophenoxy)-1H-1,2,3-triazole-4-carboxylic Acid (8f)

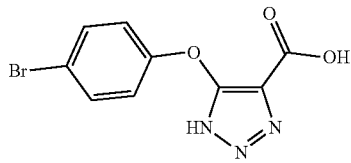

8f

The title compound was prepared as described in example 1 and 2 using either ethyl 5-chloro-1-(4-methoxybenzyl)-1H-1,2,3-triazole-4-carboxylate 4b or methyl 5-chloro-1-(4-methoxybenzyl)-1H-1,2,3-triazole-4-carboxylate 4a. $^1$H NMR (400 MHz, DMSO-d$_6$) δ 7.53 (m, 2H), 7.04 (m, 2H). MS: ES− 255.93 (M−1).

Example 7. Preparation of 5-(3-bromophenoxy)-1H-1,2,3-triazole-4-carboxylic Acid (8g)

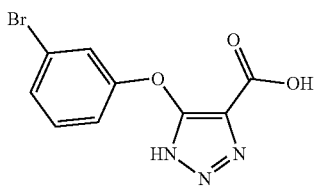

8g

The title compound was prepared as described in example 1 and 2 using ethyl 5-chloro-1-(4-methoxybenzyl)-1H-1,2,3-triazole-4-carboxylate 4b. $^1$H NMR (400 MHz, DMSO-d6) δ 7.37-7.28 (m, 3H), 7.09-7.04 (m, 1H)). MS: ES− 283.12 (M−1).

Example 8. Preparation of 5-(4-chloro-3-fluorophenoxy)-1H-1,2,3-triazole-4-carboxylic Acid (8h)

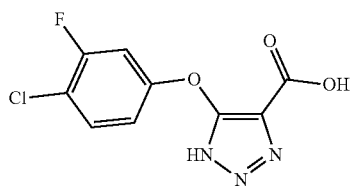

8h

The title compound was prepared as described in example 1 and 2 using ethyl 5-chloro-1-(4-methoxybenzyl)-1H-1,2,3-triazole-4-carboxylate 4b, except anisole (20 eq. was used at the PMB deprotection step. $^1$H NMR (400 MHz, DMSO-d$_6$) δ 7.56 (t, J=8.8 Hz, 1H), 7.28 (dd, J=10.5, 2.8 Hz, 1H), 6.97-6.92 (m, 1H).

Example 9. Preparation of 5-(4-fluorophenoxy)-1H-1,2,3-triazole-4-carboxylic Acid Sodium Salt (8i)

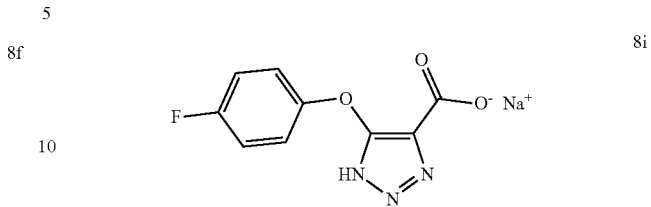

8i

Step 1: Methyl 5-(4-fluorophenoxy)-1-(4-methoxybenzyl)-1H-1,2,3-triazole-4-carboxylate. To a solution of methyl 5-chloro-1-(4-methoxybenzyl)-1H-1,2,3-triazole-4-carboxylate (4a, 0.16 g, 0.569 mmol) in THF (5 ml) were added Cs$_2$CO$_3$ (0.556 g, 1.707 mmol) and 4-fluorophenol (0.095 g, 0.853 mmol) at ambient temperature. The reaction mixture was heated at 70° C. for 16 h and then allowed to cool to ambient temperature. The resulting reaction mixture was poured in to water (50 ml) and extracted with EtOAc (3×50 ml). The combined organic phase was dried over Na$_2$SO$_4$, filtered and concentrated under reduced pressure. The resulting crude material was purified by column chromatography (21% Ethyl acetate in n-Hexane) yielding methyl 5-(4-fluorophenoxy)-1-(4-methoxybenzyl)-1H-1,2,3-triazole-4-carboxylate (0.063 g, 0.176 mmol). MS: ES+ 380 (M+23).

Step 2: Methyl 5-(4-fluorophenoxy)-1H-1,2,3-triazole-4-carboxylate. Deprotection was carried out as for Example 1, step 4, yielding methyl 5-(4-fluorophenoxy)-1H-1,2,3-triazole-4-carboxylate.

Step 3: 5-(4-Fluorophenoxy)-1H-1,2,3-triazole-4-carboxylic acid Na salt 8i. To a stirred solution of methyl 5-(4-fluorophenoxy)-1H-1,2,3-triazole-4-carboxylate (0.045 g, 0.189 mmol) in THF:water (4:1, 1.5 ml) was added NaOH (0.009 g, 0.208 mmol) at ambient temperature. The resulting reaction mixture was stirred at ambient temperature for 24 h. The reaction mixture was concentrated under reduced pressure and obtained material was triturated with dichloromethane:n-pentane (1:9, 2 ml). The resulting material was dried yielding 5-(4-fluorophenoxy)-1H-1,2,3-triazole-4-carboxylic acid Na salt 8i (0.045 g, 0.183 mmol). $^1$H NMR (400 MHz, DMSO-d6) δ ppm: 6.97-7.02 (m, 2H), 6.70-6.83 (m, 2H); MS: ES+ 224.0 (M+1).

Example 10. Preparation of 5-((4'-bromo-[1,1'-biphenyl]-4-yl)oxy)-1H-1,2,3-triazole-4-carboxylic Acid (8j)

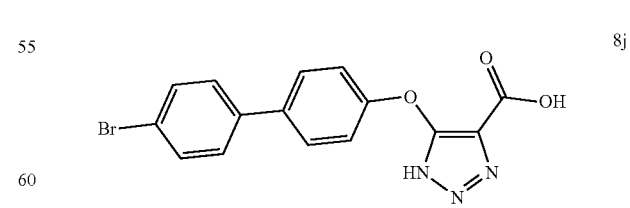

8j

The title compound was prepared as described in Example land 2 using ethyl 5-chloro-1-(4-methoxybenzyl)-1H-1,2,3-triazole-4-carboxylate 4b. $^1$H NMR (400 MHz, CD$_3$OD) δ 7.71-7.48 (m, 6H), 7.19 (d, J=8.8 Hz, 2H). MS: ES− 357.69 (M−1).

Example 11. Preparation of 5-(4-(1H-pyrazol-4-yl)phenoxy)-1H-1,2,3-triazole-4-carboxylic Acid (12a)

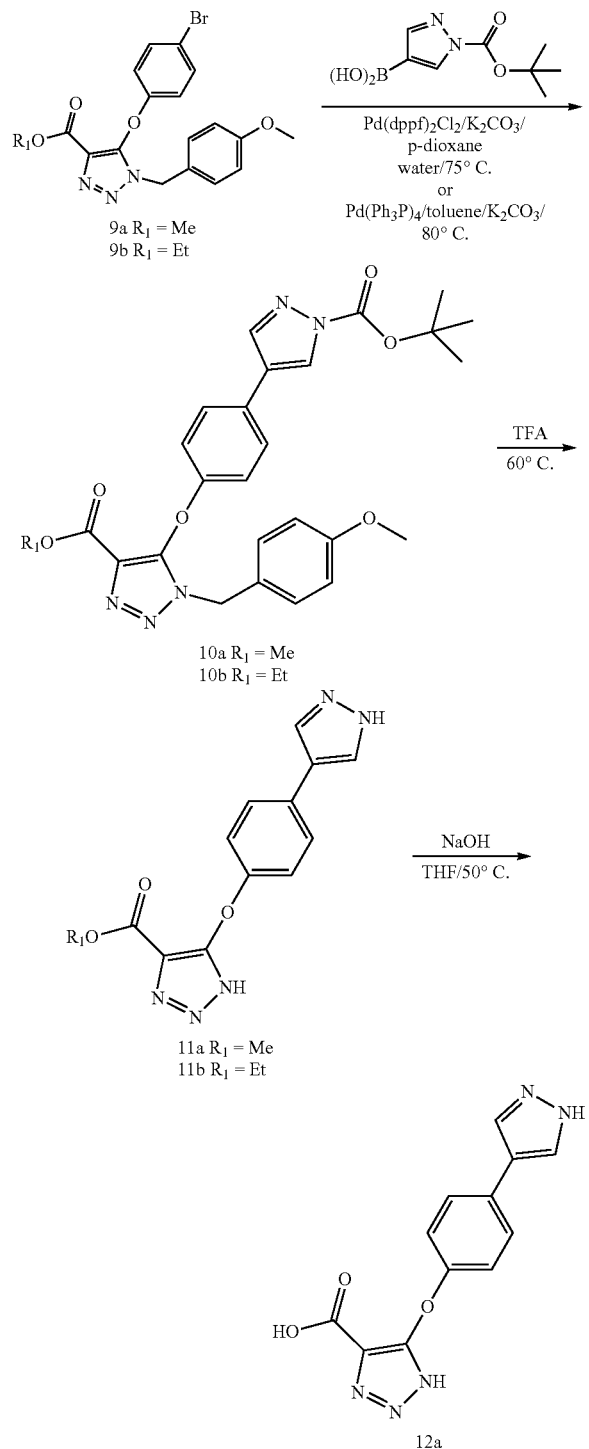

Step 1: Methyl 5-(4-(1-(tert-butoxycarbonyl)-1H-pyrazol-4-yl)phenoxy)-1-(4-methoxybenzyl)-1H-1,2,3-triazole-4-carboxylate (10a). To a mixture of methyl 5-(4-bromophenoxy)-1-(4-methoxybenzyl)-1H-1,2,3-triazole-4-carboxylate 9a prepared as described in example 6 (300 mg, 0.717 mmol), (1-(tert-butoxycarbonyl)-1H-pyrazol-4-yl)boronic acid (182 mg, 0.861 mmol), Pd(dppf)$_2$Cl$_2$ (29 mg, 0.035 mmol), potassium carbonate (297 mg, 2.15 mmol) in p-dioxane (3 mL) and water (0.3 mL) was heated at 75° C. for 2 hrs. The mixture was extracted with EtOAc-water, dried over sodium sulfate, filtered and evaporated. The mixture was purified on a 40 g silica gel column with hexane to 100% EtOAc to provide methyl 5-(4-(1-(tert-butoxycarbonyl)-1H-pyrazol-4-yl)phenoxy)-1-(4-methoxybenzyl)-1H-1,2,3-triazole-4-carboxylate 10a (170 mg, 0.340 mmol). $^1$H NMR (400 MHz, CDCl$_3$) δ 8.25 (s, 1H), 7.93 (s, 1H), 7.40 (d, J=8.9 Hz, 2H), 7.21 (d, J=8.7 Hz, 2H), 6.78 (m, 4H), 5.37 (s, 2H), 3.76 (2d, 6H), 1.68 (s, 9H).

Step 2: Methyl 5-(4-(1H-pyrazol-4-yl)phenoxy)-1H-1,2,3-triazole-4-carboxylate (11a). A solution of methyl 5-(4-(1-(tert-butoxycarbonyl)-1H-pyrazol-4-yl)phenoxy)-1-(4-methoxybenzyl)-1H-1,2,3-triazole-4-carboxylate 10a of step 1 (170 mg, 0.34 mmol) in TFA (5 mL) was heated at 60° C. for 2 hrs and left at rt for 2 hrs. The mixture was evaporated and extracted with EtOAc saturated sodium bicarbonate, dried over sodium sulfate, filtered and evaporated. To the mixture was added methanol to provide a solid which was filtered and washed with methanol to provide methyl 5-(4-(1H-pyrazol-4-yl)phenoxy)-1H-1,2,3-triazole-4-carboxylate 11a (25 mg, 0.09 mmol). The filtrate was purified on a 12 g silica gel column with hexane to 100% EtOAc (load with DCM) to provide additional material 14 mg (0.05 mmol) (41%). $^1$H NMR (400 MHz, DMSO-d$_6$) δ 12.91 (s, 1H), 8.15 (s, 1H), 7.88 (s, 1H), 7.78-7.41 (d, 2H), 7.34-6.80 (m, 2H), 3.76 (s, 3H). MS: ES+ 285.93 (M+1)

Step 3: 5-(4-(1H-Pyrazol-4-yl)phenoxy)-1H-1,2,3-triazole-4-carboxylic acid 12a. To a solution of methyl 4-(4-(1H-pyrazol-4-yl)phenoxy)-1H-1,2,3-triazole-5-carboxylate 11a step 2 (39 mg, 0.136 mmol) in THF (4 mL) was added 1 M sodium hydroxide (0.3 mL, 0.41 mmol). The reaction was heated at 55° C. for 18 hrs. The reaction mixture was partitioned between water and EtOAc followed by the addition of 1 M HCl 1 M. The compound remains in water therefore the water was evaporated to provide a white solid. To the solid was added 1 mL of water and the water decanted to remove the salts. This operation was repeated a second time. The material was dried on a vacuum pump to provide 5-(4-(1H-pyrazol-4-yl)phenoxy)-1H-1,2,3-triazole-4-carboxylic acid 12a (10 mg, 0.05 mmol) (27%) as a white solid. $^1$H NMR (400 MHz, DMSO-d$_6$) δ 7.94 (s, 2H), 7.47 (d, J=8.7 Hz, 2H), 6.85 (d, J=8.7 Hz, 2H).

Example 12. Preparation of 5-(4-(1H-pyrazol-5-yl)phenoxy)-1H-1,2,3-triazole-4-carboxylic Acid (12b)

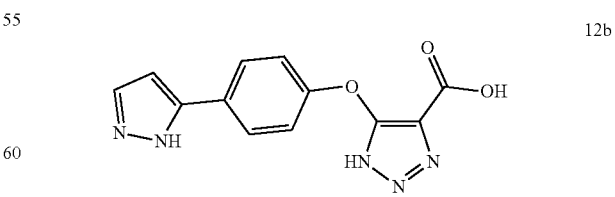

The title compound was prepared as described in Example 11. $^1$H NMR (400 MHz, DMSO-d$_6$) δ 7.76 (d, J=8.7 Hz, 2H), 7.68 (s, 1H), 7.08 (d, J=8.7 Hz, 2H), 6.65 (2s, 2H). MS: ES− 269.90 (M−1).

Example 13. Preparation of 5-(4-(2-methylpyrimidin-5-yl)phenoxy)-1H-1,2,3-triazole-4-carboxylic Acid (12c)

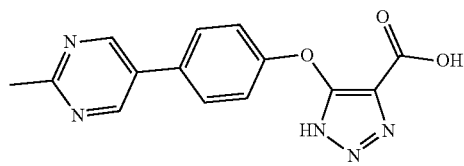

12c

The title compound was prepared as described in Example 11 using ethyl 5-(4-bromophenoxy)-1-(4-methoxybenzyl)-1H-1,2,3-triazole-4-carboxylate 9b as starting material. $^1$H NMR (400 MHz, DMSO-d6) δ 8.99 (s, 2H), 7.75 (m, 2H), 7.19 (d, J=8.8 Hz, 2H), 2.65 (s, 3H). MS: ES− 295.78 (M−1).

Example 14. Preparation of 5-(4-(pyridin-3-yl)phenoxy)-1H-1,2,3-triazole-4-carboxylic Acid (12d)

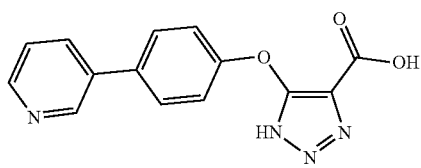

12d

The title compound was prepared as described in Example 11 using methyl 5-(4-bromophenoxy)-1-(4-methoxybenzyl)-1H-1,2,3-triazole-4-carboxylate 9a as starting material and Pd(Ph$_3$P)$_4$ in toluene-1M K$_2$CO$_3$ at 80° C. conditions for the cross coupling reaction. $^1$H NMR (600 MHz, DMSO-d6) δ 8.86 (m, 1H), 8.52 (m, 1H), 8.08 (m, 1H), 7.65 (m, 2H), 7.48 (m, 1H), 7.04 (m, 2H).

Example 15. Preparation of 5-((4'-(pyridin-4-yl)-[1,1'-biphenyl]-4-yl)oxy)-1H-1,2,3-triazole-4-carboxylic Acid (12e)

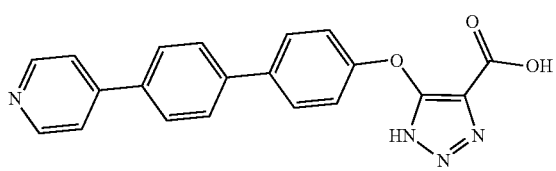

12e

The title compound was prepared as described in Example 11 using the PMB protected ethyl ester intermediate of Example 10. $^1$H NMR (400 MHz, DMSO-d$_6$) δ 8.64 (d, J=4.7 Hz, 2H), 7.90 (d, J=8.4 Hz, 2H), 7.81-7.66 (m, 6H), 7.17 (d, J=8.7 Hz, 2H). MS: ES+ 358.90 (M+1).

Example 16. Preparation of 5-((3"-(difluoromethoxy)-[1,1':4',1"-terphenyl]-4-yl)oxy)-1H-1,2,3-triazole-4-carboxylic Acid (12f)

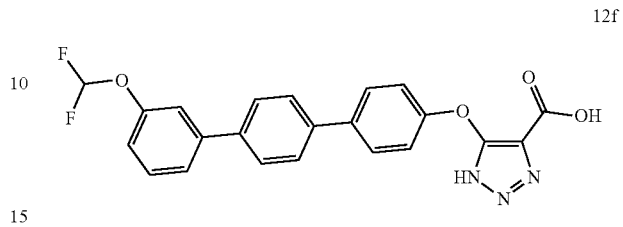

12f

The title compound was prepared as described in Example 11 using the PMB protected ethyl ester intermediate of Example 10. $^1$H NMR (400 MHz, DMSO-d$_6$) δ 7.82-7.68 (m, 6H), 7.62-7.57 (m, 1H), 7.55-7.47 (m, 2H), 7.34 (t, J=61.8 Hz, 1H), 7.19-7.12 (m, 3H). MS: ES+ 423.99 (M+1).

Example 17. Preparation of 5-((4"-(difluoromethoxy)-[1,1':4',1"-terphenyl]-4-yl)oxy)-1H-1,2,3-triazole-4-carboxylic Acid (12g)

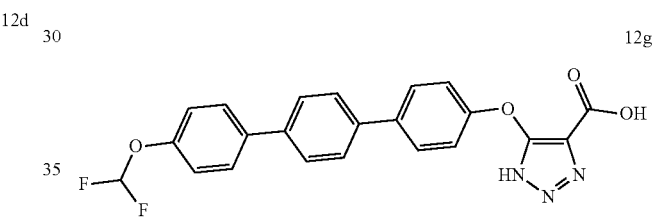

12g

The title compound was prepared as described in Example 11 using the PMB protected ethyl ester intermediate of Example 10. $^1$H NMR (400 MHz, DMSO-d$_6$) δ 7.81-7.67 (m, 8H), 7.29 (t, J=74.1 Hz, 1H), 7.27 (d, J=8.7 Hz, 2H), 7.16 (d, J=8.8 Hz, 2H). MS: ES− 422.00 (M−1).

Example 18. Preparation of 5-(4-(2-fluoropyridin-3-yl)phenoxy)-1H-1,2,3-triazole-4-carboxylic Acid (12h)

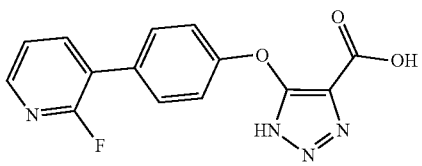

12h

The title compound was prepared as described in Example 11 using methyl 5-(4-bromophenoxy)-1-(4-methoxybenzyl)-1H-1,2,3-triazole-4-carboxylate 9a as starting material and K$_3$PO$_4$ as a base for the cross coupling reaction. $^1$H NMR (600 MHz, DMSO) δ 15.29 (brs, 1H), 13.22 (brs, 1H), 8.23 (s, 1H), 8.11 (t, J=8.5 Hz, 1H), 7.62 (d, J=7.9 Hz, 2H), 7.46 (s, 1H), 7.20 (d, J=8.1 Hz, 2H). MS: ES− 298.9 (M−1).

Example 19. Preparation of 5-(4-(pyridin-4-yl)phenoxy)-1H-1,2,3-triazole-4-carboxylic Acid (12i)

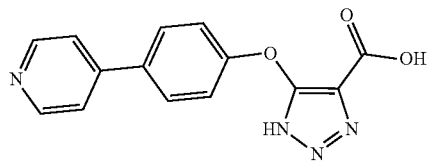

12i

The title compound was prepared as described in Example 11 using methyl 5-(4-bromophenoxy)-1-(4-methoxybenzyl)-1H-1,2,3-triazole-4-carboxylate 9a as starting material and K$_3$PO$_4$ as a base for the cross coupling reaction. $^1$H NMR (600 MHz, DMSO-d$_6$) δ 15.44 (brs, 1H), 13.27 (brs, 1H), 8.62 (d, J=4.8 Hz, 2H), 7.83 (d, J=8.6 Hz, 2H), 7.70 (d, J=4.4 Hz, 2H), 7.20 (d, J=8.6 Hz, 2H). MS: ES− 280.8 (M−1).

Example 20. Preparation of 5-((3'-cyano-[1,1'-biphenyl]-4-yl)oxy)-1H-1,2,3-triazole-4-carboxylic Acid (12j)

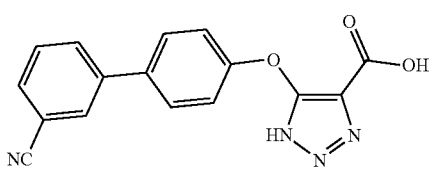

12j

The title compound was prepared as described in Example 11 using methyl 5-(4-bromophenoxy)-1-(4-methoxybenzyl)-1H-1,2,3-triazole-4-carboxylate 9a as starting material and Pd(Ph$_3$P)$_4$ for the cross coupling reaction. $^1$H NMR (600 MHz, Acetone-d$_6$) δ 8.05 (s, 1H), 7.99 (d, J=7.7 Hz, 1H), 7.79-7.72 (m, 3H), 7.67 (t, J=7.8 Hz, 1H), 7.28 (d, J=8.4 Hz, 2H). MS: ES− 305.0 (M−1).

Example 21. Preparation of 5-(4-(1-cyclobutyl-1H-pyrazol-4-yl)phenoxy)-1H-1,2,3-triazole-4-carboxylic Acid (12k)

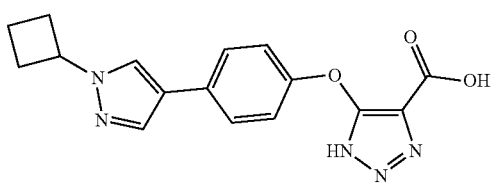

12k

The title compound was prepared as described in Example 11 using ethyl 5-(4-bromophenoxy)-1-(4-methoxybenzyl)-1H-1,2,3-triazole-4-carboxylate 9b as starting material and the boronate ester for the Suzuki reaction. $^1$H NMR (400 MHz, DMSO-d$_6$) δ 8.22 (s, 1H), 7.84 (s, 1H), 7.58-7.51 (m, 2H), 7.05 (d, J=8.8 Hz, 2H), 4.82 (m, 1H), 2.40 (m, 4H), 1.78 (m, 2H).

Example 22. Preparation of 5-((4'-methoxy-[1,1'-biphenyl]-4-yl)oxy)-1H-1,2,3-triazole-4-carboxylic Acid (12l)

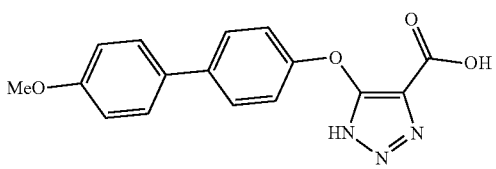

12l

The title compound was prepared as described in Example 11 using ethyl 5-(4-bromophenoxy)-1-(4-methoxybenzyl)-1H-1,2,3-triazole-4-carboxylate 9b as starting material. $^1$H NMR (400 MHz, DMSO-d$_6$) δ 7.61-7.52 (m, 4H), 7.10 (d, J=8.8 Hz, 2H), 6.99 (d, J=8.8 Hz, 2H), 3.77 (s, 3H). MS: ES− 310 (M−1).

Example 23. Preparation of 5-(4-(thiophen-3-yl)phenoxy)-1H-1,2,3-triazole-4-carboxylic Acid (12m)

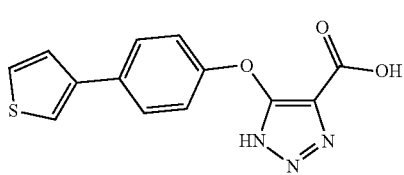

12m

The title compound was prepared as described in Example 11 using ethyl 5-(4-bromophenoxy)-1-(4-methoxybenzyl)-1H-1,2,3-triazole-4-carboxylate 9b as starting material except anisole (20 eq.) was used at the PMB deprotection step. $^1$H NMR (400 MHz, DMSO-d$_6$) δ 7.80 (dd, J=2.9, 1.4 Hz, 1H), 7.72-7.67 (m, 2H), 7.62 (dd, J=5.0, 2.9 Hz, 1H), 7.51 (dd, J=5.0, 1.3 Hz, 1H), 7.09 (d, J=8.8 Hz, 2H). MS: ES− 286 (M−1).

Example 24. Preparation of 5-(4-(pyrimidin-5-yl)phenoxy)-1H-1,2,3-triazole-4-carboxylic Acid (16a)

Step 1: Ethyl 1-(4-methoxybenzyl)-5-(4-(4,4,5,5-tetramethyl-1,3,2-dioxaborolan-2-yl)phenoxy)-1H-1,2,3-triazole-4-carboxylate (13b). To a mixture of ethyl 5-(4-bromophenoxy)-1-(4-methoxybenzyl)-1H-1,2,3-triazole-4-carboxylate 9b (3.00 g, 6.94 mmol), bis(pinacolato)diboron (1.85 g, 7.29 mmol), potassium acetate (1.36 g, 13.90 mmol), Pd(dppf)$_2$Cl$_2$ (283 mg, 0.334 mmol) in dioxane (50 mL) was degassed and stirred at 90° C. After a period of 18 hrs, additional bis(pinacolato)diboron (0.352 g, 1.39 mmol), potassium acetate (0.272 g, 2.78 mmol), and Pd(dppf)$_2$Cl2 and p-dioxane (5 mL) were added and the mixture degassed. After a period of 4 hrs, the reaction mixture was diluted with water and extracted with ethylacetate. The organic phase was dried over sodium sulfate, filtered and evaporated. The mixture was purified on a 80 g silica gel column using 100% hexane to 60% ethyl acetate in hexane to afford ethyl 1-(4-methoxybenzyl)-5-(4-(4,4,5,5-tetramethyl-1,3,2-dioxaborolan-2- yl)phenoxy)-1H-1,2,3-triazole-4-carboxylate 13b (2.50 g, 5.21 mmol) (75%). $^1$H NMR (400 MHz, CDCl$_3$) δ 7.71 (d, J=8.7 Hz, 2H), 7.18 (d, J=8.7 Hz, 2H), 6.75 (m, 4H), 5.29 (s, 2H), 4.15 (m, 2H), 3.76 (m, 3H), 1.35 (m, 12H), 1.14 (m, 3H).

Step 2: Ethyl 1-(4-methoxybenzyl)-5-(4-(pyrimidin-5-yl)phenoxy)-1H-1,2,3-triazole-4-carboxylate (14b). The title compound was prepared as described in Example 11 step 1 except K$_3$PO$_4$ was used as a base. $^1$H NMR (400 MHz, CDCl$_3$) δ 8.97 (d, J=1.5 Hz, 1H), 8.68-8.54 (m, 1H), 8.51 (d, J=2.5 Hz, 1H), 7.94 (d, J=8.9 Hz, 2H), 7.22 (d, J=8.7 Hz, 2H), 6.89 (d, J=8.9 Hz, 2H), 6.77 (d, J=8.7 Hz, 2H), 5.39 (s, 2H), 4.20 (m, 2H), 3.74 (s, 3H), 1.12 (t, J=7.1 Hz, 3H). MS: ES+ 453.87 (M+23).

Step 3: 5-(4-(pyrimidin-5-yl)phenoxy)-1H-1,2,3-triazole-4-carboxylic acid (16a). The title compound was prepared from ethyl 1-(4-methoxybenzyl)-5-(4-(pyrimidin-5-yl)phenoxy)-1H-1,2,3-triazole-4-carboxylate 14b as described in Example 11 step 2 and step 3 except the TFA reaction was run at rt. $^1$H NMR (400 MHz, DMSO-d$_6$) δ 9.23 (d, J=1.5 Hz, 1H), 8.69 (dd, J=2.5, 1.6 Hz, 1H), 8.58 (d, J=2.5 Hz, 1H), 8.15 (m, 2H), 7.20 (d, J=8.9 Hz, 2H). MS: ES− 281.86 (M−1).

Example 25. Preparation of 5-(4-(thiazol-2-yl)phenoxy)-1H-1,2,3-triazole-4-carboxylic Acid (16b)

The title compound was prepared as described in Example 24 using K$_2$CO$_3$ as a base for the cross coupling reaction. $^1$H NMR (400 MHz, DMSO-d$_6$) δ 7.93 (d, J=8.7 Hz, 2H), 7.89 (d, J=3.1 Hz, 1H), 7.75 (d, J=3.2 Hz, 1H), 7.16 (d, J=8.7 Hz, 2H). MS: ES− 286.96 (M−1).

Example 26. Preparation of 5-(4-(oxazol-2-yl)phenoxy)-1H-1,2,3-triazole-4-carboxylic Acid (16c)

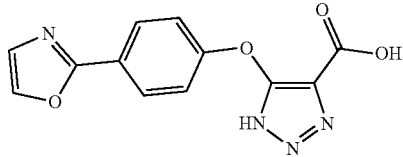

16c

The title compound was prepared as described in Example 24 using K₂CO₃ as a base for the cross coupling reaction and the PMB deprotection was performed at 50° C. ¹H NMR (400 MHz, DMSO-d₆) δ 8.19 (d, J=0.8 Hz, 1H), 7.96 (d, J=9.0 Hz, 2H), 7.35 (d, J=0.8 Hz, 1H), 7.18 (d, J=8.9 Hz, 2H).

Example 27. Preparation of 5-(4-(imidazo[1,2-a]pyridin-6-yl)phenoxy)-1H-1,2,3-triazole-4-carboxylic Acid (16d)

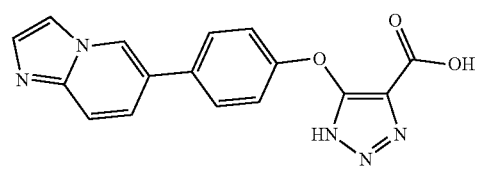

16d

The title compound was prepared as described in Example 26. ¹H NMR (400 MHz, DMSO-d₆) δ 9.09 (s, 1H), 8.13 (s, 1H), 7.98-7.79 (m, 3H), 7.73 (d, J=8.6 Hz, 2H), 7.22 (d, J=8.6 Hz, 2H).

Example 28. Preparation of 5-((2'-(difluoromethoxy)-[1,1'-biphenyl]-4-yl)oxy)-1H-1,2,3-triazole-4-carboxylic Acid (16e)

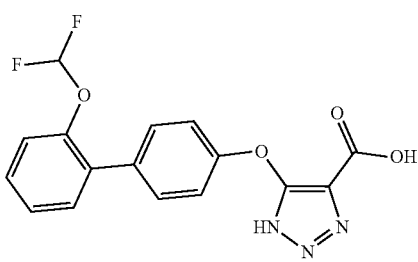

16e

The title compound was prepared as described in Example 26. ¹H NMR (400 MHz, DMSO) δ 7.48-7.39 (m, 4H), 7.35-7.25 (m, 2H), 7.16-7.11 (m, 3H). MS: ES+ 369.98 (M+23).

Example 29. Preparation of 5-((4'-cyano-[1,1'-biphenyl]-4-yl)oxy)-1H-1,2,3-triazole-4-carboxylic Acid (12n)

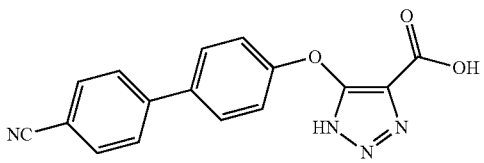

12n

The title compound was prepared as described in Example 11 using methyl 5-(4-bromophenoxy)-1-(4-methoxybenzyl)-1H-1,2,3-triazole-4-carboxylate 9a as starting material and Pd(Ph₃P)₄ in toluene-1M K₂CO₃ at 80° C. conditions for the cross coupling reaction. ¹H NMR (600 MHz, DMSO-d₆) δ 7.90 (m, 4H), 7.77 (m, 2H), 7.19 (m, 2H). MS: ES– 305.1 (M–1).

Example 30. Preparation of 5-((4'-carbamoyl-[1,1'-biphenyl]-4-yl)oxy)-1H-1,2,3-triazole-4-carboxylic Acid (12o)

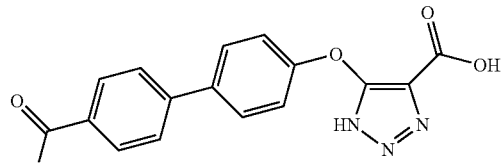

12o

The title compound was prepared as described in Example 11 using methyl 5-(4-bromophenoxy)-1-(4-methoxybenzyl)-1H-1,2,3-triazole-4-carboxylate 9a as starting material and Pd(Ph₃P)₄ in toluene-1M K₂CO₃ at 80° C. conditions for the cross coupling reaction. ¹H NMR (600 MHz, DMSO-d₆) δ 7.99 (m, 2H), 7.63 (m, 2H), 7.14 (m, 2H). MS: ES– 323.8 (M–1).

Example 31. Preparation of 5-((4'-methyl-[1,1'-biphenyl]-4-yl)oxy)-1H-1,2,3-triazole-4-carboxylic Acid (12p)

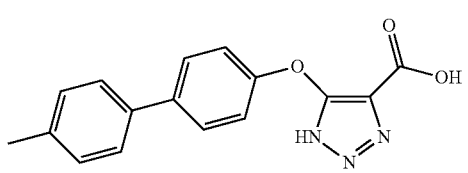

12p

The title compound was prepared as described in Example 11 using ethyl 5-(4-bromophenoxy)-1-(4-methoxybenzyl)-1H-1,2,3-triazole-4-carboxylate 9b as starting material. ¹H NMR (400 MHz, DMSO-d₆) δ 7.64-7.58 (m, 2H), 7.51 (d, J=8.2 Hz, 2H), 7.24 (d, J=7.9 Hz, 2H), 7.14-7.09 (m, 2H), 2.31 (s, 3H).

Example 32. Preparation of 5-((4'-isopropyl-[1,1'-biphenyl]-4-yl)oxy)-1H-1,2,3-triazole-4-carboxylic Acid (12q)

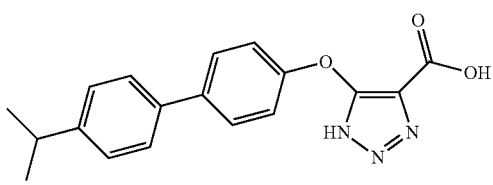

The title compound was prepared as described in Example 11 using ethyl 5-(4-bromophenoxy)-1-(4-methoxybenzyl)-1H-1,2,3-triazole-4-carboxylate 9b as starting material. $^1$H NMR (400 MHz, DMSO-$d_6$) δ 7.63-7.58 (m, 2H), 7.53 (d, J=8.3 Hz, 2H), 7.30 (d, J=8.2 Hz, 2H), 7.15-7.10 (m, 2H), 2.90 (m, 1H), 1.21 (d, J=6.9 Hz, 6H). MS: ES– 322.07 (M–1).

Example 33. Preparation of 5-((3'-chloro-4'-fluoro-[1,1'-biphenyl]-4-yl)oxy)-1H-1,2,3-triazole-4-carboxylic Acid (12r)

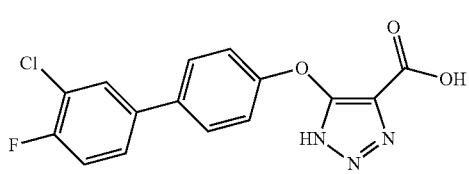

The title compound was prepared as described in Example 11 using ethyl 5-(4-bromophenoxy)-1-(4-methoxybenzyl)-1H-1,2,3-triazole-4-carboxylate 9b as starting material except anisole (20 eq.) was used at PMB deprotection step. $^1$H NMR (400 MHz, DMSO-$d_6$) δ 7.85 (m, 1H), 7.70-7.62 (m, 3H), 7.50-7.44 (m, 1H), 7.15-7.10 (m, 2H). MS: ES– 331.98 (M–1).

Example 34. Preparation of 5-((2',3'-difluoro-[1,1'-biphenyl]-4-yl)oxy)-1H-1,2,3-triazole-4-carboxylic Acid (12s)

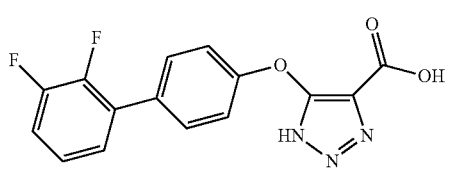

The title compound was prepared as described in Example 11 using ethyl 5-(4-bromophenoxy)-1-(4-methoxybenzyl)-1H-1,2,3-triazole-4-carboxylate 9b as starting material except anisole (20 eq.) was used at the deprotection step. $^1$H NMR (400 MHz, DMSO-$d_6$) δ 7.56 (m, 2H), 7.46-7.24 (m, 3H), 7.20-7.15 (m, 2H). MS: ES-1 315.99 (M–1).

Example 35. Preparation of 5-((4'-(tert-butyl)-[1,1'-biphenyl]-4-yl)oxy)-1H-1,2,3-triazole-4-carboxylic Acid (12t)

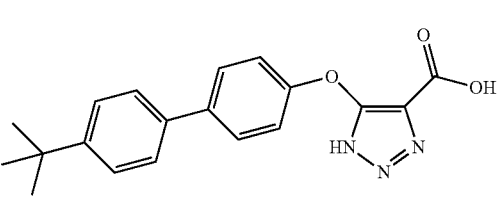

The title compound was prepared as described in Example 11 using ethyl 5-(4-bromophenoxy)-1-(4-methoxybenzyl)-1H-1,2,3-triazole-4-carboxylate 9b as starting material except anisole (20 eq.) was used at the deprotection step. $^1$H NMR (400 MHz, DMSO-$d_6$) δ 7.65-7.59 (m, 2H), 7.57-7.51 (m, 2H), 7.48-7.42 (m, 2H), 7.12 (d, J=8.7 Hz, 2H), 1.29 (s, 9H).

Example 36. Preparation of 5-(4-chlorophenoxy)-1H-1,2,3-triazole-4-carboxylic Acid (8k)

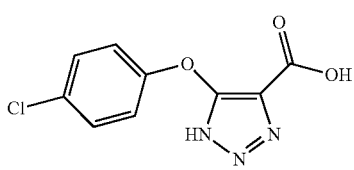

The compound was prepared as described in the previous Example 1 and 2. $^1$H NMR (400 MHz, DMSO-$d_6$) δ 7.56-7.28 (m, 2H), 7.15-7.00 (m, 2H). MS: ES– 237.99 (M–1).

Example 37. Preparation of 5-(4-(pyrazin-2-yl)phenoxy)-1H-1,2,3-triazole-4-carboxylic Acid (16f)

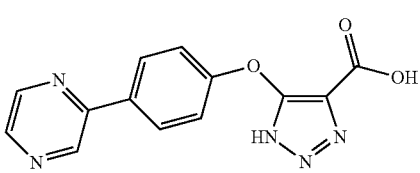

The title compound was prepared as described in Example 24 using $K_2CO_3$ as a base for the cross coupling reaction. $^1$H NMR (400 MHz, DMSO-$d_6$) δ 9.23 (d, J=1.5 Hz, 1H), 8.69 (dd, J=2.5, 1.6 Hz, 1H), 8.58 (d, J=2.5 Hz, 1H), 8.15 (m, 2H), 7.20 (d, J=8.9 Hz, 2H). MS: ES– 281.86 (M–1).

Example 38. Preparation of 5-((4'-(trifluoromethyl)-[1,1'-biphenyl]-4-yl)oxy)-1H-1,2,3-triazole-4-carboxylic Acid (12u)

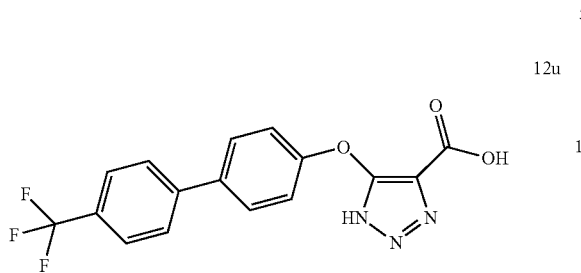

12u

The title compound was prepared as described in Example 11 using ethyl 5-(4-bromophenoxy)-1-(4-methoxybenzyl)-1H-1,2,3-triazole-4-carboxylate 9b as starting material. $^1$H NMR (400 MHz, DMSO-$d_6$) δ 7.86 (d, J=8.2 Hz, 2H), 7.79 (d, J=8.4 Hz, 2H), 7.75-7.71 (m, 2H), 7.21-7.15 (m, 2H). MS: ES+ 349.96 (M+1).

Example 39. Preparation of 5-((4'-(difluoromethoxy)-[1,1'-biphenyl]-4-yl)oxy)-1H-1,2,3-triazole-4-carboxylic Acid (12v)

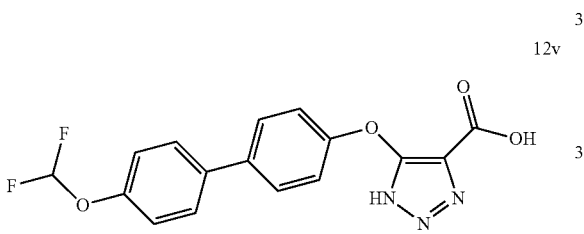

12v

The title compound was prepared as described in Example 11 using ethyl 5-(4-bromophenoxy)-1-(4-methoxybenzyl)-1H-1,2,3-triazole-4-carboxylate 9b as starting material. $^1$H NMR (400 MHz, DMSO-$d_6$) δ 7.64 (d, J=8.8 Hz, 2H), 7.54 (d, J=8.7 Hz, 2H), 7.27-7.17 (m, 3H), 6.92 (d, J=8.7 Hz, 2H). MS: ES− 345.93 (M−1).

Example 40. Preparation of 5-((3'-(difluoromethoxy)-[1,1'-biphenyl]-4-yl)oxy)-1H-1,2,3-triazole-4-carboxylic Acid (16g)

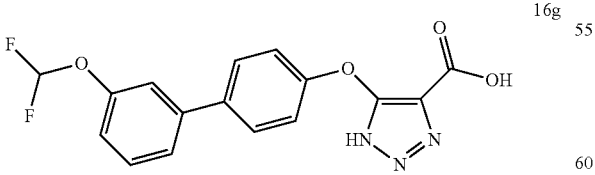

16g

The title compound was prepared as described in Example 24 using $K_2CO_3$ as a base for the cross coupling reaction. $^1$H NMR (400 MHz, DMSO-$d_6$) δ 7.68 (d, J=8.8 Hz, 2H), 7.49 (m, 2H), 7.41 (s, 1H), 7.33 (s, 1H), 7.13 (d, J=8.8 Hz, 3H). m/z 345.79 (M−1).

Example 41. Preparation of 5-(4-(furan-3-yl)phenoxy)-1H-1,2,3-triazole-4-carboxylic Acid (12x)

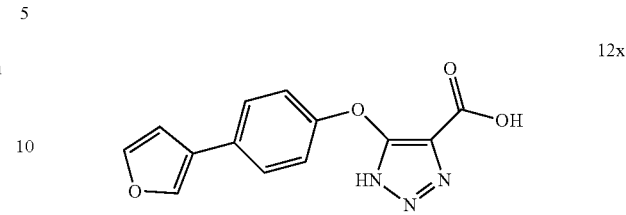

12x

The title compound was prepared as described in Example 11 using ethyl 5-(4-bromophenoxy)-1-(4-methoxybenzyl)-1H-1,2,3-triazole-4-carboxylate 9b as starting material and the addition of anisole for the PMB deprotection. $^1$H NMR (400 MHz, DMSO-$d_6$) δ 8.12 (s, 1H), 7.71 (t, J=1.7 Hz, 1H), 7.60-7.55 (m, 2H), 7.07 (d, J=8.8 Hz, 2H), 6.93-6.89 (m, 1H).

Example 42. Preparation of 5-([1,1'-biphenyl]-4-yloxy)-1H-1,2,3-triazole-4-carboxylic Acid (8l)

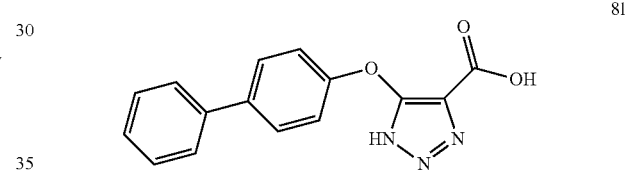

8l

The compound was prepared as described in the previous example 1 and 2 using methyl 5-chloro-1-(4-methoxybenzyl)-1H-1,2,3-triazole-4-carboxylate 4a and anisole for the PMB deprotection. $^1$H NMR (400 MHz, DMSO-$d_6$) δ 7.67-7.60 (m, 4H), 7.44 (dd, J=10.4, 4.8 Hz, 2H), 7.34 (dt, J=9.2, 4.3 Hz, 1H), 7.16-7.11 (m, 2H).

Example 43. Preparation of 5-(p-tolyloxy)-1H-1,2,3-triazole-4-carboxylic Acid (8m)

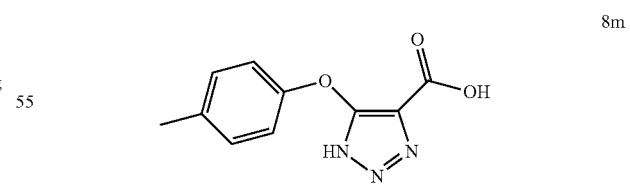

8m

The title compound was prepared as described in the previous example 1 and 2 using methyl 5-chloro-1-(4-methoxybenzyl)-1H-1,2,3-triazole-4-carboxylate 4a and anisole for the PMB deprotection. $^1$H NMR (400 MHz, DMSO-$d_6$) δ 7.14 (d, J=8.2 Hz, 2H), 6.94 (d, J=8.3 Hz, 2H), 2.26 (s, 3H).

Example 44. Preparation of 5-((6-(3-(difluoromethoxy)phenyl)pyridin-3-yl)oxy)-1H-1,2,3-triazole-4-carboxylic Acid (12y)

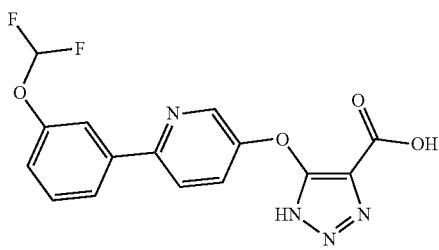

12y

The title compound was prepared as described in Example 11 except using ethyl 5-((6-chloropyridin-3-yl)oxy)-1-(4-methoxybenzyl)-1H-1,2,3-triazole-4-carboxylate for the cross coupling reaction. The ethyl 5-((6-chloropyridin-3-yl)oxy)-1-(4-methoxybenzyl)-1H-1,2,3-triazole-4-carboxylate was prepared as described in Example 6 from ethyl 5-chloro-1-(4-methoxybenzyl)-1H-1,2,3-triazole-4-carboxylate 4b and 6-chloropyridin-3-ol. For the PMB deprotection anisole was added to the reaction mixture. $^1$H NMR (400 MHz, DMSO-$d_6$) δ 8.56 (d, J=2.8 Hz, 1H), 8.03 (d, J=8.8 Hz, 1H), 7.91 (d, J=8.0 Hz, 1H), 7.84 (s, 1H), 7.66 (dd, J=8.8, 2.8 Hz, 1H), 7.53 (t, J=7.5 Hz, 1H), 7.33 (t, J=73.5 Hz, 1H), 7.22 (dd, J=8.0, 1.8 Hz, 1H). MS: ES+ 349.10 (M+1).

Example 45. Preparation of 5-phenoxy-1H-1,2,3-triazole-4-carboxylic Acid (8n)

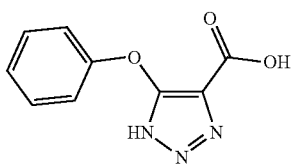

8n

The title compound was prepared from 5-(4-chlorophenoxy)-1H-1,2,3-triazole-4-carboxylic acid 8k of Example 36 by treatment with Pd/C in MeOH under 1 atm of hydrogen. The resulting methyl ester was hydrolyzed as described in example 1 and 2. $^1$H NMR (400 MHz, DMSO-$d_6$) δ 7.44-7.29 (m, 2H), 7.13 (t, J=7.4 Hz, 1H), 7.06-6.97 (m, 2H). MS: ES– 204.08 (M–1).

Example 46. Preparation of 5-(4-methoxyphenoxy)-1H-1,2,3-triazole-4-carboxylic Acid (8o)

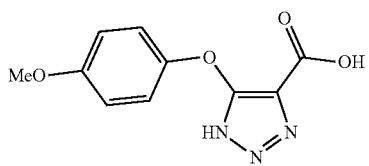

8o

The title compound was prepared as described in the previous Example 1 and 2 using methyl 5-chloro-1-(4-methoxybenzyl)-1H-1,2,3-triazole-4-carboxylate 4a and anisole for the PMB deprotection. $^1$H NMR (400 MHz, DMSO-$d_6$) δ 7.07-7.00 (m, 2H), 6.94-6.87 (m, 2H), 3.72 (s, 3H). MS: ES+ 258.07 (M+23).

Example 47. Preparation of 5-((4-fluorophenyl)thio)-1H-1,2,3-triazole-4-carboxylic Acid (8p)

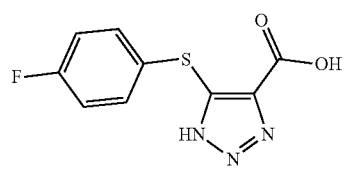

8p

The title compound was prepared as described in the previous example 1 and 2 using 4-fluorothiophenol for the addition on methyl 5-chloro-1-(4-methoxybenzyl)-1H-1,2,3-triazole-4-carboxylate 4a and anisole for the PMB deprotection. $^1$H NMR (400 MHz, DMSO-$d_6$) δ 7.55 (s, 2H), 7.24 (t, J=8.8 Hz, 2H). MS: ES+ 262.03 (M+23).

Example 48. Preparation of 5-(4-bromo-3-chlorophenoxy)-1H-1,2,3-triazole-4-carboxylic Acid (8q)

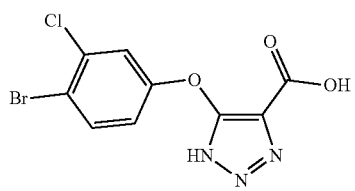

8q

The title compound was prepared as described in the previous example 1 and 2 using methyl 5-chloro-1-(4-methoxybenzyl)-1H-1,2,3-triazole-4-carboxylate 4a and anisole for the PMB deprotection. $^1$H NMR (400 MHz, DMSO-$d_6$) δ 7.73 (d, J=8.9 Hz, 1H), 7.43 (d, J=2.8 Hz, 1H), 7.01 (dd, J=8.9, 2.9 Hz, 1H). MS: ES– 315.86 (M–1).

Example 49. Preparation of 5-((6-chloropyridin-3-yl)oxy)-1H-1,2,3-triazole-4-carboxylic Acid (8r)

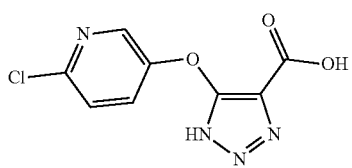

8r

The title compound was prepared as described in the previous example 1 and 2 using methyl 5-chloro-1-(4-methoxybenzyl)-1H-1,2,3-triazole-4-carboxylate 4a and anisole for the PMB deprotection. $^1$H NMR (400 MHz, DMSO-d$_6$) δ 8.32 (d, J=3.1 Hz, 1H), 7.67 (dd, J=8.8, 3.1 Hz, 1H), 7.52 (d, J=8.8 Hz, 1H). MS: ES+ 241.08 (M+23).

Example 50. Preparation of 5-((4'-cyano-[1,1'-biphenyl]-4-yl)thio)-1H-1,2,3-triazole-4-carboxylic Acid (8s)

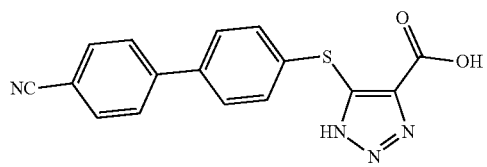

8s

The title compound was prepared as described in the previous example 1 and 2 using 4'-mercapto-[1,1'-biphenyl]-4-carbonitrile for the addition on methyl 5-chloro-1-(4-methoxybenzyl)-1H-1,2,3-triazole-4-carboxylate 4a and anisole for the PMB deprotection. $^1$H NMR (400 MHz, DMSO-d$_6$) δ 7.90 (q, J=8.6 Hz, 4H), 7.73 (d, J=8.3 Hz, 2H), 7.49 (d, J=8.3 Hz, 2H). MS: ES− 320.87 (M−1).

Example 51. Preparation of 5-(4-bromo-2-fluorophenoxy)-1H-1,2,3-triazole-4-carboxylic Acid (8t)

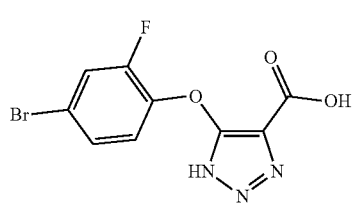

8t

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF for the phenol addition and anisole for the PMB deprotection. $^1$H NMR (400 MHz, DMSO-d$_6$) δ 7.74 (dd, J=10.5, 2.3 Hz, 1H), 7.39 (dd, J=8.8, 1.5 Hz, 1H), 7.21 (t, J=8.7 Hz, 1H). MS: ES+ 323.99 (M+23).

Example 52. Preparation of 5-((4-bromophenyl)thio)-1H-1,2,3-triazole-4-carboxylic Acid (8u)

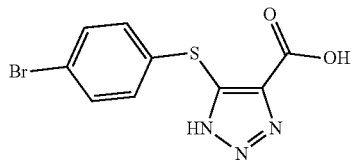

8u

The title compound was prepared as described in the previous example 1 and 2 using 4-bromothiophenol for the addition on methyl 5-chloro-1-(4-methoxybenzyl)-1H-1,2,3-triazole-4-carboxylate 4a and anisole for the PMB deprotection. $^1$H NMR (400 MHz, DMSO-d$_6$) δ 7.57 (d, J=8.5 Hz, 2H), 7.38 (d, J=8.4 Hz, 2H). MS: ES+ 321.95 (M+23).

Example 53. Preparation of 5-(4-cyanophenoxy)-1H-1,2,3-triazole-4-carboxylic Acid (8v)

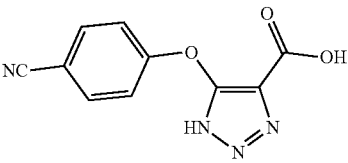

8v

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF for the phenol derivative addition and anisole for the PMB deprotection. $^1$H NMR (400 MHz, DMSO-d$_6$) δ 7.73 (d, J=8.8 Hz, 2H), 6.98 (d, J=8.8 Hz, 2H). MS: ES− 229.03 (M−1).

Example 54. Preparation of 5-((6-methylpyridin-3-yl)oxy)-1H-1,2,3-triazole-4-carboxylic Acid (8x)

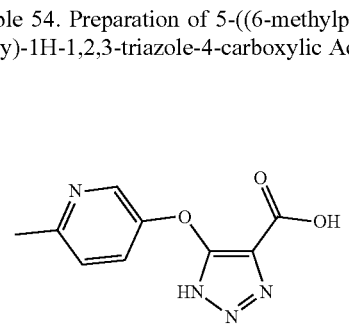

8x

The title compound was prepared as described in the previous example 1 and 2 using methyl 5-chloro-1-(4-methoxybenzyl)-1H-1,2,3-triazole-4-carboxylate 4a. $^1$H NMR (400 MHz, DMSO-d$_6$) δ 8.81 (s, 1H), 8.38 (dd, J=8.9, 2.7 Hz, 1H), 7.94 (d, J=9.1 Hz, 1H), 2.78 (s, 3H). MS: ES+ 221.18 (M+1).

Example 55. Preparation of 5-((6-(4-cyanophenyl)pyridin-3-yl)oxy)-1H-1,2,3-triazole-4-carboxylic Acid (12z)

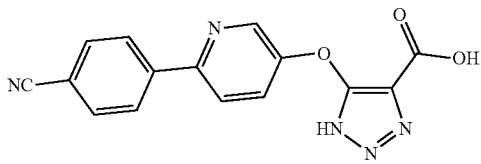

12z

The title compound was prepared as described in Example 11 using the intermediate of 8r for the cross coupling reaction. $^1$H NMR (400 MHz, DMSO-d$_6$) δ 8.42 (d, J=2.6 Hz, 1H), 8.21 (d, J=8.7 Hz, 2H), 8.03 (m, 1H), 7.91 (d, J=8.6 Hz, 2H), 7.38 (m, 1H). MS: ES− 306.08 (M−1).

Example 56. Preparation of 5-(4-carbamoylphe-noxy)-1H-1,2,3-triazole-4-carboxylic Acid (8y)

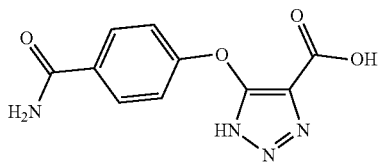

8y

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF for the phenol derivative addition and anisole for the PMB deprotection. $^1$H NMR (400 MHz, DMSO-d$_6$) δ 7.92 (d, J=8.9 Hz, 2H), 7.11 (d, J=8.9 Hz, 2H). MS: ES− 247.00 (M−1).

Example 57. Preparation of 5-((2-fluoropyridin-3-yl)oxy)-1H-1,2,3-triazole-4-carboxylic Acid (8z)

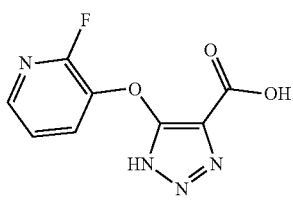

8z

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF for the phenol derivative addition and anisole for the PMB deprotection. $^1$H NMR (400 MHz, CD$_3$OD) δ 8.01 (m, 1H), 7.75 (m, 1H), 7.32, (m, 1H). MS: ES+ 225.14 (M+1).

Example 58. Preparation of 5-(3-(dimethylamino)phenoxy)-1H-1,2,3-triazole-4-carboxylic Acid (8aa)

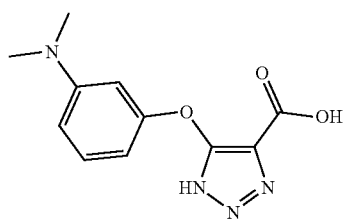

8aa

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF for the phenol derivative addition and anisole for the PMB deprotection. $^1$H NMR (400 MHz, DMSO-d$_6$) δ 7.07 (t, J=8.2 Hz, 1H), 6.43 (d, J=8.4 Hz, 1H), 6.35 (s, 1H), 6.18 (d, J=8.0 Hz, 1H), 2.85 (s, 6H). MS: ES− 247.11 (M−1).

Example 59. Preparation of 5-(3-(2-methylpyrimi-din-5-yl)phenoxy)-1H-1,2,3-triazole-4-carboxylic Acid (12aa)

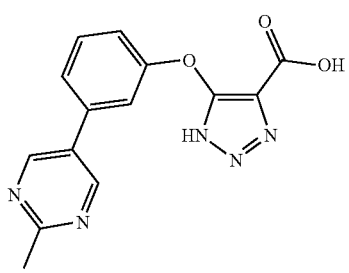

12aa

The title compound was prepared as described in Example 11 using the intermediate of 8g for the cross coupling reaction. $^1$H NMR (400 MHz, DMSO-d$_6$) δ 9.00 (s, 2H), 7.55 (m, 2H), 7.49 (t, J=8.2 Hz, 1H), 7.09 (d, J=7.6 Hz, 1H), 2.64 (s, 3H). MS: ES+ 298.19 (M+1).

Example 60. Preparation of 5-(4-(trifluoromethyl)phenoxy)-1H-1,2,3-triazole-4-carboxylic Acid (8ab)

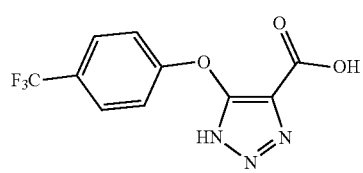

8ab

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF for the phenol derivative addition and anisole for the PMB deprotection. $^1$H NMR (400 MHz, DMSO-d$_6$) δ 7.72 (d, J=8.7 Hz, 2H), 7.23 (d, J=8.7 Hz, 2H). MS: ES− 272.01 (M−1).

Example 61. Preparation of 5-(3-(2-fluoropyridin-3-yl)phenoxy)-1H-1,2,3-triazole-4-carboxylic Acid (12ab)

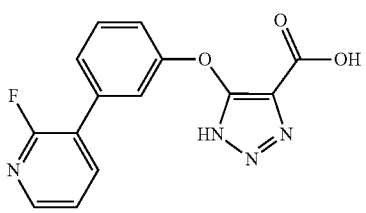

12ab

The title compound was prepared as described in Example 11 using the intermediate of 8g for the cross coupling reaction and anisole for PMB deprotection $^1$H NMR (400 MHz, DMSO-d$_6$) δ 8.24 (d, J=4.7 Hz, 1H), 8.17-8.04 (m, 1H), 7.46 (ddd, J=10.4, 7.0, 4.9 Hz, 2H), 7.43-7.30 (m, 2H), 7.13 (dd, J=8.2, 2.5 Hz, 1H). MS: ES+ 301.18 (M+1).

Example 62. Preparation of 5-((4-(2-fluoropyridin-3-yl)phenyl)thio)-1H-1,2,3-triazole-4-carboxylic Acid (12ac)

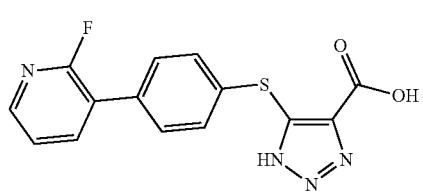

12ac

The title compound was prepared as described in Example 11 using the intermediate of 8u for the cross coupling reaction and anisole for PMB deprotection. ¹H NMR (400 MHz, DMSO-d₆) δ 8.27-8.22 (m, 1H), 8.19-8.06 (m, 1H), 7.68-7.58 (m, 2H), 7.60-7.50 (m, 2H), 7.51-7.43 (m, 1H). MS: ES− 315.04 (M−1).

Example 63. Preparation of 5-((4'-carbamoyl-[1,1'-biphenyl]-3-yl)oxy)-1H-1,2,3-triazole-4-carboxylic Acid (12ad)

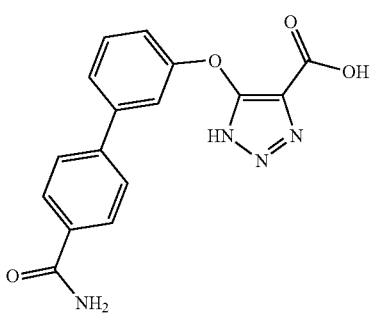

12ad

The title compound was prepared as described in Example 11 using the intermediate of 8g for the cross coupling reaction and anisole for PMB deprotection. ¹H NMR (400 MHz, DMSO-d₆) δ 7.99 (d, J=8.4 Hz, 2H), 7.77 (d, J=8.5 Hz, 2H), 7.54-7.42 (m, 3H), 7.09 (d, J=8.3 Hz, 1H). MS: ES+ 325.20 (M+1).

Example 64. Preparation of 5-((4'-cyano-[1,1'-biphenyl]-3-yl)oxy)-1H-1,2,3-triazole-4-carboxylic Acid (12ae)

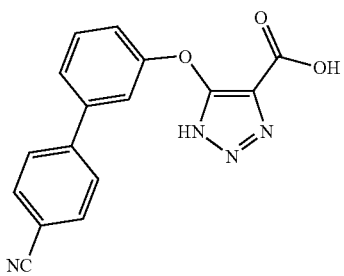

12ae

The title compound was prepared as described in Example 11 using the intermediate of 8g for the cross coupling reaction and anisole for PMB deprotection. ¹H NMR (400 MHz, DMSO-d₆) δ 7.88 (m, 4H), 7.59-7.40 (m, 3H), 7.13-7.03 (m, 1H). MS: ES− 305.15 (M−1).

Example 65. Preparation of 5-(4-(4-methylpiperazin-1-yl)phenoxy)-1H-1,2,3-triazole-4-carboxylic Acid (8ac)

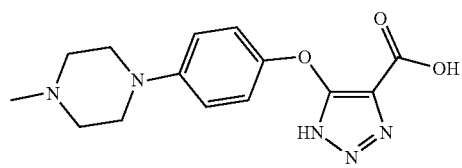

8ac

To the methyl 1-(4-methoxybenzyl)-5-(4-(piperazin-1-yl)phenoxy)-1H-1,2,3-triazole-4-carboxylate (0.280, 0.661 mmol) (intermediate of 8b) in THF (3 mL) and acetic acid (0.6 mL) was added formaldehyde in water solution (177 uL, 2.18 mmol). After a period of 30 min, was added the triacetoxyborohydride (150 mg, 0.708 mmol) portionwise. After a period of 15 min, the reaction mixture was extracted with EA and NaHCO₃, the EA collected, dried over sodium sulfate, filtered and evaporated. The mixture was purified on a 40 g column with DCM to 10% MeOH in DCM (load with DCM/MeOH) to provide methyl 1-(4-methoxybenzyl)-5-(4-(4-methylpiperazin-1-yl)phenoxy)-1H-1,2,3-triazole-4-carboxylate (0.200 g, 0.457 mmol). As described for example 8b after deprotection and hydrolysis the title compound was obtained (0.214, 0.693 mmol). ¹H NMR (400 MHz, CD₃OD) δ 7.05 (m, 4H), 3.34 (s, 8H), 2.96 (s, 3H). MS: ES+ 304.24 (M+1).

Example 66. Preparation of 5-((2-bromopyridin-3-yl)oxy)-1H-1,2,3-triazole-4-carboxylic Acid (8ad)

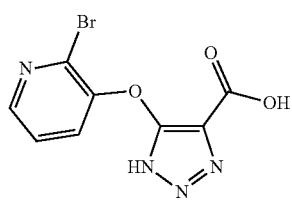

8ad

The title compound was prepared as described in the previous example 1 and 2 using methyl 5-chloro-1-(4-methoxybenzyl)-1H-1,2,3-triazole-4-carboxylate 4a but using Cs₂CO₃/DMF for the phenol derivative addition and anisole for the PMB deprotection. ¹H NMR (400 MHz, DMSO-d₆) δ 8.31 (dd, J=4.6, 1.5 Hz, 1H), 7.68 (d, J=8.2 Hz, 1H), 7.53 (dd, J=8.1, 4.6 Hz, 1H). MS: ES+ 283.95 (M+1).

Example 67. Preparation of 5-((2,6-dimethylpyridin-3-yl)oxy)-1H-1,2,3-triazole-4-carboxylic Acid (8ae)

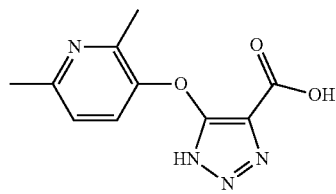

8ae

The title compound was prepared as described in the previous example 1 and 2 using methyl 5-chloro-1-(4-methoxybenzyl)-1H-1,2,3-triazole-4-carboxylate 4a but using $Cs_2CO_3$/DMF for the phenol derivative addition and anisole for the PMB deprotection. $^1$H NMR (400 MHz, $CD_3OD$) δ 8.19 (d, J=8.8 Hz, 1H), 7.70 (d, J=8.8 Hz, 1H), 2.80 (s, 3H), 2.73 (s, 3H). MS: ES+ 234.07 (M+1).

Example 68. Preparation of 5-(4-(tert-butyl)phenoxy)-1H-1,2,3-triazole-4-carboxylic Acid (8af)

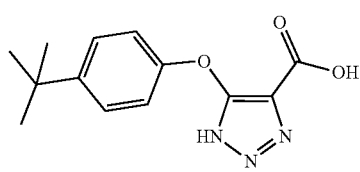

8af

The title compound was prepared as described in the previous example 1 and 2 using methyl 5-chloro-1-(4-methoxybenzyl)-1H-1,2,3-triazole-4-carboxylate 4a but using $Cs_2CO_3$/DMF and anisole for the PMB deprotection. $^1$H NMR (400 MHz, DMSO-$d_6$) δ 7.35 (d, J=8.0 Hz, 2H), 6.96 (d, J=7.9 Hz, 2H), 1.25 (s, 9H). MS: ES+ 262.20 (M+1).

Example 69. Preparation of 5-(4-cyclopentylphenoxy)-1H-1,2,3-triazole-4-carboxylic Acid (8ag)

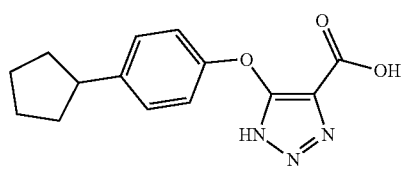

8ag

The title compound was prepared as described in the previous example 1 and 2 using methyl 5-chloro-1-(4-methoxybenzyl)-1H-1,2,3-triazole-4-carboxylate 4a but using $Cs_2CO_3$/DMF and anisole for the PMB deprotection. $^1$H NMR (400 MHz, DMSO) δ 7.21 (d, J=8.5 Hz, 2H), 6.96 (d, J=8.6 Hz, 2H), 3.05-2.80 (m, 1H), 2.14-1.86 (m, 2H), 1.82-1.68 (m, 2H), 1.67-1.54 (m, 2H), 1.58-1.33 (m, 2H). MS: ES− 272.20 (M−1).

Example 70. Preparation of 5-((6-methoxypyridin-3-yl)oxy)-1H-1,2,3-triazole-4-carboxylic Acid (8ah)

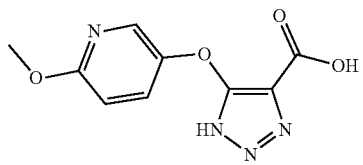

8ah

The title compound was prepared as described in the previous example 1 and 2 using methyl 5-chloro-1-(4-methoxybenzyl)-1H-1,2,3-triazole-4-carboxylate 4a but using $Cs_2CO_3$/DMF for the phenol derivative addition and anisole for the PMB deprotection. $^1$H NMR (400 MHz, DMSO-$d_6$) δ 8.05 (d, J=2.6 Hz, 1H), 7.59 (dd, J=9.0, 3.0 Hz, 1H), 6.83 (d, J=9.0 Hz, 1H). MS: ES− 235.14 (M−1).

Example 71. Preparation of 5-(4-bromo-3-methylphenoxy)-1H-1,2,3-triazole-4-carboxylic Acid (8ai)

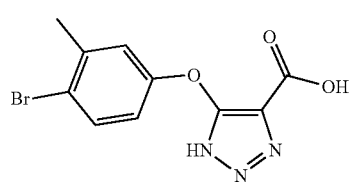

8ai

The title compound was prepared as described in the previous example 1 and 2 using methyl 5-chloro-1-(4-methoxybenzyl)-1H-1,2,3-triazole-4-carboxylate 4a. $^1$H NMR (400 MHz, $CD_3OD$) δ δ 7.46 (d, J=8.7 Hz, 1H), 7.02 (d, J=2.8 Hz, 1H), 6.81 (m, 1H), 2.34 (s, 3H). MS: ES+ 256 (M+2-44).

Example 72. Preparation of 5-(4-(2-fluoropyridin-3-yl)-3-methylphenoxy)-1H-1,2,3-triazole-4-carboxylic Acid (12af)

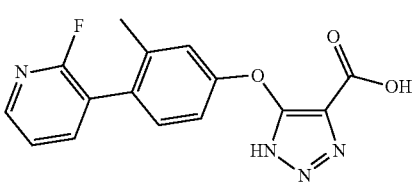

12af

The title compound was prepared as described in Example 11 using the intermediate of 8ai for the cross coupling reaction and anisole for PMB deprotection. $^1$H NMR (400 MHz, DMSO-$d_6$) δ 8.26 (d, J=4.7 Hz, 1H), 8.05-7.76 (m, 1H), 7.65-7.31 (m, 1H), 7.23 (d, J=8.4 Hz, 1H), 7.06 (d, J=2.5 Hz, 1H), 6.96 (dd, J=8.4, 2.6 Hz, 1H), 2.10 (s, 3H). MS: ES+271 (M+1-44).

Example 73. Preparation of 5-(4-(6-fluoro-2-methylpyridin-3-yl)phenoxy)-1H-1,2,3-triazole-4-carboxylic Acid (12ag)

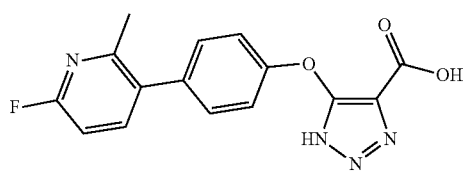

12ag

The title compound was prepared as described in Example 11 using the intermediate 9a for the cross coupling reaction and anisole for PMB deprotection. $^1$H NMR (400 MHz, DMSO-d$_6$) δ 7.80 (t, J=8.1 Hz, 1H), 7.38 (d, J=8.6 Hz, 2H), 7.14 (d, J=8.6 Hz, 2H), 7.05 (d, J=8.5 Hz, 1H), 2.36 (s, 3H). MS: ES− 313.18 (M−1).

Example 74. Preparation of 5-(4-(6-fluoro-4-methylpyridin-2-yl)phenoxy)-1H-1,2,3-triazole-4-carboxylic Acid (12ah)

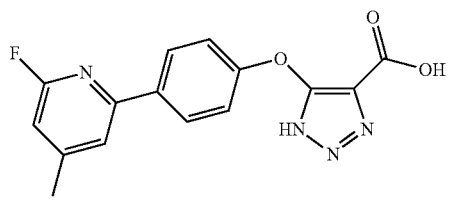

12ah

The title compound was prepared as described in Example 11 using the intermediate 9a for the cross coupling reaction and anisole for PMB deprotection. $^1$H NMR (400 MHz, DMSO-d$_6$) δ 5 8.15-7.92 (m, 2H), 7.75 (m, 1H), 7.15 (d, J=8.9 Hz, 2H), 6.94 (m, 1H), 2.42 (s, 3H). MS: ES+ 315.20 (M+1).

Example 75. Preparation of 5-(4-(2-fluoro-3-methylpyridin-4-yl)phenoxy)-1H-1,2,3-triazole-4-carboxylic Acid (12ai)

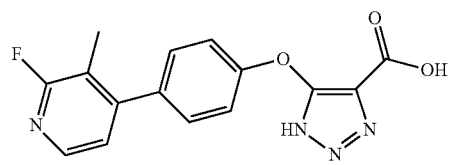

12ai

The title compound was prepared as described in Example 11 using the intermediate 9a for the cross coupling reaction and anisole for PMB deprotection. $^1$H NMR (400 MHz, DMSO-d$_6$) δ 8.07 (d, J=5.0 Hz, 1H), 7.46-7.37 (m, 2H), 7.23 (d, J=4.6 Hz, 1H), 7.19-7.08 (m, 2H), 2.16 (s, 3H). ES+ 315.20 (M+1).

Example 76. Preparation of 5-(4-(3-bicyclo[1.1.1]pentan-1-yl)phenoxy)-1H-1,2,3-triazole-4-carboxylic Acid (8aj)

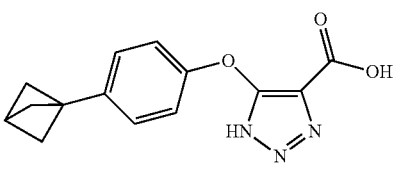

8aj

The title compound was prepared as described in the previous example 1 and 2 using methyl 5-chloro-1-(4-methoxybenzyl)-1H-1,2,3-triazole-4-carboxylate 4a and anisole for the PMB deprotection. $^1$H NMR (400 MHz, CD$_3$OD) δ 7.45-7.08 (m, 2H), 7.09-6.89 (m, 2H), 2.52 (s, 1H), 2.07 (s, 6H). MS: ES+ 272.14 (M+1).

Example 77. Preparation of 5-(4-(4-oxocyclohexyl)phenoxy)-1H-1,2,3-triazole-4-carboxylic Acid (8ak)

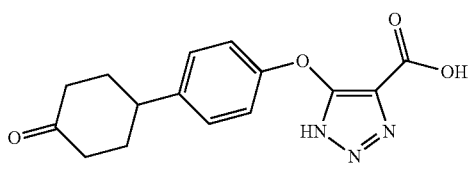

8ak

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF and anisole for the PMB deprotection. $^1$H NMR (400 MHz, DMSO-d$_6$) δ 7.28 (d, J=8.6 Hz, 2H), 6.99 (d, J=8.6 Hz, 2H), 3.11-2.95 (m, 1H), 2.56 (m, 2H), 2.29-2.17 (m, 2H), 2.10-1.94 (m, 2H), 1.94-1.75 (m, 2H). MS: ES− 300.13 (M−1).

Example 78. Preparation of 5-(4-(2-fluoro-6-methylpyridin-3-yl)-3-methylphenoxy)-1H-1,2,3-triazole-4-carboxylic Acid (12aj)

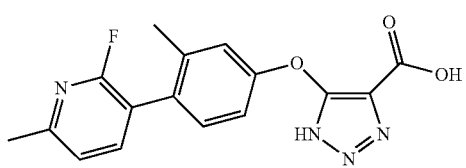

12aj

The title compound was prepared as described in Example 11 using the intermediate of 8ai for the cross coupling reaction and anisole for PMB deprotection. $^1$H NMR (400 MHz, DMSO-d$_6$) δ 7.77 (dd, J=10.2, 7.5 Hz, 1H), 7.28 (d, J=7.4 Hz, 1H), 7.19 (d, J=8.4 Hz, 1H), 7.04 (d, J=2.4 Hz, 1H), 6.94 (dd, J=8.3, 2.5 Hz, 1H), 2.46 (s, 3H), 2.09 (s, 3H). MS: ES+ 329.20 (M+1).

Example 79. Preparation of 5-(4-(2-fluoro-6-methylpyridin-3-yl)phenoxy)-1H-1,2,3-triazole-4-carboxylic Acid (12ak)

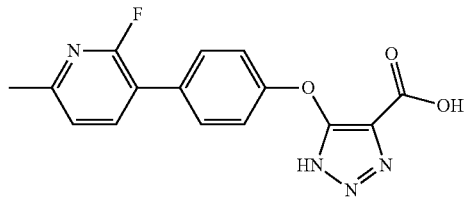

The title compound was prepared as described in Example 11 using the intermediate 9a for the cross coupling reaction and anisole for PMB deprotection. $^1$H NMR (400 MHz, DMSO-d$_6$) δ 7.98 (dd, J=10.6, 7.6 Hz, 1H), 7.57 (d, J=7.4 Hz, 2H), 7.30 (d, J=7.5 Hz, 1H), 7.16 (d, J=8.8 Hz, 2H), 2.45 (s, 3H). MS: ES+ 315.17 (M+1).

Example 80. Preparation of 5-(4-(5-methylpyridin-3-yl)phenoxy)-1H-1,2,3-triazole-4-carboxylic Acid (12al)

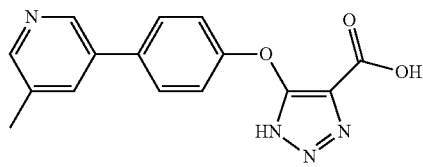

The title compound was prepared as described in Example 11 using the intermediate 9a for the cross coupling reaction and anisole for PMB deprotection. $^1$H NMR (400 MHz, DMSO-d$_6$) δ 5 8.63 (d, J=5.7 Hz, 1H), 7.89 (m, 4H), 7.23 (d, J=8.8 Hz, 2H), 2.63 (s, 3H). MS: ES+ 297.24 (M+1).

Example 81. Preparation of 5-(4-(2-methylpyridin-4-yl)phenoxy)-1H-1,2,3-triazole-4-carboxylic Acid (12am)

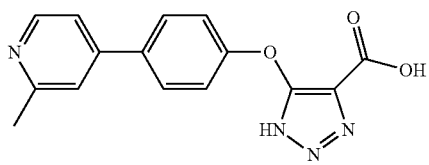

The title compound was prepared as described in Example 11 using the intermediate 9a for the cross coupling reaction and anisole for PMB deprotection. $^1$H NMR (400 MHz, DMSO-d$_6$) δ 8.68 (d, J=1.9 Hz, 1H), 8.40 (m, 1H), 7.92 (s, mH), 7.78-7.63 (m, 2H), 7.23-7.12 (m, 2H), 2.36 (s, 3H). MS: ES+ 297.24 (M+1).

Example 82. Preparation of 5-(4-(6-fluoro-5-methylpyridin-3-yl)phenoxy)-1H-1,2,3-triazole-4-carboxylic Acid (12an)

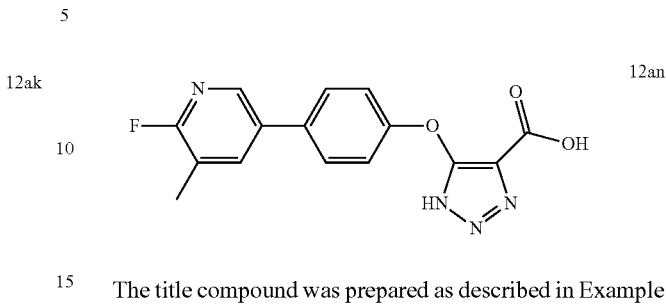

The title compound was prepared as described in Example 11 using the intermediate 9a for the cross coupling reaction and anisole for PMB deprotection. $^1$H NMR (400 MHz, DMSO-d$_6$) δ 8.30 (s, 1H), 8.12 (d, J=9.6 Hz, 1H), 7.68 (d, J=8.8 Hz, 2H), 7.15 (d, J=8.8 Hz, 2H), 2.29 (s, 3H). MS: ES+ 315.20 (M+1).

Example 83. Preparation of 5-(4-(quinolin-4-yl)phenoxy)-1H-1,2,3-triazole-4-carboxylic Acid (12ao)

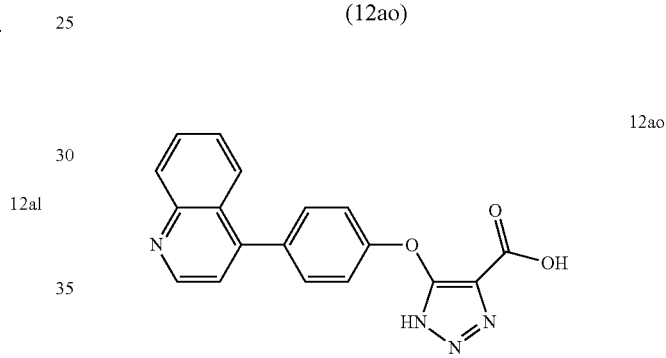

The title compound was prepared as described in Example 11 using the intermediate 9a for the cross coupling reaction and anisole for PMB deprotection. $^1$H NMR (400 MHz, DMSO-d$_6$) δ 9.09 (d, J=4.9 Hz, 1H), 8.21 (d, J=8.4 Hz, 1H), 8.00 (d, J=8.4 Hz, 1H), 7.93 (d, J=7.4 Hz, 1H), 7.80-7.65 (m, 2H), 7.66-7.57 (m, 2H), 7.37-7.22 (m, 2H). MS: ES− 331.19 (M−1).

Example 84. Preparation of 5-(4-(6-methylpyridin-3-yl)phenoxy)-1H-1,2,3-triazole-4-carboxylic Acid (12ap)

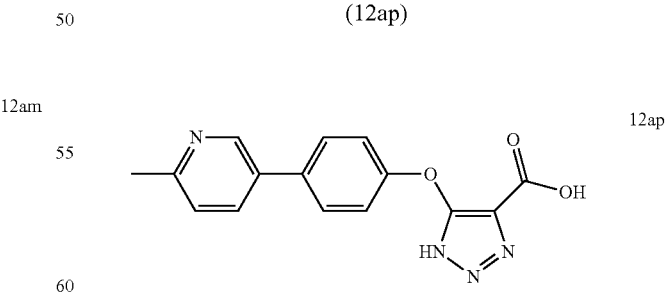

The title compound was prepared as described in Example 11 using the intermediate 8a for the cross coupling reaction and anisole for PMB deprotection. $^1$H NMR (400 MHz, DMSO-d$_6$) δ 9.00 (s, 1H), 8.66-8.45 (m, 1H), 8.10-7.64 (m, 3H), 7.22 (d, J=8.8 Hz, 2H), 2.68 (s, 3H). MS: ES+ 297.19 (M+1).

Example 85. Preparation of 5-(4-(6-fluoro-2-methylpyridin-3-yl)-3-methylphenoxy)-1H-1,2,3-triazole-4-carboxylic Acid (12aq)

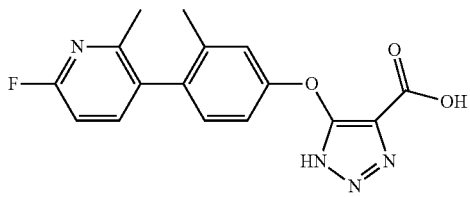

The title compound was prepared as described in Example 11 using the intermediate of 8ai for the cross coupling reaction and anisole for PMB deprotection. $^1$H NMR (400 MHz, CD$_3$OD) δ7.67 (t, J=8.1 Hz, 1H), 7.11 (d, J=8.5 Hz, 2H), 7.04-6.91 (m, 2H), 2.22 (s, 3H), 2.05 (s, 3H). MS: ES− 327.12 (M−1).

Example 86. Preparation of 5-(4-(6-fluoro-5-methylpyridin-3-yl)-3-methylphenoxy)-1H-1,2,3-triazole-4-carboxylic Acid (12ar)

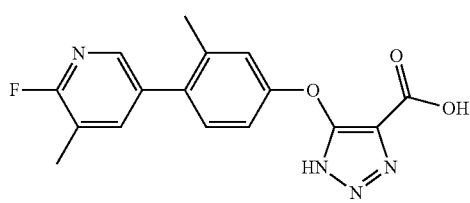

The title compound was prepared as described in Example 11 using the intermediate of 8ai for the cross coupling reaction and anisole for PMB deprotection. $^1$H NMR (400 MHz, CD$_3$OD) δ. 7.93 (s, 1H), 7.80-7.72 (m, 1H), 7.20 (d, J=8.4 Hz, 1H), 7.08 (d, J=2.6 Hz, 1H), 7.00 (dd, J=8.3, 2.3 Hz, 1H), 2.34 (s, 3H), 2.24 (s, 3H). MS: ES− 327.18 (M−1).

Example 87. Preparation of 5-(4-(4,4-difluorocyclohexyl)phenoxy)-1H-1,2,3-triazole-4-carboxylic Acid (8al)

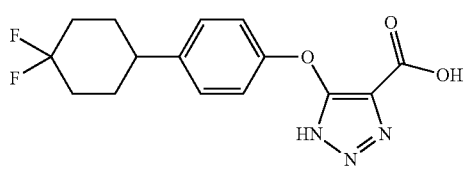

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF and anisole for the PMB deprotection. $^1$H NMR (400 MHz, CD$_3$OD) δ 7.28 (d, J=8.6 Hz, 2H), 6.99 (d, J=8.6 Hz, 2H), 3.11-2.95 (m, 1H), 2.56 (m, 2H), 2.29-2.17 (m, 2H), 2.10-1.94 (m, 2H), 1.94-1.75 (m, 2H). MS: ES+ 324.18 (M+1).

Example 88. Preparation of 5-(4-(tetrahydro-2H-pyran-4-yl)phenoxy)-1H-1,2,3-triazole-4-carboxylic Acid (12as)

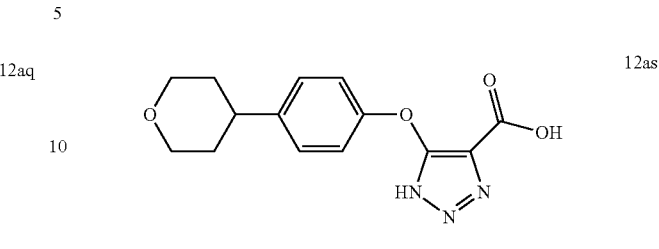

The title compound was prepared as described in Example 11 using the intermediate of 9a for the cross coupling reaction with 2-(3,6-dihydro-2H-pyran-4-yl)-4,4,5,5-tetramethyl-1,3,2-dioxaborolane followed by hydrogenation at 1 atm with Pd/C in MeOH for 4 h. Anisole was used for PMB deprotection. $^1$H NMR (400 MHz, DMSO-d$_6$) δ 7.23 (d, J=8.6 Hz, 2H), 6.99 (d, J=8.7 Hz, 2H), 3.92 (dd, J=11.5, 2.2 Hz, 2H), 3.40 (td, J=11.3, 2.8 Hz, 2H), 2.84-2.65 (m, 1H), 1.80-1.45 (m, 4H). MS: ES− 288.13 (M−1).

Example 89. Preparation of 5-(4-bromo-3-methoxyphenoxy)-1H-1,2,3-triazole-4-carboxylic Acid (8am)

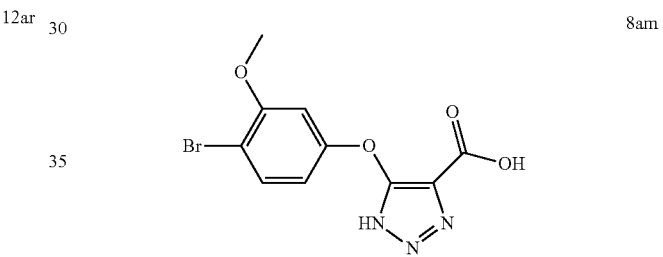

The title compound was prepared as described in the previous example 1 and 2 using methyl 5-chloro-1-(4-methoxybenzyl)-1H-1,2,3-triazole-4-carboxylate 4a and anisole for the PMB deprotection. $^1$H NMR (400 MHz, DMSO-d$_6$) 7.50 (d, J=8.7 Hz, 1H), 6.92 (d, J=2.7 Hz, 1H), 6.52 (dd, J=8.7, 2.7 Hz, 1H), 3.81 (s, 3H). MS: ES+ 312.01 (M+1)

Example 90. Preparation of 5-(3-methoxy-4-(6-methoxypyridin-3-yl)phenoxy)-1H-1,2,3-triazole-4-carboxylic Acid (12at)

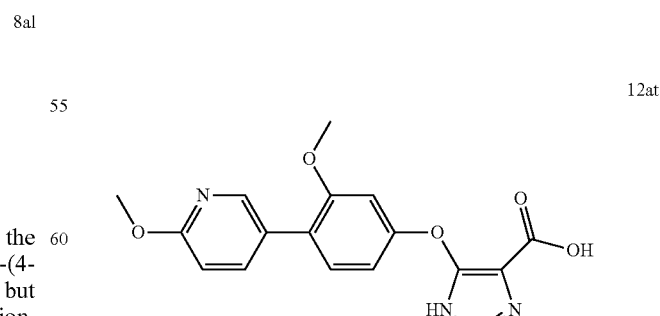

The title compound was prepared as described in Example 11 using the intermediate of 8am for the cross coupling reaction and anisole for PMB deprotection. ¹H NMR (400 MHz, DMSO-d₆) δ 8.21 (d, J=2.0 Hz, 1H), 7.78 (dd, J=8.6, 2.5 Hz, 1H), 7.27 (d, J=8.4 Hz, 1H), 6.91 (d, J=2.1 Hz, 1H), 6.84 (d, J=8.6 Hz, 1H), 6.64 (s, 1H), 3.86 (s, 3H), 3.74 (s, 3H). MS: ES+ 343.24 (M+1).

Example 91. Preparation of 5-(4-(2,6-dimethoxy-pyridin-3-yl)-3-methoxyphenoxy)-1H-1,2,3-triazole-4-carboxylic Acid (12au)

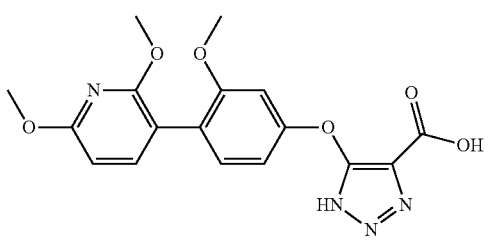

The title compound was prepared as described in Example 11 using the intermediate of 8am for the cross coupling reaction and anisole for PMB deprotection. ¹H NMR (400 MHz, DMSO-d₆) δ 7.44 (d, J=8.0 Hz, 1H), 7.00 (d, J=8.4 Hz, 1H), 6.68 (d, J=2.3 Hz, 1H), 6.42-6.33 (m, 2H), 3.86 (s, 3H), 3.79 (s, 3H), 3.63 (s, 3H). MS: ES+ 395.19 (M+23).

Example 92. Preparation of 5-(4-(2-fluoropyridin-4-yl)phenoxy)-1H-1,2,3-triazole-4-carboxylic Acid (12av)

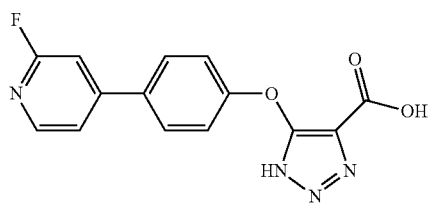

The title compound was prepared as described in Example 11 using the intermediate 9a for the cross coupling reaction and anisole for PMB deprotection. ¹H NMR (400 MHz, DMSO-d₆) δ 8.27 (d, J=5.3 Hz, 1H), 7.87 (d, J=8.8 Hz, 2H), 7.67 (d, J=5.4 Hz, 1H), 7.51 (s, 1H), 7.19 (d, J=8.8 Hz, 2H). MS: ES- 299.15 (M+23).

Example 93. Preparation of 5-(4-(2-chloropyridin-3-yl)phenoxy)-1H-1,2,3-triazole-4-carboxylic Acid (12aw)

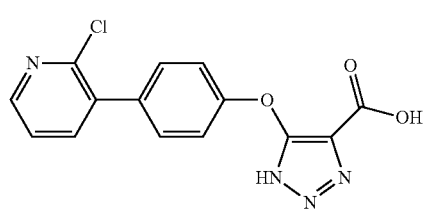

The title compound was prepared as described in Example 11 using the intermediate 9a for the cross coupling reaction and anisole for PMB deprotection. ¹H NMR (400 MHz, DMSO-d₆) δ 8.41 (dd, J=4.7, 1.9 Hz, 1H), 7.88 (dd, J=7.6, 1.9 Hz, 1H), 7.54-7.45 (m, 3H), 7.16 (d, J=8.8 Hz, 2H). MS: ES- 315.01 (M-1).

Example 94. Preparation of 5-(4-(1-naphthyl)phenoxy)-1H-1,2,3-triazole-4-carboxylic Acid (12ax)

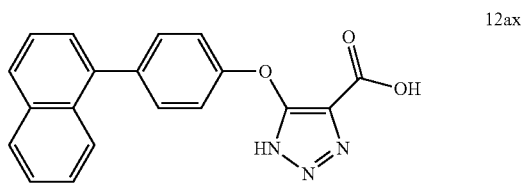 [SMILES: O=C(O)c1nn[nH]c1Oc1ccc(-c2cccc3ccccc23)cc1]

The title compound was prepared as described in Example 11 using the intermediate 9a for the cross coupling reaction and anisole for PMB deprotection. ¹H NMR (400 MHz, DMSO-d₆) δ 57.95 (m, 2H), 7.81 (d, J=8.1 Hz, 1H), 7.59-7.39 (m, 6H), 7.11 (d, J=8.4 Hz, 2H). MS: ES- 330.11 (M-1).

Example 95. Preparation of 5-(4-bromo-3-(trifluoromethyl)phenoxy)-1H-1,2,3-triazole-4-carboxylic Acid (8an)

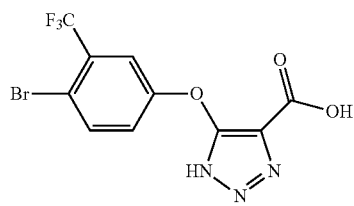

The title compound was prepared as described in the previous example 1 and 2 using methyl 5-chloro-1-(4-methoxybenzyl)-1H-1,2,3-triazole-4-carboxylate 4a but using Cs₂CO₃/DMF and anisole for the PMB deprotection. ¹H NMR (400 MHz, DMSO-d₆) δ 7.94 (d, J=2.4 Hz, 1H), 7.81 (dd, J=8.8, 2.4 Hz, 1H), 7.11 (d, J=9.0 Hz, 1H). MS: ES- 350.02 (M-1).

Example 96. Preparation of 5-(4-(isoquinolin-4-yl)phenoxy)-1H-1,2,3-triazole-4-carboxylic Acid (12ay)

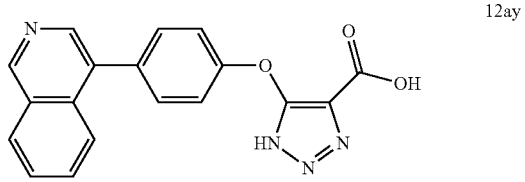 [SMILES: O=C(O)c1nn[nH]c1Oc1ccc(-c2cncc3ccccc23)cc1]

The title compound was prepared as described in Example 11 using the intermediate 9a for the cross coupling reaction and anisole for PMB deprotection. ¹H NMR (400 MHz, DMSO-d₆) δ 9.63 (s, 1H), 8.56 (s, 1H), 8.42 (d, J=8.2 Hz, 1H), 8.04-7.92 (m, 2H), 7.93-7.79 (m, 1H), 7.67-7.46 (m, 2H), 7.28 (d, J=8.7 Hz, 2H). MS: ES+ 333.13 (M+1).

Example 97. Preparation of 5-(4-(tetrahydro-2H-thiopyran-4-yl)phenoxy)-1H-1,2,3-triazole-4-carboxylic Acid (12az)

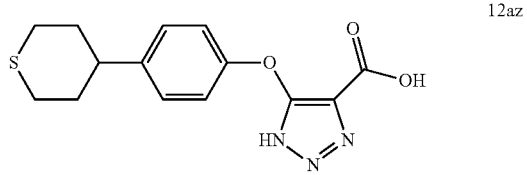

The title compound was prepared as described in Example 88 using the intermediate of 9a for the cross coupling reaction with 2-(3,6-dihydro-2H-thiopyran-4-yl)-4,4,5,5-tetramethyl-1,3,2-dioxoborolane followed by hydrogenation at 1 atm with Pd/C in MeOH for 4 h. Anisole was used for PMB deprotection. ¹H NMR (400 MHz, DMSO-d₆) δ 7.20 (d, J=8.7 Hz, 2H), 6.98 (d, J=8.7 Hz, 2H), 2.85-2.67 (m, 2H), 2.68-2.57 (m, 2H), 2.58-2.50 (m, 1H), 2.09-1.95 (m, 2H), 1.68 (m Hz, 2H). MS: ES− 304.09 (M−1).

Example 98. Preparation of 5-(2-fluoro-4-(2-fluoropyridin-3-yl)phenoxy)-1H-1,2,3-triazole-4-carboxylic Acid (12ba)

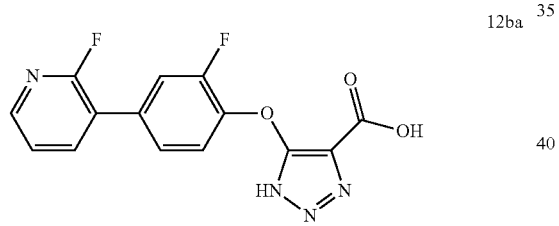

The title compound was prepared as described in Example 11 using the intermediate of 8t for the cross coupling reaction and anisole for PMB deprotection. ¹H NMR (400 MHz, CD₃OD) δ 8.21 (d, J=4.8 Hz, 1H), 8.10 (ddd, J=9.7, 7.5, 1.8 Hz, 1H), 7.55 (d, J=11.8 Hz, 1H), 7.46-7.39 (m, 2H), 7.33 (t, J=8.4 Hz, 1H). MS: ES− 317.01 (M−1).

Example 99. Preparation of 5-(4-(2-chloro-5-fluoropyridin-3-yl)phenoxy)-1H-1,2,3-triazole-4-carboxylic Acid (12bb)

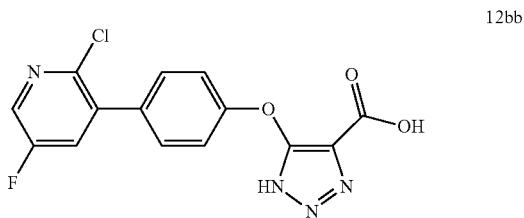 [SMILES: O=C(O)c1nn[nH]c1Oc1ccc(-c2cc(F)cnc2Cl)cc1]

The title compound was prepared as described in Example 11 using the intermediate 9a for the cross coupling reaction and anisole for PMB deprotection. ¹H NMR (400 MHz, DMSO-d₆) δ 8.48 (d, J=3.0 Hz, 1H), 7.96 (dd, J=8.7, 3.0 Hz, 1H), 7.56-7.47 (m, 2H), 7.18 (d, J=8.8 Hz, 2H). MS: ES− 333.00 (M−1).

Example 100. Preparation of 5-(4-(6-methoxypyridin-3-yl)phenoxy)-1H-1,2,3-triazole-4-carboxylic Acid (12bc)

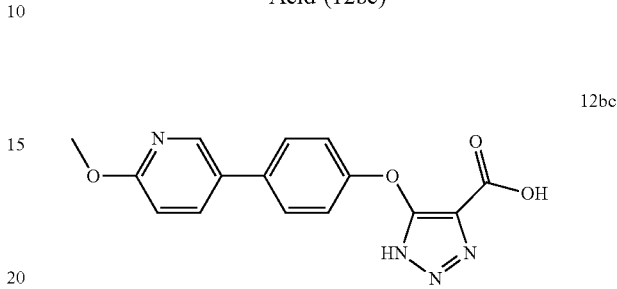

The title compound was prepared as described in Example 11 using the intermediate 9a for the cross coupling reaction and anisole for PMB deprotection. ¹H NMR (400 MHz, DMSO-d₆) δ 8.44 (d, J=2.0 Hz, 1H), 7.98 (dd, J=8.6, 2.6 Hz, 1H), 7.64 (d, J=8.8 Hz, 2H), 7.14 (d, J=8.8 Hz, 2H), 6.89 (d, J=8.6 Hz, 1H), 3.87 (s, 3H). MS: ES+ 335.11 (M+23).

Example 101. Preparation of 5-(4-(2,6-dimethoxypyridin-3-yl)phenoxy)-1H-1,2,3-triazole-4-carboxylic Acid (12bd)

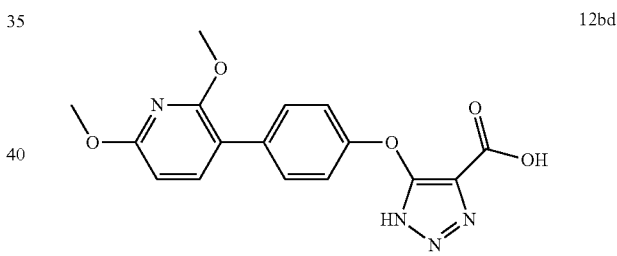

The title compound was prepared as described in Example 11 using the intermediate 9a for the cross coupling reaction and anisole for PMB deprotection. ¹H NMR (400 MHz, DMSO-d₆) δ 7.69 (d, J=8.1 Hz, 1H), 7.49 (d, J=8.8 Hz, 2H), 7.08 (d, J=8.8 Hz, 2H), 6.46 (d, J=8.1 Hz, 1H), 3.89 (s, 6H). MS: ES− 341.13 (M−1).

Example 102. Preparation of 5-((4'-(methylsulfonamido)-[1,1'-biphenyl]-4-yl)oxy)-1H-1,2,3-triazole-4-carboxylic Acid (12be)

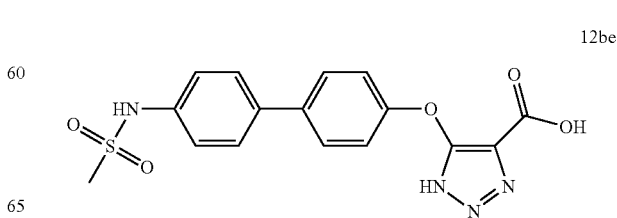

The title compound was prepared as described in Example 11 using the intermediate 9a for the cross coupling reaction and anisole for PMB deprotection. ¹H NMR (400 MHz, DMSO-d₆) δ 7.64-7.57 (m, 4H), 7.27 (d, J=8.7 Hz, 2H), 7.12 (d, J=8.8 Hz, 2H), 3.00 (s, 3H). MS: ES– 373.05 (M–1).

Example 103. Preparation of 5-((4'-(methylsulfonyl)-[1,1'-biphenyl]-4-yl)oxy)-1H-1,2,3-triazole-4-carboxylic Acid (12bf)

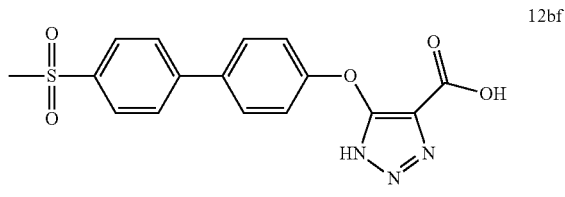 [SMILES: CS(=O)(=O)c1ccc(-c2ccc(Oc3[nH]nnc3C(=O)O)cc2)cc1]

12bf

The title compound was prepared as described in Example 11 using the intermediate 9a for the cross coupling reaction and anisole for PMB deprotection. ¹H NMR (400 MHz, DMSO-d₆) δ 7.97 (d, J=8.7 Hz, 2H), 7.90 (d, J=8.7 Hz, 2H), 7.74 (d, J=8.8 Hz, 2H), 7.15 (d, J=8.4 Hz, 2H), 3.23 (s, 3H). MS: ES– 358.10 (M–1).

Example 104. Preparation of 5-((3-fluoro-4'-(trifluoromethyl)-[1,1'-biphenyl]-4-yl)oxy)-1H-1,2,3-triazole-4-carboxylic Acid (12bg)

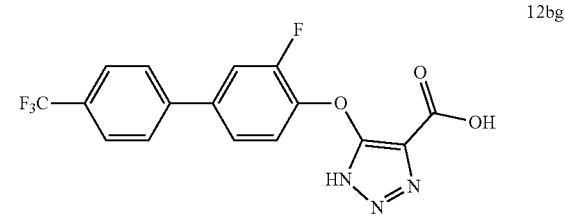 [SMILES: O=C(O)c1nn[nH]c1Oc1ccc(-c2ccc(C(F)(F)F)cc2)cc1F]

12bg

The title compound was prepared as described in Example 11 using the intermediate of 8t for the cross coupling reaction and anisole for PMB deprotection. ¹H NMR (400 MHz, DMSO-d₆) δ 7.93 (d, J=8.2 Hz, 2H), 7.86-7.78 (m, 3H), 7.58 (d, J=8.5 Hz, 1H), 7.34 (t, J=8.6 Hz, 1H). MS: ES– 366.08 (M–1).

Example 105. Preparation of 5-((3-fluoro-4'-(methylsulfonyl)-[1,1'-biphenyl]-4-yl)oxy)-1H-1,2,3-triazole-4-carboxylic Acid (12bh)

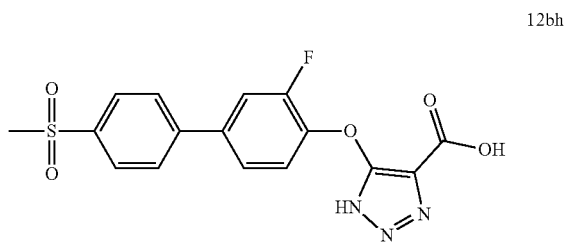 [SMILES: CS(=O)(=O)c1ccc(-c2ccc(Oc3[nH]nnc3C(=O)O)c(F)c2)cc1]

12bh

The title compound was prepared as described in Example 11 using the intermediate of 8t for the cross coupling reaction and anisole for PMB deprotection. ¹H NMR (400 MHz, DMSO-d₆) δ 7.98 (s, 4H), 7.85 (m, 1H), 7.60 (d, J=8.5 Hz, 1H), 7.35 (t, J=8.6 Hz, 1H), 3.25 (s, 3H). MS: ES– 376.06 (M–1).

Example 106. Preparation of 5-((4'-(tert-butyl)-3-fluoro-[1,1'-biphenyl]-4-yl)oxy)-1H-1,2,3-triazole-4-carboxylic Acid (12bi)

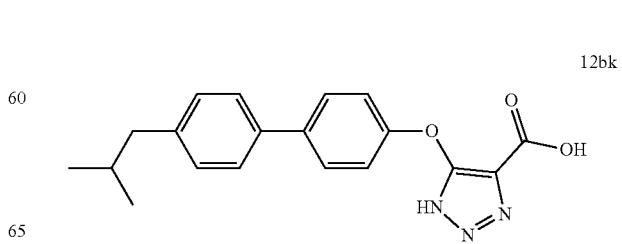

12bi

The title compound was prepared as described in Example 11 using the intermediate of 8t for the cross coupling reaction and anisole for PMB deprotection. ¹H NMR (400 MHz, DMSO-d₆) δ 7.64-7.54 (m, 3H), 7.45 (d, J=8.6 Hz, 2H), 7.38 (d, J=8.6 Hz, 1H), 7.01 (t, J=8.5 Hz, 1H), 1.29 (s, 9H). MS: ES– 354.11 (M–1).

Example 107. Preparation of 5-((3-fluoro-4'-isopropyl-[1,1'-biphenyl]-4-yl)oxy)-1H-1,2,3-triazole-4-carboxylic Acid (12bj)

12bj

The title compound was prepared as described in Example 11 using the intermediate of 8t for the cross coupling reaction and anisole for PMB deprotection. ¹H NMR (400 MHz, DMSO-d₆) δ 7.64-7.55 (m, 3H), 7.40 (d, J=8.5 Hz, 1H), 7.31 (d, J=8.3 Hz, 2H), 7.09 (t, J=8.6 Hz, 1H), 2.91 (m, 1H), 1.22 (m, 2H). MS: ES– 340.10 (M–1).

Example 108. Preparation of 5-((4'-isobutyl-[1,1'-biphenyl]-4-yl)oxy)-1H-1,2,3-triazole-4-carboxylic Acid (12bk)

12bk

The title compound was prepared as described in Example 11 using the intermediate 9a for the cross coupling reaction and anisole for PMB deprotection. $^1$H NMR (400 MHz, DMSO-d$_6$) δ 7.70-7.58 (m, 2H), 7.57-7.50 (m, 2H), 7.27-7.17 (m, 2H), 7.18-7.04 (m, 2H), 2.17-1.60 (m, 1H), 0.87 (d, J=6.6 Hz, 6H). (CH$_2$ of isobutyl overlaps with DMSO-de peak). MS: ES+ 338.14 (M+1).

Example 109. Preparation of 5-((3'-isopropyl-[1,1'-biphenyl]-4-yl)oxy)-1H-1,2,3-triazole-4-carboxylic Acid (12bl)

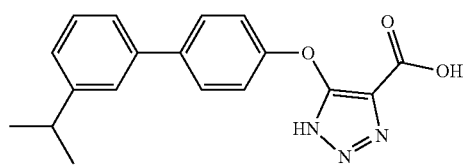

The title compound was prepared as described in Example 11 using the intermediate 9a for the cross coupling reaction and anisole for PMB deprotection. $^1$H NMR (400 MHz, DMSO-d$_6$) δ 7.67-7.57 (m, 2H), 7.47 (s, 1H), 7.44-7.39 (m, 1H), 7.35 (t, J=7.6 Hz, 1H), 7.21 (d, J=7.5 Hz, 1H), 7.19-7.07 (m, 2H), 2.94 (m, 1H), 1.23 (d, J=6.9 Hz, 6H). MS: ES+ 324.15 (M+1).

Example 110. Preparation of 5-((3',4',5'-trifluoro-[1,1'-biphenyl]-4-yl)oxy)-1H-1,2,3-triazole-4-carboxylic Acid (12bm)

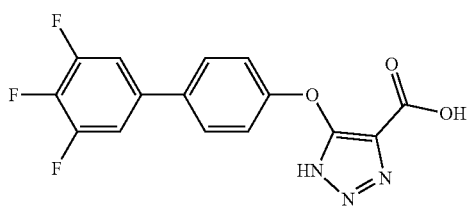

The title compound was prepared as described in Example 11 using the intermediate 9a for the cross coupling reaction and anisole for PMB deprotection. $^1$H NMR (400 MHz, DMSO-d$_6$) δ 7.62 (dd, J=9.9, 7.8 Hz, 4H), 6.95-6.88 (m, 2H), 7.38 (d, J=8.6 Hz, 1H). MS: ES− 334.06 (M−1).

Example 111. Preparation of 5-((4'-isopropyl-[1,1'-biphenyl]-3-yl)oxy)-1H-1,2,3-triazole-4-carboxylic Acid (12bn)

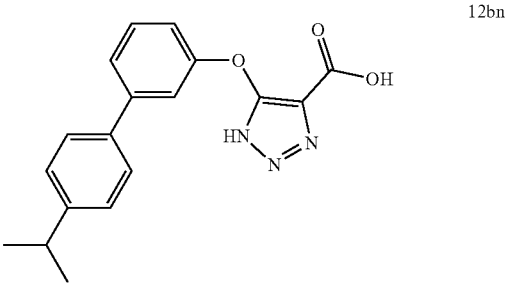 [SMILES: CC(C)c1ccc(-c2cccc(Oc3[nH]nnc3C(=O)O)c2)cc1]

The title compound was prepared as described in Example 11 using the intermediate of 8g for the cross coupling reaction and anisole for PMB deprotection. $^1$H NMR (400 MHz, DMSO-d$_6$) δ 8.00-7.91 (m, 2H), 7.74 (d, J=8.7 Hz, 2H), 7.69 (d, J=6.6 Hz, 2H), 7.17 (d, J=8.7 Hz, 2H). MS: ES− 322.13 (M−1).

Example 112. Preparation of 5-((3'-(trifluoromethyl)-[1,1'-biphenyl]-4-yl)oxy)-1H-1,2,3-triazole-4-carboxylic Acid (12bo)

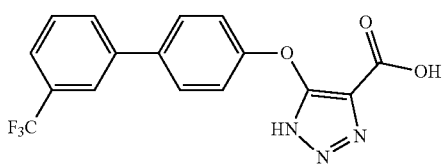

The title compound was prepared as described in Example 11 using the intermediate 9a for the cross coupling reaction and anisole for PMB deprotection. $^1$H NMR (400 MHz, DMSO-d$_6$) δ 8.00-7.91 (m, 2H), 7.74 (d, J=8.7 Hz, 2H), 7.69 (d, J=6.6 Hz, 2H), 7.17 (d, J=8.7 Hz, 2H). MS: ES− 348.08 (M−1).

Example 113. Preparation of 5-((4'-isopropyl-[1,1'-biphenyl]-4-yl)thio)-1H-1,2,3-triazole-4-carboxylic Acid (12 bp)

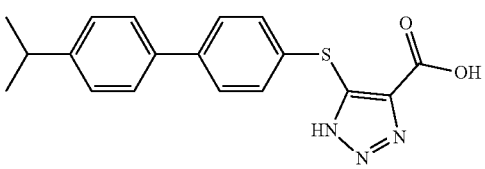

The title compound was prepared as described in Example 11 using the intermediate of 8u for the cross coupling reaction using Pd(Ph$_3$P)$_4$ as catalyst and anisole for PMB deprotection. $^1$H NMR (400 MHz, DMSO-d$_6$) δ 7.70-7.61

(m, 1H), 7.60-7.55 (m, 1H), 7.51 (d, J=8.1 Hz, 1H), 7.33 (d, J=8.3 Hz, 1H), 2.99-2.83 (m, 1H), 1.22 (d, J=6.9 Hz, 3H). MS: ES− 338.14 (M−1).

Example 114. Preparation of 5-((4'-(trifluoromethyl)-[1,1'-biphenyl]-3-yl)oxy)-1H-1,2,3-triazole-4-carboxylic Acid (12bq)

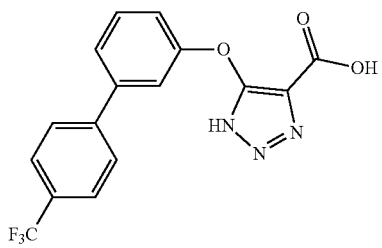

12bq

The title compound was prepared as described in Example 11 using the intermediate 9a for the cross coupling reaction and anisole for PMB deprotection. $^1$H NMR (400 MHz, DMSO-d$_6$) δ 7.88 (d, J=8.2 Hz, 2H), 7.79 (d, J=8.3 Hz, 2H), 7.55-7.44 (m, 3H), 7.12 (d, J=7.6 Hz, 1H). MS: ES− 348.08 (M−1).

Example 115. Preparation of 5-((4'-(trifluoromethyl)-[1,1'-biphenyl]-4-yl)thio)-1H-1,2,3-triazole-4-carboxylic Acid (12br)

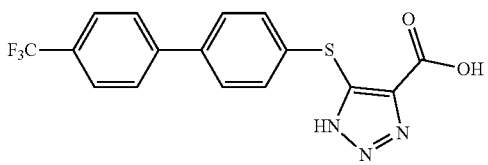

12br

The title compound was prepared as described in Example 11 using the intermediate of 8u for the cross coupling reaction using Pd(Ph$_3$P)$_4$ as catalyst and anisole for PMB deprotection. $^1$H NMR (400 MHz, DMSO-d$_6$) δ 7.89 (m, 2H), 7.82 (m, 2H), 7.75 (d, J=8.0 Hz, 2H), 7.55 (m, 2H). MS: ES− 364.04 (M−1).

Example 116. Preparation of 5-((4'-isopropyl-[1,1'-biphenyl]-4-yl)oxy)-1H-1,2,3-triazole-4-carboxylic Acid Bis Sodium Salt (12bs)

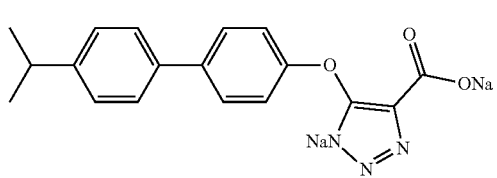

12bs

To a water (40 mL) suspension of compound 12q Example 32 (0.400 g, 1.24 mmol) was added 1 M sodium hydroxide (2.47 mL, 2.47 mmol) to provide a solution which was freeze dried to provide the title compound (0.432 g). $^1$H NMR (400 MHz, DMSO-d$_6$) δ 7.45 (m, 4H), 7.25 (d, J=8.3 Hz, 2H), 7.02-6.60 (m, 2H), 3.15-2.76 (m, 1H), 1.20 (d, J=6.9 Hz, 6H). MS: ES+ 389.98 (M+23).

Example 117. Preparation of 5-(4-(4,4-difluorocyclohexyl)phenoxy)-1H-1,2,3-triazole-4-carboxylic Acid Bis Sodium Salt (8ao)

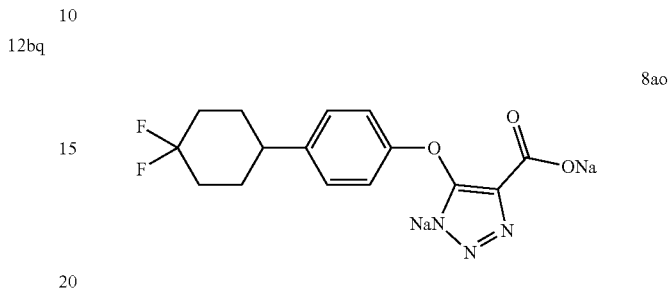

8ao

To a water (40 mL) suspension of compound 8al Example 87 (0.250 g, 0.773 mmol) was added 1 M sodium hydroxide (1.55 mL, 1.55 mmol) to provide a solution which was freeze dried to provide the title compound (0.260 g). $^1$H NMR (400 MHz, DMSO-d$_6$) δ 7.11-6.86 (m, 2H), 6.82-6.34 (m, 2H), 2.76-2.51 (m, 2H), 2.01 (m, 2H), 1.93 (m, 1H), 1.82 (m, 2H), 1.57 (m, 2H). MS: ES+ 389.98 (M+23).

Example 118. Preparation of 5-((4'-(trifluoromethyl)-[1,1'-biphenyl]-4-yl)oxy)-1H-1,2,3-triazole-4-carboxylic Acid Bis Sodium Salt (12bt)

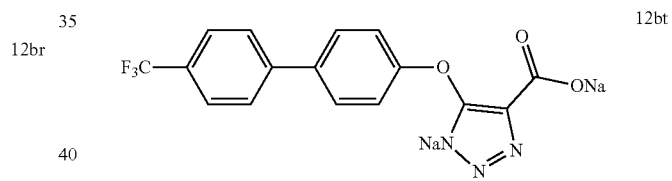

12bt

To a water (50 mL) suspension of compound 12u Example 38 (0.800 g, 2.29 mmol) was added 1 M sodium hydroxide (4.58 mL, 4.58 mmol) to provide a solution which was freeze dried to provide the title compound (0.810 g). $^1$H NMR (400 MHz, DMSO-d$_6$) δ 7.77 (m, 4H), 7.56 (d, J=8.7 Hz, 2H), 6.88 (d, J=8.8 Hz, 2H). MS: ES− 348.01 (M−1).

Example 119. Preparation of 5-(4-(2-fluoropyridin-3-yl)phenoxy)-1H-1,2,3-triazole-4-carboxylic Acid Bis Sodium Salt (12bu)

The title compound was prepared from 12h Example 18 as described in Examples 115-117.

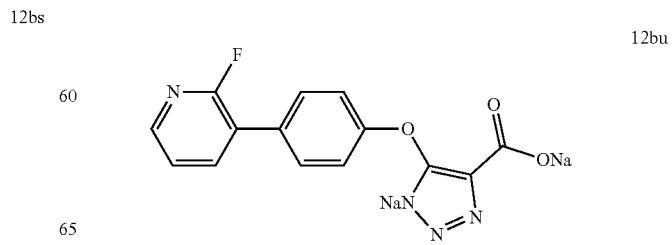

12bu

Example 120. Preparation of 5-[4[4-(3-pyridyl)phenyl]phenoxy]-1H-1,2,3-triazole-4-carboxylic Acid (12bv)

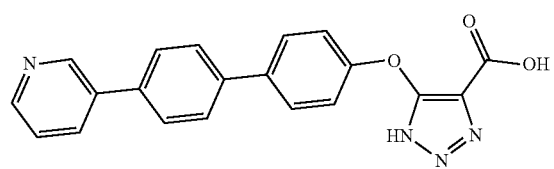

The title compound was prepared as described in Example 11 using the PMB protected ethyl ester intermediate of Example 10. $^1$H NMR (400 MHz, DMSO-$d_6$) δ 9.07 (s, 1H), 8.68 (d, J=4.4 Hz, 1H), 8.41 (d, J=8.1 Hz, 1H), 7.88 (d, J=8.5 Hz, 2H), 7.81 (d, J=8.5 Hz, 2H), 7.77-7.65 (m, 3H), 7.22-7.07 (m, 2H). MS: ES+ 359.10 (M+1).

Example 121. Preparation of 5-((4'-cyclopropyl-[1,1'-biphenyl]-4-yl)oxy)-1H-1,2,3-triazole-4-carboxylic Acid (12bw)

Step 1: Methyl 5-(4-bromophenoxy)-1H-1,2,3-triazole-4-carboxylate (17). To a stirred solution of methyl 5-(4-bromophenoxy)-1-(4-methoxybenzyl)-1H-1,2,3-triazole-4-carboxylate 9a (2 g, 4.78 mmol) and anisole (2.08 mL, 19.1 mmol) in DCM (2 mL) was added TFA (10 mL). The reaction mixture heated at 50° C. for 5 h. The mixture was then concentrated and the residue was suspended in ether-hexane (2 ml-10 mL). The suspension was allowed to stir at rt overnight. The solid was filtered and rinsed with hexanes to provide methyl 5-(4-bromophenoxy)-1H-1,2,3-triazole-4-carboxylate 17 (1.25 g, 88%) as a white solid. $^1$H NMR (400 MHz, CDCl$_3$) δ 7.49 (d, J=8.9 Hz, 2H), 7.10 (d, J=8.9 Hz, 2H), 3.95 (s, 3H).

Step 2: Methyl 5-(4-bromophenoxy)-1-((2-(trimethylsilyl)ethoxy)methyl)-1H-1,2,3-triazole-4-carboxylate and methyl 4-(4-bromophenoxy)-1-((2-(trimethylsilyl)ethoxy)methyl)-1H-1,2,3-triazole-5-carboxylate (18a and 18 b). To a cooled solution of methyl 5-(4-bromophenoxy)-1H-1,2,3-triazole-4-carboxylate 17 (270 mg, 0.906 mmol) in THF (4 mL) was added NaH (60%, 43.5 mg, 1.09 mmol) under argon atmosphere. The mixture was stirred for 20 min, (2-(chloromethoxy)ethyl)trimethylsilane (0.19 mL, 1.09 mmol) was then added in one portion and the reaction mixture stirred for 2 h at rt. The solvent was concentrated and the residue was extracted with EtOAc. The organic phase was washed with water and dried over Na$_2$SO$_4$, filtered and concentrated. The crude product was purified on silica gel cartridge (24 g) using 0 to 40% EtOAc-Hexanes) to provide a mixture of methyl 5-(4-bromophenoxy)-1-((2-(trimethylsilyl)ethoxy)methyl)-1H-1,2,3-triazole-4-carboxylate 18a and methyl 4-(4-bromophenoxy)-1-((2-(trimethylsilyl)ethoxy)methyl)-1H-1,2,3-triazole-5-carboxylate 18b (220 mg, 57%) as a transparent color oil which was used as such for the next step: one isomer is major and the regioselectivity was not established.

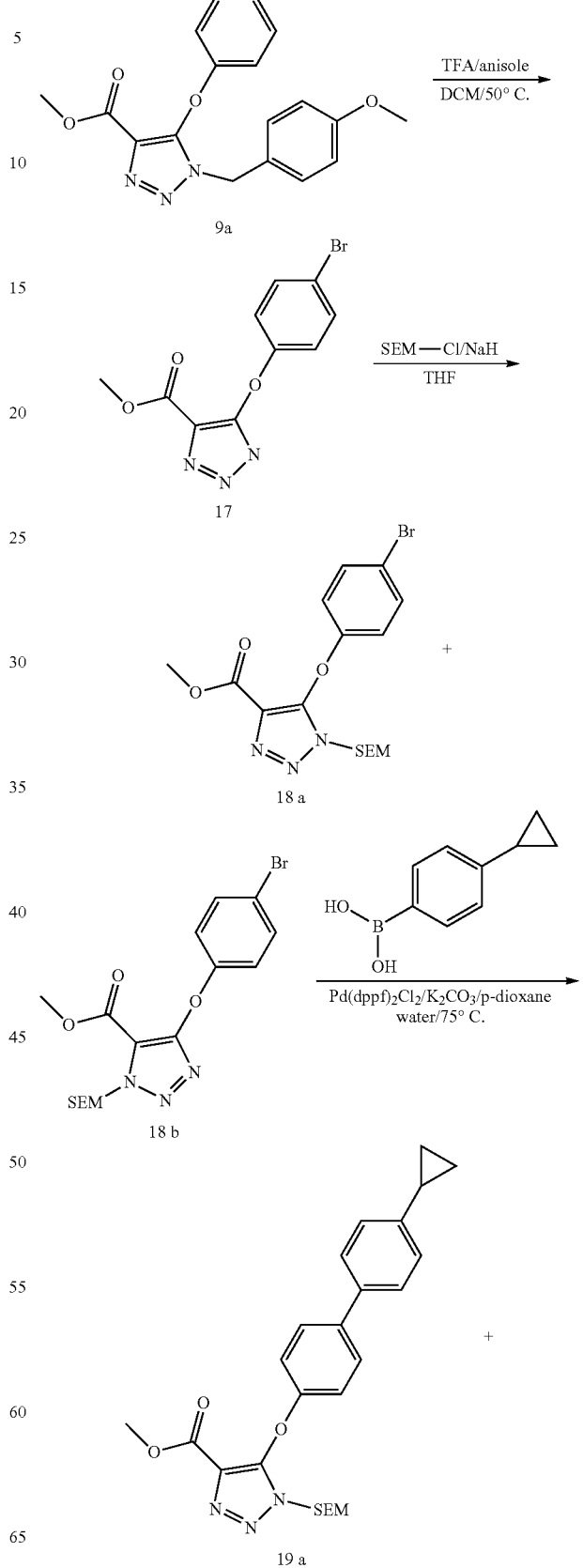

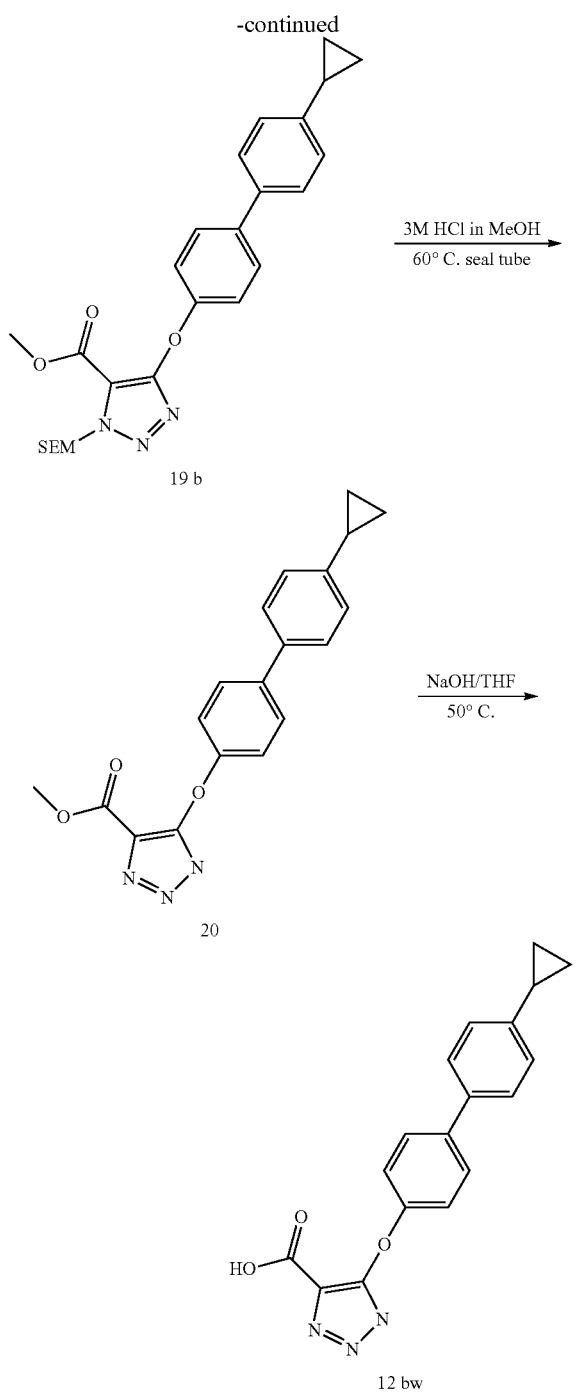

tion mixture was heated at 80° C. for 1.5 h. The solvents were evaporated and the residue was dissolved in EtOAc and washed with water and brine. The organic phase was dried over $Na_2SO_4$, filtered and evaporated. The residue was purified on silica gel (40 g) using EtOAc-hexanes (0-100%) to afford methyl 5-((4'-cyclopropyl-[1,1'-biphenyl]-4-yl)oxy)-1-((2-(trimethylsilyl)ethoxy)methyl)-1H-1,2,3-triazole-4-carboxylate 19a or methyl 4-((4'-cyclopropyl-[1,1'-biphenyl]-4-yl)oxy)-1-((2-(trimethylsilyl)ethoxy)methyl)-1H-1,2,3-triazole-5-carboxylate 19b 150 mg, 63%) as a white solid and single regioisomer. The regiochemistry was not established. $^1$H NMR (400 MHz, $CDCl_3$) δ 7.59-7.48 (m, 2H), 7.46 (d, J=8.3 Hz, 2H), 7.24 (s, 2H), 7.14 (d, J=8.3 Hz, 2H), 5.58 (s, 3H), 3.95 (s, 3H), 3.73-3.58 (m, 2H), 2.00-1.84 (m, 1H), 1.00 (ddd, J=8.2, 6.3, 4.4 Hz, 2H), 0.94-0.81 (m, 2H), 0.74 (dt, J=6.6, 4.7 Hz, 2H), −0.02 (s, 9H).

Step 4: Methyl 5-((4'-cyclopropyl-[1,1'-biphenyl]-4-yl)oxy)-1H-1,2,3-triazole-4-carboxylate (20). Methyl 5-((4'-cyclopropyl-[1,1'-biphenyl]-4-yl)oxy)-1-((2-(trimethylsilyl)ethoxy)methyl)-1H-1,2,3-triazole-4-carboxylate 19a or methyl 4-((4'-cyclopropyl-[1,1'-biphenyl]-4-yl)oxy)-1-((2-(trimethylsilyl)ethoxy)methyl)-1H-1,2,3-triazole-5-carboxylate 19b (33 mg, 0.07 mmol) was dissolved in a solution of HCl 3N in MeOH (1 mL). The reaction mixture was stirred at 60° C. overnight. The solvent was concentrated and the residue was dissolved in EtOAc and washed with aqeuous $NaHCO_3$. The organic phase was collected, dried over $Na_2SO_4$, filtered and concentrated. The residue was purified on a 12 g silica gel cartridge using EtOAc-Hexanes (0 to 80%) to afford methyl 5-((4'-cyclopropyl-[1,1'-biphenyl]-4-yl)oxy)-1H-1,2,3-triazole-4-carboxylate 20 (20 mg) as a white solid. $^1$H NMR (400 MHz, $CDCl_3$) δ 7.57 (d, J=8.6 Hz, 2H), 7.46 (d, J=8.2 Hz, 2H), 7.25 (d, J=8.1 Hz, 2H), 7.14 (d, J=8.1 Hz, 2H), 3.96 (s, 3H), 1.93 (ddd, J=13.3, 8.6, 5.1 Hz, 1H), 1.07-0.93 (m, 2H), 0.73 (q, J=4.7 Hz, 2H).

Step 5: 5-((4'-Cyclopropyl-[1,1'-biphenyl]-4-yl)oxy)-1H-1,2,3-triazole-4-carboxylic acid (12 bw). The title compound was prepared as described in Example 11. $^1$H NMR (400 MHz, Acetone-$d_6$) δ 7.67-7.61 (m, 2H), 7.59-7.50 (m, 2H), 7.25-7.19 (m, 2H), 7.19-7.14 (m, 2H), 1.96 (tt, J=8.4, 5.1 Hz, 1H), 1.02-0.95 (m, 2H), 0.75-0.68 (m, 2H). MS: ES+ 322.13 (M+1).

Example 122. Preparation of 5-((4'-(1-methylcyclopropyl)-[1,1'-biphenyl]-4-yl)oxy)-1H-1,2,3-triazole-4-carboxylic Acid (12bx)

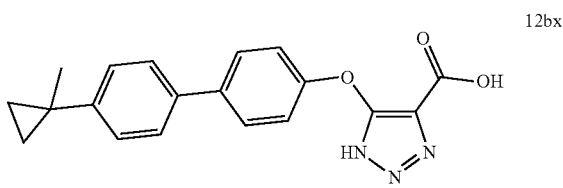 [SMILES: CC1(c2ccc(-c3ccc(Oc4[nH]nnc4C(=O)O)cc3)cc2)CC1]

12bx

Step 3: Methyl 5-((4'-cyclopropyl-[1,1'-biphenyl]-4-yl)oxy)-1-((2-(trimethylsilyl)ethoxy)methyl)-1H-1,2,3-triazole-4-carboxylate or methyl 4-((4'-cyclopropyl-[1,1'-biphenyl]-4-yl)oxy)-1-((2-(trimethylsilyl)ethoxy)methyl)-1H-1,2,3-triazole-5-carboxylate (19a or 19b). To a solution of methyl 5-(4-bromophenoxy)-1-((2-(trimethylsilyl)ethoxy)methyl)-1H-1,2,3-triazole-4-carboxylate 18a and methyl 4-((4-bromophenoxy)-1-((2-(trimethylsilyl)ethoxy)methyl)-1H-1,2,3-triazole-5-carboxylate 18b (220 mg, 0.514 mmol) in p-dioxane (4 mL)-water (0.3 mL) were added (4-cyclopropylphenyl)boronic acid (100 mg, 0.616 mmol) and potassium carbonate (163 mg, 1.18 mmol). After degassing the reaction $Pd(dppf)_2Cl_2 \cdot CH_2Cl_2$ (21 mg) was added. The reac- The title compound was prepared as described in Example 121. $^1$H NMR (400 MHz, DMSO-d6) δ 13.25 (brs, 1H), 7.65-7.57 (m, 2H), 7.56-7.49 (m, 2H), 7.31-7.24 (m, 2H), 7.16-7.08 (m, 2H), 1.39 (s, 3H), 0.89-0.79 (m, 2H), 0.83-0.72 (m, 2H). MS: ES− 334.0 (M−1).

Example 123. Preparation of 5-((4'-(2,2-difluorocyclopropyl)-[1,1'-biphenyl]-4-yl)oxy)-1H-1,2,3-triazole-4-carboxylic Acid (12by)

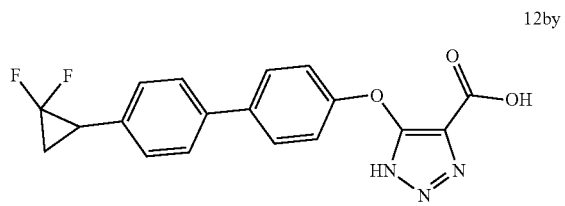 [SMILES: O=C(O)c1nn[nH]c1Oc1ccc(-c2ccc(C3CC3(F)F)cc2)cc1]

The title compound was prepared as described in Example 11 using the intermediate 9a for the cross coupling reaction and anisole for PMB deprotection. ¹H NMR (400 MHz, DMSO-d6) δ 7.68-7.56 (m, 4H), 7.37-7.30 (m, 2H), 7.17-7.08 (m, 2H), 3.03 (ddd, J=13.5, 11.1, 8.5 Hz, 1H), 2.06-1.89 (m, 2H). MS: ES− 356.01 (M−1).

Example 124. Preparation of ((isopropoxycarbonyl)oxy)methyl 1-(((isopropoxy-carbonyl)oxy)methyl)-5-((4'-isopropyl-[1,1'-biphenyl]-4-yl)oxy)-1H-1,2,3-triazole-4-carboxylate (21a) and ((isopropoxycarbonyl)oxy)methyl 1-(((isopropoxycarbonyl)-oxy)methyl)-4-((4'-isopropyl-[1,1'-biphenyl]-4-yl)oxy)-1H-1,2,3-triazole-5-carboxylate (21b)

To a stirred solution of 4-((4'-isopropyl-[1,1'-biphenyl]-4-yl)oxy)-1H-1,2,3-triazole-5-carboxylic acid (12q, 110 mg, 0.34 mmol) in DMA (1.5 mL) was added potassium carbonate (37 mg, 0.268 mmol), stirred at rt for 30 min. and neat chloromethyl isopropyl carbonate (164 mg, 1.07 mmol) was added, heated at 50° C. for 24 h, acidified with aq. 10% citric acid, extracted with ethyl acetate (3×5 mL), combined extracts were washed with brine, dried (Na₂SO₄), and concentrated. The residue was purified on 25 g SiO₂ cartridge using a gradient of ethyl acetate in hexanes (0 to 50%) as eluant to afford a 1:2.5 isomer mixture of the title compound (97 mg, 25.7%) as colorless oil. ¹H NMR (400 MHz, Chloroform-d, minor isomer) δ 7.61-7.54 (m, 2H), 7.50 (dd, J=8.3, 2.0 Hz, 2H), 7.34-7.21 (m, 4H), 6.57 (s, 2H), 5.97 (s, 2H), 5.01-4.84 (m, 2H), 2.95 (hept, J=6.9 Hz, 1H), 1.38-1.22 (m, 18H). ¹H NMR (400 MHz, Chloroform-d, major isomer) δ 7.61-7.53 (m, 2H), 7.53-7.46 (m, 2H), 7.34-7.24 (m, 4H), 6.17 (s, 2H), 6.01 (s, 2H), 4.98-4.85 (m, 2H), 2.96 (hept, J=6.9 Hz, 1H), 1.30 (dd, J=6.6, 5.9 Hz, 18H). MS: ES+ 556.24 (M+1).

Example 125. Preparation of ((isopropoxycarbonyl)oxy)methyl 5-((4'-isopropyl-[1,1'-biphenyl]-4-yl)oxy)-1H-1,2,3-triazole-4-carboxylate (25)

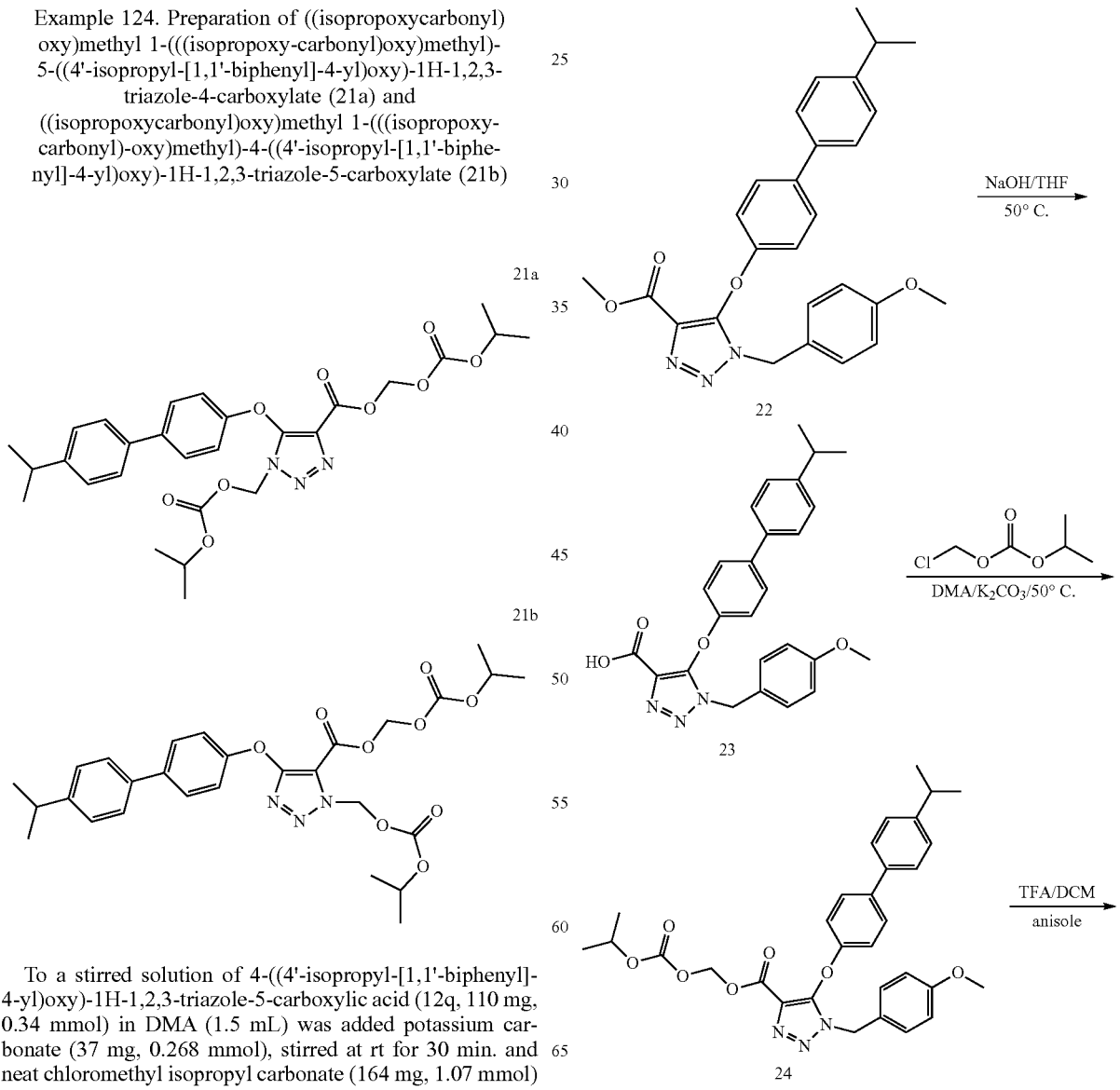

7.34-7.22 (m, 4H), 6.01 (s, 2H), 4.92 (hept, J=6.2 Hz, 1H), 2.95 (hept, J=6.9 Hz, 1H), 1.30 (d, J=3.1 Hz, 6H), 1.28 (d, J=3.8 Hz, 6H). MS: ES+ 440.05 (M+1).

Example 126. Preparation of 5-(4-(4-(2,2-difluorocyclopropyl)cyclohexyl)phenoxy)-1H-1,2,3-triazole-4-carboxylic Acid (31)

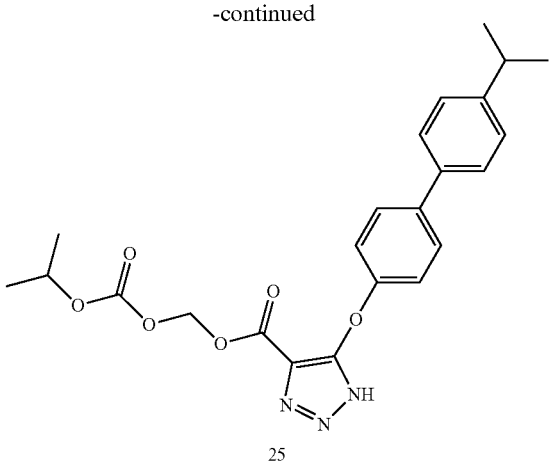

Step 1: 5-((4'-Isopropyl-[1,1'-biphenyl]-4-yl)oxy)-1-(4-methoxybenzyl)-1H-1,2,3-triazole-4-carboxylic acid (23). To a mixture of methyl 5-((4'-isopropyl-[1,1'-biphenyl]-4-yl)oxy)-1-(4-methoxybenzyl)-1H-1,2,3-triazole-4-carboxylate 22 (780 mg, 1.7 mmol) in THF (6.8 mL) was added sodium hydroxide (6.8 mL, 6.8 mmol), heated at 50° C. for 4 h, solvent was partially evaporated on the rotavap, acidified with aq. 1N HCl, filtered off the solids, washed with water (10 mL), dried to afford the title compound 23 (640 mg, 84.6%) as a white solid. ¹H NMR (400 MHz, Chloroform-d) δ 7.47-7.38 (m, 4H), 7.32-7.24 (m, 2H), 7.23-7.15 (m, 2H), 6.83-6.73 (m, 4H), 5.34 (s, 2H), 3.73 (s, 3H), 2.95 (hept, J=6.8 Hz, 1H), 1.28 (d, J=6.8 Hz, 6H). MS: ES– 442.06 (M–1).

Step 2: ((Isopropoxycarbonyl)oxy)methyl 5-((4'-isopropyl-[1,1'-biphenyl]-4-yl)oxy)-1-(4-methoxybenzyl)-1H-1,2,3-triazole-4-carboxylate (24). To a stirred solution of 5-((4'-isopropyl-[1,1'-biphenyl]-4-yl)oxy)-1-(4-methoxybenzyl)-1H-1,2,3-triazole-4-carboxylic acid 23 (330 mg, 0.744 mmol) in DMA (3.0 mL) was added potassium carbonate (77 mg, 0.558 mmol), stirred at rt for 30 min. To the resultant suspension was added neat chloromethyl isopropyl carbonate (170 mg, 1.12 mmol), heated for 6 h at 50° C. until clear solution, cooled to rt, acidified with aq. 10% citric acid, extracted with ethyl acetate (30 mL), washed with brine, dried (Na₂SO₄), and concentrated. The residue was purified on 40 g SiO₂ cartridge using a gradient of ethyl acetate in hexanes (0 to 50%) as eluant to afford the title compound (350 mg, 84.1%) as colorless gum. Rf=0.19 (20% EtOAc in hexanes). ¹H NMR (400 MHz, Chloroform-d) δ 7.50-7.41 (m, 4H), 7.33-7.24 (m, 2H), 7.24-7.16 (m, 2H), 6.85-6.74 (m, 4H), 5.79 (s, 2H), 5.36 (s, 2H), 4.79 (hept, J=6.3 Hz, 1H), 3.74 (s, 3H), 2.95 (hept, J=6.9 Hz, 1H), 1.29 (d, J=7.0 Hz, 6H), 1.21 (d, J=6.3 Hz, 6H). MS: ES+ 560.25 (M+1).

Step 3: ((Isopropoxycarbonyl)oxy)methyl 5-((4'-isopropyl-[1,1'-biphenyl]-4-yl)oxy)-1H-1,2,3-triazole-4-carboxylate (25). To a stirred mixture of ((isopropoxycarbonyl)oxy)methyl 5-((4'-isopropyl-[1,1'-biphenyl]-4-yl)oxy)-1-(4-methoxybenzyl)-1H-1,2,3-triazole-4-carboxylate (175 mg, 0.313 mmol) and anisole (338 mg, 3.13 mmol) in DCM (1.1 mL) was added TFA (5.4 mL), resultant solution was heated at 50° C. for 1.5 h (confirmed by HPLC), cooled to rt, concentrated, dried under high vacuum. The residue was triturated with hexanes and ethyl acetate-hexanes to afford the title compound 25 (97 mg, 70.6%) as a white solid. Rf=0.19 (20% EtOAc in hexanes). ¹H NMR (400 MHz, Chloroform-d) δ 7.61-7.53 (m, 2H), 7.53-7.45 (m, 2H),

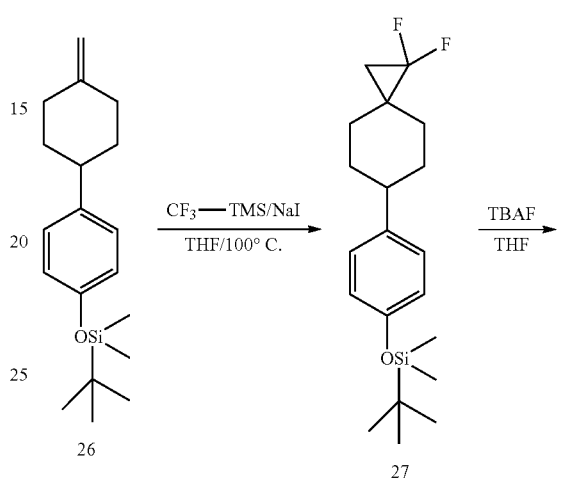

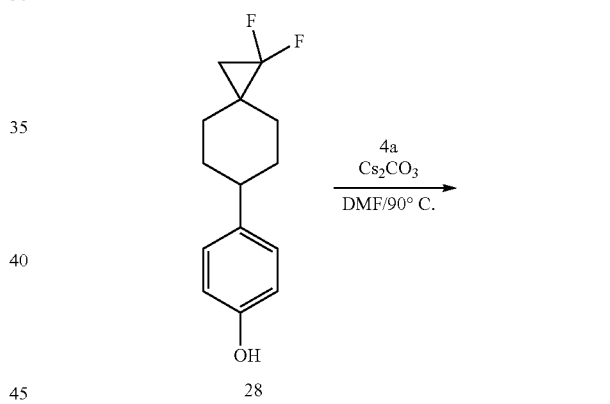

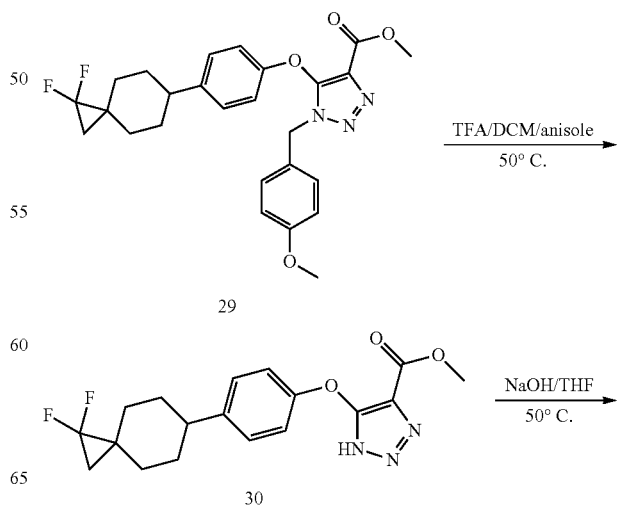

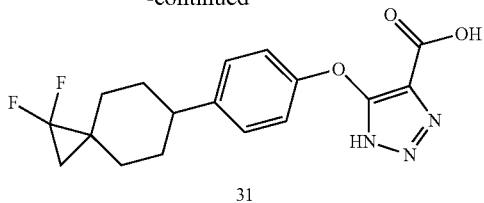

31

Step 1: tert-butyl(4-(1,1-difluorospiro[2.5]octan-6-yl)phenoxy)dimethylsilane (27). In a sealed tube containing tert-butyldimethyl(4-(4-methylenecyclohexyl)phenoxy)silane 26 (3 g, 9.92 mmol) were added dry THF (60 mL), and sodium iodide (438 mg, 2.93 mmol). The reaction mixture was degassed and under argon was added neat trimethyl(trifluoromethyl)silane (7.37 mL, 49.8 mmol). The mixture was heated at 100° C. for 3 hr followed by the addition of another equivalent of sodium iodide and stirred at 100° C. for 4 h. The reaction mixture was concentrated and purified on a 40 g silica gel column by using 10% ethyl acetate in hexane to afford the title compound 27 (2 g, 5.67 mmol). $^1$H NMR (400 MHz, CDCl$_3$) δ 7.06 (m, 2H), 6.81-6.72 (m, 2H), 2.51 (m, 1H), 1.96-1.73 (m, 4H), 1.62-1.42 (m, 4H), 1.10-1.01 (m, 2H), 0.98 (s, 9H), 0.19 (s, 6H).

Step 2: 4-(1,1-difluorospiro[2.5]octan-6-yl)phenol (28). To a stirred solution of tert-butyl(4-(1,1-difluorospiro[2.5]octan-6-yl)phenoxy)dimethylsilane 27 (2 g, 5.67 mmol) in THF (20 mL) was added tetrabutylammonium fluoride 1M (17 mL, 17 mmol). After a period of 2 hr, the reaction mixture was concentrated and purified on combiflash using hexane/ethylacetate 0-30% to afford the title compound 28 (1.2 g). $^1$H NMR (400 MHz, CDCl$_3$) δ 7.14-7.07 (m, 2H), 6.83-6.76 (m, 2H), 2.52 (m, 1H), 1.94-1.74 (m, 4H), 1.61-1.43 (m, 4H), 1.10-1.02 (m, 2H).

Step 3: Methyl 5-(4-(1,1-difluorospiro[2.5]octan-6-yl)phenoxy)-1-(4-methoxy-benzyl)-1H-1,2,3-triazole-4-carboxylate (29). To a mixture of 4-(1,1-difluorospiro[2.5]octan-6-yl)phenol 28 (1.22 g, 5.11 mmol) in DMF (12 mL) was added at 0° C. cesium carbonate (3.47 g, 6.39 mmol). After a period of 45 min at room temperature, the reaction mixture was cooled to 0° C. and a solution of methyl 5-chloro-1-(4-methoxybenzyl)-1H-1,2,3-triazole-4-carboxylate 4a (1.20 g, 4.26 mmol) in DMF (5 mL) was added. The resulting mixture was heated at 90° C. for 6 h. The reaction mixture was poured in cold water and extracted with ethyl acetate. The organic phase was collected, dried over sodium sulfate, filtered and evaporated. The mixture was purified on a 40 g column with 0-60% in hexane/ethylacetate to afford the title compound 29 (260 mg). $^1$H NMR (400 MHz, CDCl$_3$) δ 7.19 (m, 2H), 7.11 (m, 2H), 6.75 (m, 4H), 5.33 (s, 2H), 3.76 (s, 3H), 3.73 (s, 3H), 2.55 (m, 1H), 1.94-1.75 (m, 4H), 1.58-1.44 (m, 4H), 1.05 (m, 2H).

Step 4: Methyl 5-(4-(1,1-difluorospiro[2.5]octan-6-yl)phenoxy)-1H-1,2,3-triazole-4-carboxylate (30). A mixture of methyl 5-(4-(1,1-difluorospiro[2.5]octan-6-yl)phenoxy)-1-(4-methoxybenzyl)-1H-1,2,3-triazole-4-carboxylate 29 (260 mg, 0.538 mmol) and anisole (292 μL, 2.69 mmol) in DCM/TFA (1 mL/2 mL) was stirred at 50° C. for 3 h. The reaction mixture was concentrated under reduced pressure and purified on combiflash 25 g silica gel column using hexane and ethylacetate to afford the title compound 30 (140 mg). $^1$H NMR (400 MHz, CD$_3$OD) δ 7.25 (d, J=8.6 Hz, 2H), 7.04 (d, J=8.6 Hz, 2H), 3.85 (s, 3H), 2.62 (m, 1H), 1.86 (m, 4H), 1.69-1.42 (m, 4H), 1.17-1.06 (m, 2H).

Step 5: 5-(4-(1,1-Difluorospiro[2.5]octan-6-yl)phenoxy)-1H-1,2,3-triazole-4-carboxylic acid (31). To a stirred solution of methyl 5-(4-(1,1-difluorospiro[2.5]octan-6-yl)phenoxy)-1H-1,2,3-triazole-4-carboxylate 30 (140 mg, 0.385 mmol) in THF (5 mL) was added 1 M sodium hydroxide (1.16 mL). The reaction was stirred at 50° C. for 18 hrs. The THF was evaporated and the aqueous layer washed three times with ethyl acetate. The aqueous layer was diluted with water (5 mL) and acidified by using 1 M HCl to pH 2. The resulting solid was filtered and washed with water to afford the title compound 31 (35 mg). $^1$H NMR (400 MHz, DMSO-d$_6$) δ 7.23 (m, 2H), 6.99 (m, 2H), 2.57 (m, 1H), 1.79 (m, 4H), 1.62-1.32 (m, 4H) 1.22 (m, 2H). MS: ES– 348.31 (M−1).

Example 127. Preparation of 5-((4'-(3,3-difluorocyclobutyl)-[1,1'-biphenyl]-4-yl)oxy)-1H-1,2,3-triazole-4-carboxylic Acid (36)

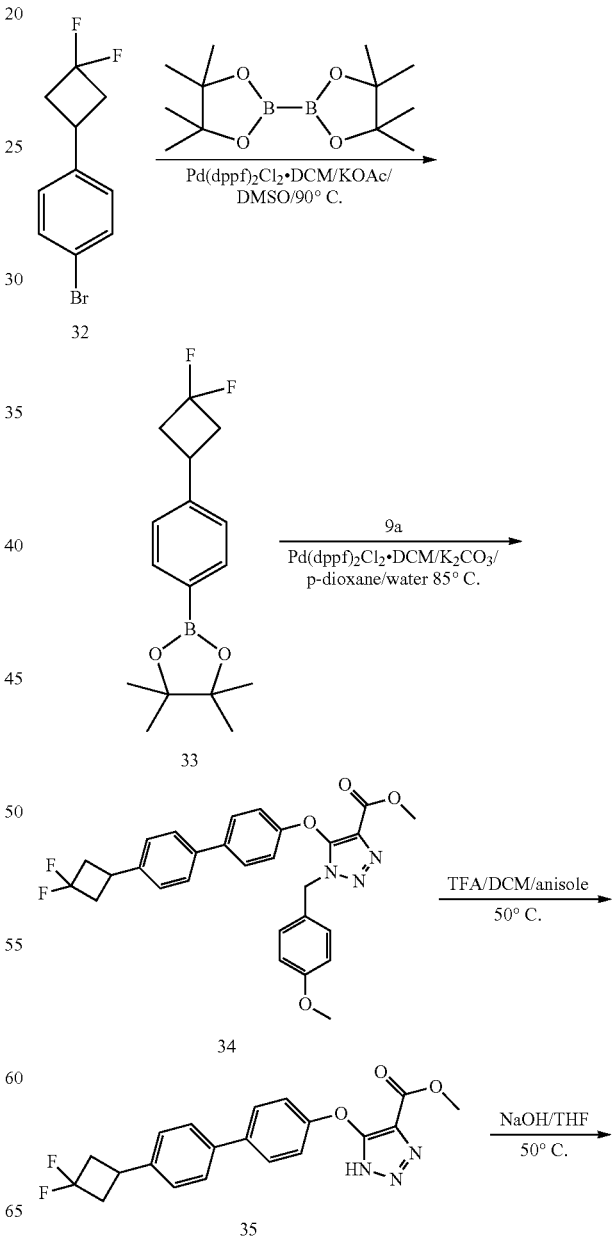

-continued

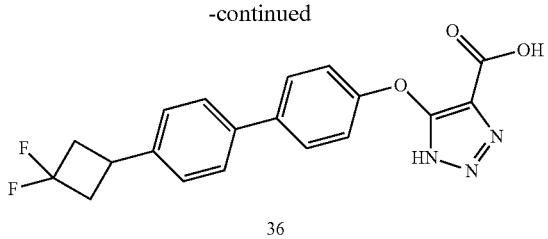

36

Step 1: 2-(4-(3,3-Difluorocyclobutyl)phenyl)-4,4,5,5-tetramethyl-1,3,2-dioxaborolane (33). To a mixture of 1-bromo-4-(3,3-difluorocyclobutyl)benzene 32 (1.7 g, 6.88 mmol) (J. Med. Chem. 2017, 60, 9769-9789), 3-(4-(4,4,5,5-tetramethyl-1,3,2-dioxaborolan-2-yl)phenyl)cyclobutanone (2.27 mg, 8.94 mmol) and potassium acetate (2.03 g, 20.6 mmol) was added DMSO (15 mL). The mixture was purged with argon gas for 5 min, to this mixture was added Pd(dppf)$_2$Cl$_2$.CH2Cl2 (281 mg, 0.344 mmol) and the mixture heated at 90° C. for 3.30 hrs. The mixture was cooled to room temperature, diluted with water (25 mL) and extracted with EtOAc (2×40 mL). The combined organics were washed with water (20 mL), brine, dried, and concentrated. The residue was purified on SiO$_2$ cartridge using 0 to 20% EtOAc-hexanes to afford the title compound 33 (1.2 g) as a white solid. $^1$H NMR (400 MHz, CDCl$_3$) δ 7.78 (d, J=8.0 Hz, 2H), 7.25 (d, J=8.1 Hz, 2H), 3.46-3.25 (m, 1H), 3.08-2.89 (m, 2H), 2.80-2.48 (m, 2H), 1.34 (s, 12H).

Step 2: Methyl 5-((4'-(3,3-difluorocyclobutyl)-[1,1'-biphenyl]-4-yl)oxy)-1-(4-methoxybenzyl)-1H-1,2,3-triazole-4-carboxylate (34). To a solution of methyl 5-(4-bromophenoxy)-1-(4-methoxybenzyl)-1H-1,2,3-triazole-4-carboxylate 9a (800 mg, 0.741 mmol) and 2-(4-(3,3-difluorocyclobutyl)phenyl)-4,4,5,5-tetramethyl-1,3,2-dioxaborolane 33 (731 mg, 2.49 mmol) in p-dioxan (6 mL) was added potassium carbonate (359 mg, 2.59 mmol) and water (0.6 mL). After degassing the reaction Pd(dppf)$_2$Cl$_2$.CH$_2$Cl$_2$ (93 mg, 0.115 mmol) was added. The mixture heated at 85° C. for 2 h. The solvents were evaporated, water was added and extracted with EtOAc. The combined organic phase was washed with brine. The organic phase was dried over Na$_2$SO$_4$ and filtered. After concentration the residue was purified on silicagel (40 g) using EtOAc-Hexanes (0-50%) to provide the title compound 34 (492 mg) as a white solid. $^1$H NMR (400 MHz, CDCl$_3$) δ 7.53-7.48 (m, 2H), 7.48-7.42 (m, 2H), 7.34-7.28 (m, 2H), 7.24-7.18 (m, 2H), 6.87-6.80 (m, 2H), 6.80-6.74 (m, 2H), 5.37 (s, 2H), 3.76 (s, 3H), 3.74 (s, 3H), 3.48-3.31 (m, 1H), 3.15-2.94 (m, 2H), 2.88-2.57 (m, 2H).

Step 3: Methyl 5-((4'-(3,3-difluorocyclobutyl)-[1,1'-biphenyl]-4-yl)oxy)-1H-1,2,3-triazole-4-carboxylate (35). The title compound 35 was prepared as described for the preparation of compound 31. $^1$H NMR (400 MHz, CDCl$_3$) δ 11.21 (s, 1H), 7.74-7.44 (m, 4H), 7.38-7.26 (m, 4H), 3.97 (s, 3H), 3.55-3.31 (m, 1H), 3.11-2.92 (m, 2H), 2.86-2.56 (m, 2H).

Step 4: 5-((4'-(3,3-Difluorocyclobutyl)-[1,1'-biphenyl]-4-yl)oxy)-1H-1,2,3-triazole-4-carboxylic acid (36). The title compound was prepared as described for the synthesis of compound 31. $^1$H NMR (400 MHz, Acetone-d$_6$) δ 7.74-7.54 (m, 4H), 7.42 (d, J=8.2 Hz, 2H), 7.30-7.15 (m, 2H), 3.50 (m, 1H), 3.14-2.96 (m, 2H), 2.83-2.55 (m, 2H). MS: ES– 370.34 (M–1).

Example 128. Preparation of (5-Methyl-2-oxo-1,3-dioxol-4-yl)methyl 5-((4'-isopropyl-[1,1'-biphenyl]-4-yl)oxy)-1H-1,2,3-triazole-4-carboxylate (38)

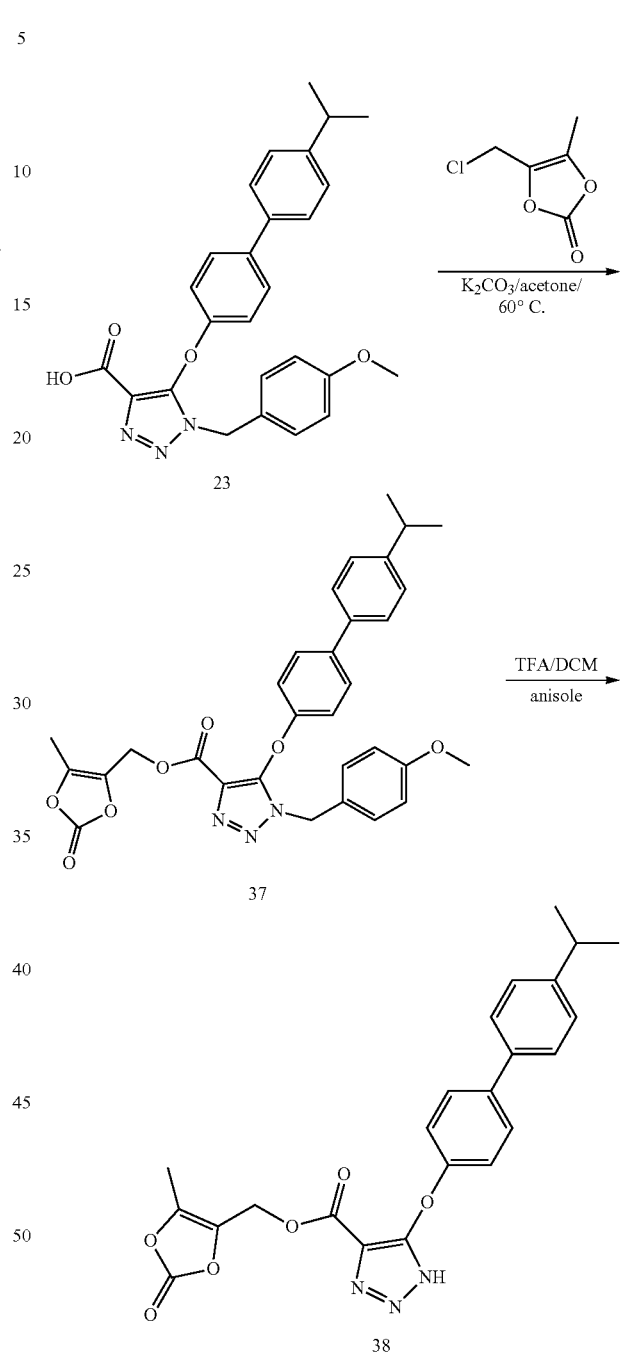

Step 1: (5-Methyl-2-oxo-1,3-dioxol-4-yl)methyl 5-((4'-isopropyl-[1,1'-biphenyl]-4-yl)oxy)-1-(4-methoxybenzyl)-1H-1,2,3-triazole-4-carboxylate (37). To a stirred solution of 5-((4'-isopropyl-[1,1'-biphenyl]-4-yl)oxy)-1-(4-methoxybenzyl)-1H-1,2,3-triazole-4-carboxylic acid 23 (100 mg, 0.225 mmol), prepared as described in Example 125, in acetone (5 mL) in sealed tube was added potassium carbonate (93.5 mg, 676 µmol) and stirred for 30 min at rt. To the previous mixture was added 4-chloromethyl-5-methyl-1,3 dioxol-2-one (36.8 mg, 0.676 mmol). After a period of 16 hrs at 60° C., the reaction mixture was filtered, concentrated and purified on combiflash using 25 g silica gel column and eluting with 0-100% hexane/ethylacetate to afford the title compound 37 (50 mg). 47.9% yield. $^1$H NMR (400 MHz, Acetone-d$_6$) δ 7.60-7.50 (m, 4H), 7.34 (m, 2H), 7.28 (m, 2H), 6.99-6.91 (m, 2H), 6.85 (m, 2h), 5.54 (s, 2H), 4.95 (s, 2H), 3.73 (s, 3H), 3.04-2.90 (m, 1H), 2.01 (s, 3H), 1.26 (t, J=6.1 Hz, 6H).

Step 2: (5-Methyl-2-oxo-1,3-dioxol-4-yl)methyl 5-((4'-isopropyl-[1,1'-biphenyl]-4-yl)oxy)-1H-1,2,3-triazole-4-carboxylate (38). The title compound was prepared as described in step 3 of Example 125. $^1$H NMR (400 MHz, DMSO-d$_6$) δ 7.66-7.57 (m, 2H), 7.52 (m, 2H), 7.30 (m, 2H), 7.18-7.07 (m, 2H), 5.14 (s, 2H), 2.90 (m, 1H), 2.10 (s, 3H), 1.21 (d, J=6.9 Hz, 6H)). MS: ES– 434.30 (M–1).

Example 129. Preparation of 5~((4'-(2-methylpyridin-4~yl)-[1,1'-biphenyl]-4-yl)oxy)-1H-1,2,3-triazole-4-carboxylic Acid (12bz)

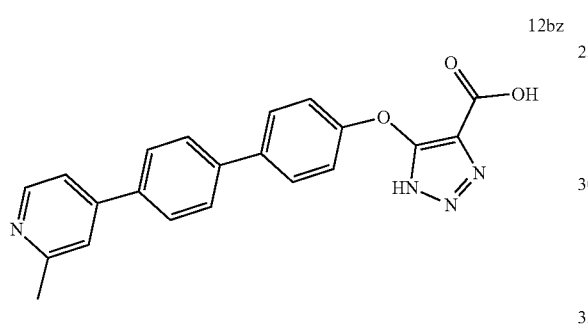

12bz

The title compound was prepared as described in Example 15. $^1$H NMR (400 MHz, DMSO-d$_6$) δ 8.63 (d, J=5.7 Hz, 1H), 8.08-7.92 (m, 3H), 7.84 (d, J=8.4 Hz, 3H), 7.76 (d, J=8.8 Hz, 2H), 7.18 (d, J=8.8 Hz, 2H), 2.62 (s, 3H). MS: ES+ 373.21 (M+1).

Example 130. Preparation of 5-(4-(2,2-difluorocyclopropyl)phenoxy)-1H-1,2,3-triazole-4-carboxylic Acid (8ao)

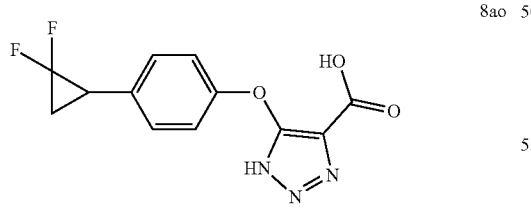

8ao

The title compound was prepared as described in the previous example 1 and 2 using methyl 5-chloro-1-(4-methoxybenzyl)-1H-1,2,3-triazole-4-carboxylate 4a but using Cs$_2$CO$_3$/DMF and anisole for the PMB deprotection. $^1$H NMR (400 MHz, methanol-d$_4$) δ 7.25 (d, J=8.7 Hz, 2H), 7.08 (d, J=8.7 Hz, 2H), 2.84 (td, J=12.4, 8.2 Hz, 1H), 2.02-1.78 (m, 1H), 1.76-1.55 (m, 1H). MS: ES– 280.24 (M–1).

Example 131. Preparation of 5-(4-(3,3-difluorocyclopentyl)phenoxy)-1H-1,2,3-triazole-4-carboxylic Acid (8ap)

Step 1: 4-(3,3-Difluorocyclopentyl)phenol (40)

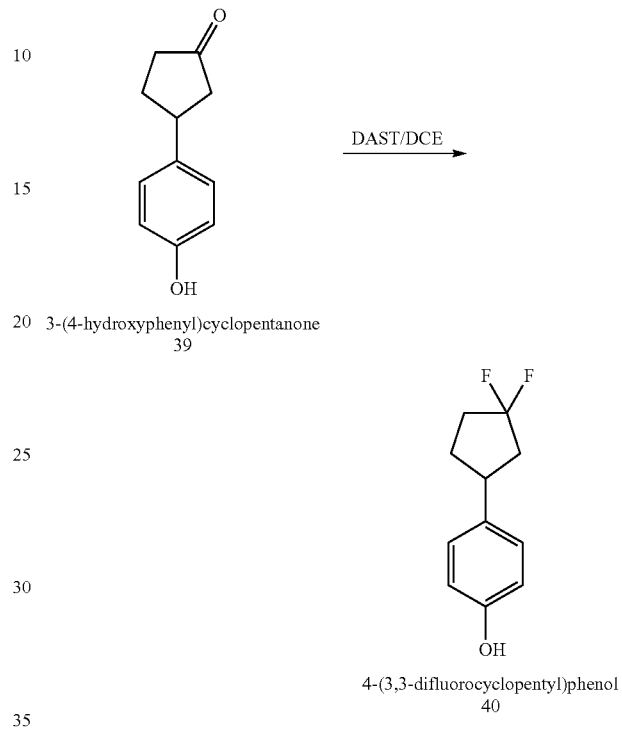

3-(4-hydroxyphenyl)cyclopentanone
39

4-(3,3-difluorocyclopentyl)phenol
40

To a solution of 3-(4-hydroxyphenyl)cyclopentanone (440 mg, 2.5 mmol) in DCE (4 mL) was added DAST. After a period of four days the reaction mixture was diluted with DCM (5 mL) and added to a saturated solution of sodium bicarbonate. The organic phase was collected, dried over sodium sulfate, filtered and evaporated. The mixture was purified on combiflash using 40 g silica gel column with hexane to 40% ethyl acetate to afford the title compound (260 mg) (52%).

Step 2: 5-(4-(3,3-Difluorocyclopentyl)phenoxy)-1H-1,2,3-triazole-4-carboxylic Acid (8ap)

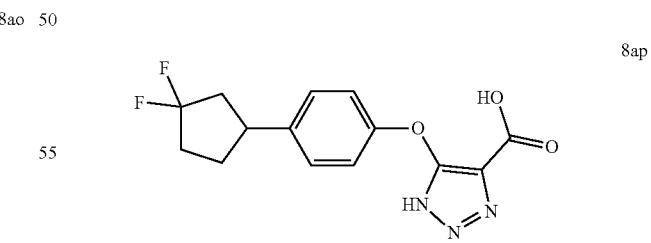

8ap

The title compound was prepared from phenol 40 as described in the previous example 1 and 2 using methyl 5-chloro-1-(4-methoxybenzyl)-1H-1,2,3-triazole-4-carboxylate 4a but anisole for the PMB deprotection. $^1$H NMR (400 MHz, chloroform-d) δ 7.34 (m, 2H), 7.16-7.01 (m, 2H), 3.46-3.26 (m, 1H), 2.53 (m, 1H), 2.42-2.10 (m, 4H), 1.97-1.77 (m, 1H). MS: ES– 308.39 (M–1).

Example 132. Inhibition of Glycolate Oxidase

Figure 2:
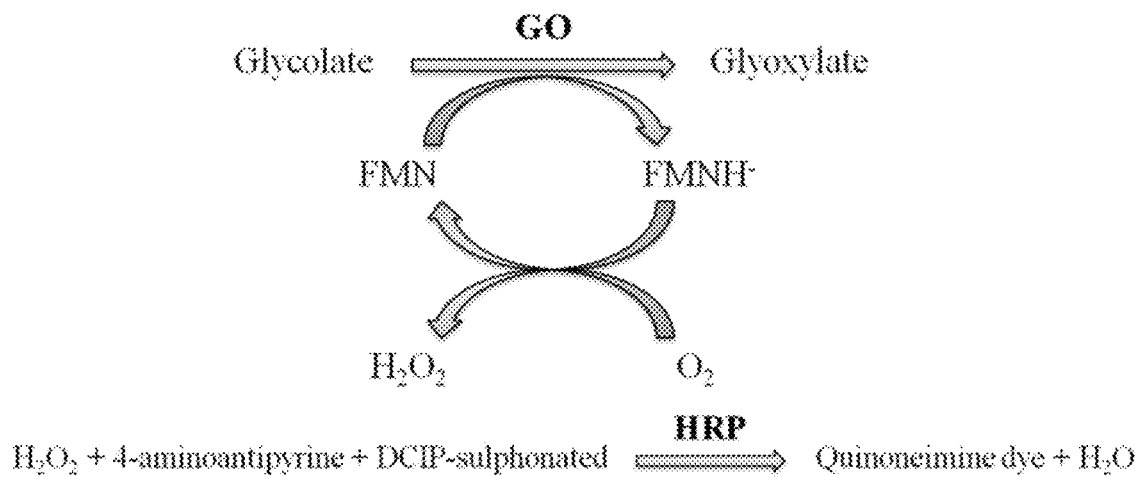
FIG. 2 shows the catalytic reactions used for assaying glycolate oxidase activity.

The catalytic reactions used for assaying glycolate oxidase activity in the presence of compounds according to the present disclosure are outlined in FIG. 2. Glycolate oxidase (GO)-catalyzed conversion of glycolate to glyoxylate (top reaction), with the concomitant reduction of the cofactor flavin mononucleotide (FMN), uses molecular oxygen ($O_2$) for recovering its oxidative state, releasing hydrogen peroxide ($H_2O_2$). The Trinder reaction (bottom reaction), in which horseradish peroxidase (HRP) uses hydrogen peroxide, 4-aminoantipyrine and a phenol derivative (sulphonated DCIP) to generate a quinoneimine dye that is spectrophotometrically measured.

Human glycolate oxidase (hGO) expression. BL21 (DE3) *E. coli* transformed with recombinant pET-15b expression vector with the N-terminal His-tag human Hao1 cDNA was grown in LB medium in the presence of 0.1 mg/ml ampicillin. For purification of recombinant human glycolate oxidase (hGO) expressed in BL21 *E. coli*, bacteria pellets were thawed and re-suspended in 2 ml lysis buffer (50 mM $NaH_2PO_4$, 300 mM NaCl, 10 mM imidazole, 50 μM FMN, pH 7.5), and then treated for 30 minutes with 1 mM PMSF for protease inhibition, 0.1% Triton X-100 and 0.2 mg/ml lysozyme to break cellular membranes. After sonication, cells were centrifuged and the supernatant containing the total cellular extract (pre-column fraction) was loaded into a Ni-NTA agarose column and incubated for 30 minutes at 4° C. to allow binding of the 6 histidine tail of recombinant GO protein to the nickel ions. The column was washed with two bed volumes of lysis buffer with 20 mM imidazole to eliminate unbound proteins (wash fraction). GO was eluted using the same buffer with 300 mM imidazole. Fraction containing purified GO was dialyzed against 300 ml of dialysis buffer (50 mM $NaH_2PO_4$, 300 mM NaCl, pH 7.5) at 4° C. in agitation overnight, and then kept at 4° C. in darkness. Protein were quantified by the bicinchoninic acid (BCA) assay.

Enzymatic assays. Enzymatic activity of hGO was determined in the presence of glycolate as substrate (40 mM glycolic acid) and phosphate buffer (50 mM $KPO_4$, 0.1 mM EDTA, pH 7). The production of glyoxylate was indirectly measured by the quantification of hydrogen peroxide formed during the first oxidation reaction. This hydrogen peroxide reacted with 4.9 mM 4-aminoantipyrine and 0.1 mM sulphonated 2,4-dichlorophenolindophenol in a coupled horseradish peroxidase (HRP) reaction that yields a quinoneimine dye (FIG. 1) measured at 515 nm (Trinder reaction). Enzymatic activity was calculated at 1 minute after initiation of the Trinder reaction. Results of the enzymatic assay for the compounds of this invention are shown in Table 1.

TABLE 1

In vitro inhibition of human glycolate oxidase by compounds of the invention.

| Example | Compound No. | % Inhibition[1] |
|---|---|---|
| 1 | 8a | + |
| 2 | 8b | +++ |
| 3 | 8c | + |
| 4 | 8d | +++ |
| 5 | 8e | + |
| 6 | 8f | +++ |
| 7 | 8g | ++ |
| 8 | 8h | ++ |
| 9 | 8i | + |
| 10 | 8j | +++ |
| 11 | 12a | ++ |
| 12 | 12b | +++ |
| 13 | 12c | +++ |
| 14 | 12d | ++ |
| 15 | 12e | +++ |
| 16 | 12f | +++ |
| 17 | 12g | + |
| 18 | 12h | +++ |
| 19 | 12i | +++ |
| 20 | 12j | ++ |
| 21 | 12k | +++ |
| 22 | 12l | ++ |
| 23 | 12m | +++ |
| 24 | 16a | +++ |
| 25 | 16b | ++ |
| 26 | 16c | ++ |
| 27 | 16d | ++ |
| 28 | 16e | ++ |
| 29 | 12n | ++ |
| 30 | 12o | +++ |
| 31 | 12p | +++ |
| 32 | 12q | +++ |
| 33 | 12r | +++ |
| 34 | 12s | ++ |
| 35 | 12t | ++ |
| 36 | 8k | +++ |
| 37 | 16f | +++ |
| 38 | 12u | +++ |
| 39 | 12v | ++ |
| 40 | 16g | +++ |
| 41 | 12x | ++ |
| 42 | 8l | ++ |
| 43 | 8m | ++ |
| 44 | 12y | ++ |
| 45 | 8n | + |
| 46 | 8o | +++ |
| 47 | 8p | ++ |
| 48 | 8q | +++ |
| 49 | 8r | +++ |
| 50 | 8s | +++ |
| 51 | 8t | +++ |
| 52 | 8u | ++ |
| 53 | 8v | +++ |
| 54 | 8x | + |
| 55 | 12z | +++ |
| 56 | 8y | + |
| 57 | 8z | + |
| 58 | 8aa | +++ |
| 59 | 12aa | +++ |
| 60 | 8ab | +++ |
| 61 | 12ab | +++ |
| 62 | 12ac | ++ |
| 63 | 12ad | ++ |
| 64 | 12ae | ++ |
| 65 | 8ac | + |
| 66 | 8ad | + |
| 67 | 8ae | + |
| 68 | 8af | + |
| 69 | 8ag | ++ |
| 70 | 8ah | + |
| 71 | 8ai | +++ |
| 72 | 12af | +++ |
| 73 | 12ag | +++ |
| 74 | 12ah | +++ |
| 75 | 12ai | +++ |
| 76 | 8aj | +++ |
| 77 | 8ak | ++ |
| 78 | 12aj | +++ |
| 79 | 12ak | +++ |
| 80 | 12al | +++ |
| 81 | 12am | +++ |
| 82 | 12an | +++ |
| 83 | 12ao | +++ |
| 84 | 12ap | ++ |
| 85 | 12aq | ++ |

TABLE 1-continued

In vitro inhibition of human glycolate oxidase by compounds of the invention.

| Example | Compound No. | % Inhibition[1] |
|---|---|---|
| 86 | 12ar | ++ |
| 87 | 8al | ++ |
| 88 | 12as | +++ |
| 89 | 8am | +++ |
| 90 | 12at | +++ |
| 91 | 12au | +++ |
| 92 | 12av | +++ |
| 93 | 12aw | +++ |
| 94 | 12ax | +++ |
| 95 | 8an | + |
| 96 | 12ay | ++ |
| 97 | 12az | ++ |
| 98 | 12ba | +++ |
| 99 | 12bb | +++ |
| 100 | 12bc | +++ |
| 101 | 12bd | +++ |
| 102 | 12be | +++ |
| 103 | 12bf | +++ |
| 104 | 12bg | ++ |
| 105 | 12bh | ++ |
| 106 | 12bi | ++ |
| 107 | 12bj | ++ |
| 108 | 12bk | + |
| 109 | 12bl | + |
| 110 | 12bm | ++ |
| 111 | 12bn | ++ |
| 112 | 12bo | ++ |
| 113 | 12bp | ++ |
| 114 | 12bq | ++ |
| 115 | 12br | ++ |
| 120 | 12bv | ++ |
| 121 | 12bw | +++ |
| 122 | 12bx | ++ |
| 123 | 12by | ++ |
| 126 | 31 | + |
| 127 | 36 | ++ |
| 129 | 12bz | ++ |
| 130 | 8ao | + |
| 131 | 8ap | ++ |

+ = $IC_{50} \geq 200$ nM
++ = $100$ nM $\geq IC_{50} \leq 200$ nM
+++ = $IC_{50} < 100$ nM VII. Exemplary Embodiments Exemplary embodiments provided in accordance with the presently disclosed subject matter include, but are not limited to, the claims and the following embodiments:

1. A compound according to Formula I:

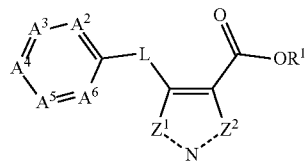

(I)

or a pharmaceutically acceptable salt thereof, wherein:

L is selected from the group consisting of O and S;
$A^2$ is selected from the group consisting of $CR^2$ and N;
$A^3$ is selected from the group consisting of $CR^3$ and N;
$A^4$ is selected from the group consisting of $CR^4$ and N;
$A^5$ and $A^6$ are independently selected from the group consisting of CH and N;

the dashed line connected to $Z^1$ is a double bond, $Z^1$ is N, the dashed line connected to $Z^2$ is a single bond, and $Z^2$ is $NR^6$; or the dashed line connected to $Z^1$ is a single bond, $Z^1$ is $NR^6$, the dashed line connected to $Z^2$ is a double bond, and $Z^2$ is N;

$R^1$ is selected from Ft, unsubstituted $C_{1-6}$ alkyl, substituted $C_{1-6}$ alkyl, —($C_{1-6}$ alkylene)-OC(O)—($C_{1-6}$ alkyl), and —($C_{1-6}$ alkylene)-OC(O)—($C_{1-6}$ alkoxy);

$R^2$ is selected from the group consisting of H and halogen;

$R^3$ and $R^4$ are independently selected from the group consisting of H, halogen, $C_{1-12}$ alkyl, $C_{1-12}$ alkoxy, $C_{6-12}$ aryl, $C_{3-8}$ cycloalkyl, 3- to 12-membered heterocyclyl, and 5- to 12-membered heteroaryl;

$R^3$ is optionally substituted with one or more $R^{3a}$;
$R^4$ is optionally substituted with one or more $R^{4a}$;

each $R^{3a}$ and $R^{4a}$ is independently selected from the group consisting of $C_{1-12}$ alkyl, $C_{1-12}$ alkoxy, $C_{1-12}$ haloalkyl, $C_{1-12}$ haloalkoxy, halogen, —OH, —$CO_2H$, —$SO_3$, —CN, —$NO_2$, —$N_3$, $C_{2-12}$ alkenyl, $C_{2-12}$ alkynyl, $C_{3-8}$ cycloalkyl, $C_{3-8}$ halocycloalkyl, ($C_{6-12}$ aryl)-M-, 3- to 12-membered heterocyclyl, 5- to 12-membered heteroaryl, —N($R^a$)$_2$, —C(O)N($R^a$)$_2$, —OC(O)N($R^a$)$_2$, —S(O)$_2$N($R^a$)$_2$, —$NR^a$C(O)$R^b$, —C(O)$R^b$, and —OC(O)$R^b$;

$R^5$ is selected from the group consisting of H, unsubstituted $C_{1-6}$ alkyl, substituted $C_{1-6}$ alkyl, $C_{2-7}$ acyl, —($C_{1-6}$ alkylene)-OC(O)—($C_{1-6}$ alkyl), and —($C_{1-6}$ alkylene)-OC(O)—($C_{1-6}$ alkoxy);

each M is independently selected from the group consisting of a covalent bond, $NR^a$, O, S, $C_{1-6}$ alkylene, and 2- to 6-membered heteroalkylene;

each $R^a$ is independently selected from the group consisting of H and $C_{1-6}$ alkyl; and each $R^b$ is independently selected from the group consisting of $C_{1-6}$ alkyl and $C_{1-6}$ alkoxy;

provided that if L is O, $A^2$ is $CR^2$, $A^3$ is $CR^3$, $A^4$ is $CR^4$, and $A^5$ and $A^6$ are CH, then:
at least one of $R^2$, $R^3$, and $R^4$ is other than H,
$R^2$ is other than chloro or fluoro when $R^3$ and $R^4$ are H,
$R^3$ is other than chloro, fluoro, methyl, methoxy, trifluoromethyl, or —OH when $R^2$ and $R^4$ are H,
$R^4$ is other than methyl, ethyl, isopropyl, tert-butyl, methoxy, ethoxy, acetoxy, fluoro, or hydroxy when $R^2$ and $R^3$ are H, and
$R^4$ is other than fluoro when $R^2$ is fluoro and $R^3$ is H;

provided that if L is O, $A^2$ is $CR^2$, $A^3$ is N, $A^4$ is $CR^4$, and $A^5$ and $A^6$ are CH, then at least one of $R^2$ and $R^4$ is other than H; and provided that if L is S, $A^2$ is $CR^2$, $A^3$ is $CR^3$, $A^4$ is $CR^4$, and $A^5$ and $A^6$ are CH, then:
$R^4$ is other than methoxy, 4-bromophenyl, or 4-fluorophenyl when $R^2$ and $R^3$ are H, and
$R^3$ is other than 4-bromophenyl or 4-fluorophenyl when $R^2$ and $R^4$ are H.

2. The compound of embodiment 1, or a pharmaceutically acceptable salt thereof, wherein the dashed line connected to $Z^1$ is a double bond, $Z^1$ is N, the dashed line connected to $Z^2$ is a single bond, and $Z^2$ is $NR^6$.

3. The compound of embodiment 1, or a pharmaceutically acceptable salt thereof, wherein the dashed line connected to $Z^1$ is a single bond, $Z^1$ is $NR^6$, the dashed line connected to $Z^2$ is a double bond, and $Z^2$ is N.

4. The compound of any one of embodiments 1-3, or a pharmaceutically acceptable salt thereof, wherein $R^6$ is H.

5. The compound of any one of embodiments 1-3, or a pharmaceutically acceptable salt thereof, wherein $R^8$ is selected from the group consisting of $C_{2-7}$ acyl, —($C_{1-6}$ alkylene)-OC(O)—($C_{1-6}$ alkyl), and —($C_{1-6}$ alkylene)-OC(O)—($C_{1-6}$ alkoxy).

6. The compound of embodiment 1, or a pharmaceutically acceptable salt thereof, having a structure according to Formula Ia:

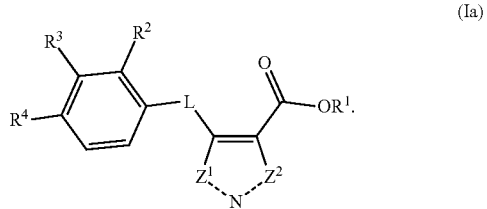

(Ia)

7. The compound of embodiment 1 or embodiment 6, or a pharmaceutically acceptable salt thereof, wherein L is O.

8. The compound of embodiment 1 or embodiment 6, or a pharmaceutically acceptable salt thereof, wherein L is S.

9. The compound of any one of embodiments 1-8, or a pharmaceutically acceptable salt thereof, wherein $R^2$ and $R^3$ are independently selected from the group consisting of H and halogen.

10. The compound of any one of embodiments 1-9, or a pharmaceutically acceptable salt thereof, wherein $R^2$ is halogen and $R^3$ is H.

11. The compound of embodiment 10, or a pharmaceutically acceptable salt thereof, wherein $R^4$ is H.

12. The compound of any one of embodiments 1-9, or a pharmaceutically acceptable salt thereof, wherein $R^2$ is H and $R^3$ is halogen.

13. The compound of embodiment 12, or a pharmaceutically acceptable salt thereof, wherein $R^4$ is H.

14. The compound of embodiment 12, or a pharmaceutically acceptable salt thereof, wherein $R^4$ is halogen.

15. The compound of any one of embodiments 1-9, or a pharmaceutically acceptable salt thereof, wherein $R^2$ and $R^3$ are H.

16. The compound of embodiment 15, or a pharmaceutically acceptable salt thereof, wherein $R^4$ is selected from the group consisting of halogen, $C_{1-12}$ alkyl, $C_{6-12}$ aryl, 3- to 12-membered heterocyclyl, and 5- to 12-membered heteroaryl, each of which is optionally substituted with one or more $R^{4a}$.

17. The compound of embodiment 16, or a pharmaceutically acceptable salt thereof, wherein $R^4$ is selected from the group consisting of phenyl and biphenyl, each of which is optionally substituted with one or more $R^{4a}$.

18. The compound of embodiment 17, or a pharmaceutically acceptable salt thereof, wherein $R^{4a}$ is selected from the group consisting of $C_{1-12}$ alkyl, $C_{1-12}$ alkoxy, $C_{1-12}$ haloalkyl, $C_{1-12}$ haloalkoxy, halogen, —CN, 5- to 12-membered heteroaryl, and —C(O)N($R^a$)$_2$.

19. The compound of embodiment 1, or a pharmaceutically acceptable salt thereof, wherein $A^3$ is N.

20. The compound of embodiment 19, or a pharmaceutically acceptable salt thereof, wherein $A^2$ is $CR^2$, $A^4$ is $CR^4$, $A^5$ is CH, and $A^6$ is CH.

21. The compound of embodiment 19 or embodiment 20, or a pharmaceutically acceptable salt thereof, wherein $R^2$ is H.

22. The compound of any one of embodiments 19-21, or a pharmaceutically acceptable salt thereof, wherein $R^4$ is halogen.

23. The compound of any one of embodiments 1-22, or a pharmaceutically acceptable salt thereof, wherein $R^1$ is H.

24. The compound of any one of embodiments 1-22, or a pharmaceutically acceptable salt thereof, wherein $R^1$ is selected from the group consisting of unsubstituted $C_{1-6}$ alkyl and substituted $C_{1-6}$ alkyl.

25. The compound of any one of embodiments 1-22, or a pharmaceutically acceptable salt thereof, wherein $R^1$ is selected from the group consisting of —($C_{1-6}$ alkylene)-OC(O)—($C_{1-6}$ alkyl) and —($C_{1-6}$ alkylene)-OC(O)—($C_{1-6}$ alkoxy).

26. The compound of embodiment 25, or a pharmaceutically acceptable salt thereof, wherein $R^1$ is —($C_{1-6}$ alkylene)-OC(O)—($C_{1-6}$ alkoxy).

27. The compound of embodiment 1, which is a triazole as described herein, a tautomer thereof, or a pharmaceutically acceptable salt thereof.

28. A pharmaceutical composition comprising a compound according to any one of embodiments 1-27, or a pharmaceutically acceptable salt thereof, and a pharmaceutically acceptable excipient.

29. A method for treating primary hyperoxaluria, type I (PH1) comprising administering to a subject in need thereof a therapeutically effective amount of a compound according to any one of embodiments 1-27, or a pharmaceutically acceptable salt thereof, or a pharmaceutical composition according to embodiment 28.

30. A method for treating kidney stones comprising administering to a subject in need thereof a therapeutically effective amount of a compound according to any one of embodiments 1-27, or a pharmaceutically acceptable salt thereof, or a pharmaceutical composition according to embodiment 28.

31. A method for treating primary hyperoxaluria, type I (PH1) comprising administering to a subject in need thereof a therapeutically effective amount of a compound according to Formula II:

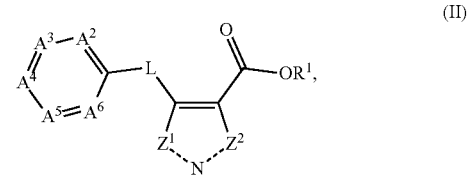

(II)

or a pharmaceutically acceptable salt thereof, wherein:
L is selected from the group consisting of O and S;
$A^2$ is selected from the group consisting of $CR^2$ and N;
$A^3$ is selected from the group consisting of $CR^3$ and N;
$A^4$ is selected from the group consisting of $CR^4$ and N;
$A^5$ and $A^6$ are independently selected from the group consisting of CH and N;
the dashed line connected to $Z^1$ is a double bond, $Z^1$ is N, the dashed line connected to $Z^2$ is a single bond, and $Z^2$ is $NR^8$; or
the dashed line connected to $Z^1$ is a single bond, $Z^1$ is $NR^8$, the dashed line connected to $Z^2$ is a double bond, and $Z^2$ is N;

$R^1$ is selected from the group consisting of H, unsubstituted $C_{1-6}$ alkyl, substituted $C_{1-6}$ alkyl, —($C_{1-6}$ alkylene)-OC(O)—($C_{1-6}$ alkyl), and —($C_{1-6}$ alkylene)-OC(O)—($C_{1-6}$ alkoxy);

$R^2$ is selected from the group consisting of H and halogen;

$R^3$ and $R^4$ are independently selected from the group consisting of H, halogen, $C_{1-12}$ alkyl, $C_{1-12}$ alkoxy, $C_{6-12}$ aryl, $C_{3-8}$ cycloalkyl, 3- to 12-membered heterocyclyl, and 5- to 12-membered heteroaryl;

$R^3$ is optionally substituted with one or more $R^{3a}$; and
$R^4$ is optionally substituted with one or more $R^{4a}$; and each $R^{3a}$ and $R^{4a}$ is independently selected from the group consisting of $C_{1-12}$ alkyl, $C_{1-12}$ alkoxy, $C_{1-12}$ haloalkyl, $C_{1-12}$ haloalkoxy, halogen, —OH, —$CO_2$H, —$SO_3$, —CN, —$NO_2$, —$N_3$, $C_{2-12}$ alkenyl, $C_{2-12}$ alkynyl, $C_{3-8}$ cycloalkyl, $C_{3-8}$ halocycloalkyl, ($C_{6-12}$ aryl)-M-, 3- to 12-membered heterocyclyl, 5- to 12-membered heteroaryl, —N($R^a$)$_2$, —C(O)N($R^a$)$_2$, —OC(O)N($R^a$)$_2$, —S(O)$_2$N($R^a$)$_2$, —$NR^a$C(O)$R^b$, —C(O)$R^b$, and —OC(O)$R^b$;

$R^5$ is selected from the group consisting of H, unsubstituted $C_{1-6}$ alkyl, substituted $C_{1-6}$ alkyl, $C_{2-7}$ acyl, —($C_{1-6}$ alkylene)-OC(O)—($C_{1-6}$ alkyl), and —($C_{1-6}$ alkylene)-OC(O)—($C_{1-6}$ alkoxy);

each M is independently selected from a covalent bond, $NR^a$, O, S, $C_{1-6}$ alkylene, and 2- to 6-membered heteroalkylene;

each $R^a$ is independently selected from the group consisting of H and $C_{1-6}$ alkyl; and each $R^b$ is independently selected from the group consisting of $C_{1-6}$ alkyl and $C_{1-6}$ alkoxy;

provided that if L is S, $A^2$ is $CR^2$, $A^3$ is $CR^3$, $A^4$ is $CR^4$, and $A^5$ and $A^6$ are CH, then:

$R^4$ is other than methoxy, 4-bromophenyl, or 4-fluorophenyl when $R^2$ and $R^3$ are H, and $R^3$ is other than 4-bromophenyl or 4-fluorophenyl when $R^2$ and $R^4$ are H.

32. A method for treating kidney stones comprising administering to a subject in need thereof a therapeutically effective amount of a compound according to Formula II:

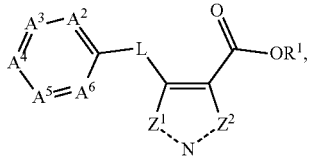

(II)

or a pharmaceutically acceptable salt thereof, wherein:

L is selected from the group consisting of O and S;

$A^2$ is selected from the group consisting of $CR^2$ and N;
$A^3$ is selected from the group consisting of $CR^3$ and N;
$A^4$ is selected from the group consisting of $CR^4$ and N;
$A^5$ and $A^6$ are independently selected from the group consisting of CH and N;

the dashed line connected to $Z^1$ is a double bond, $Z^1$ is N, the dashed line connected to $Z^2$ is a single bond, and $Z^2$ is $NR^5$; or the dashed line connected to $Z^1$ is a single bond, $Z^1$ is $NR^5$, the dashed line connected to $Z^2$ is a double bond, and $Z^2$ is N;

$R^1$ is selected from the group consisting of H, unsubstituted $C_{1-6}$ alkyl, substituted $C_{1-6}$ alkyl, —($C_{1-6}$ alkylene)-OC(O)—($C_{1-6}$ alkyl), and —($C_{1-6}$ alkylene)-OC(O)—($C_{1-6}$ alkoxy);

$R^2$ is selected from the group consisting of H and halogen;

$R^3$ and $R^4$ are independently selected from the group consisting of H, halogen, $C_{1-12}$ alkyl, $C_{1-12}$ alkoxy, $C_{6-12}$ aryl, $C_{3-8}$ cycloalkyl, 3- to 12-membered heterocyclyl, and 5- to 12-membered heteroaryl;

$R^3$ is optionally substituted with one or more $R^{3a}$; and
$R^4$ is optionally substituted with one or more $R^{4a}$; and each $R^{3a}$ and $R^{4a}$ is independently selected from the group consisting of $C_{1-12}$ alkyl, $C_{1-12}$ alkoxy, $C_{1-12}$ haloalkyl, $C_{1-12}$ haloalkoxy, halogen, —OH, —$CO_2$H, —$SO_3$, —CN, —$NO_2$, —$N_3$, $C_{2-12}$ alkenyl, $C_{2-12}$ alkynyl, $C_{3-8}$ cycloalkyl, $C_{3-8}$ halocycloalkyl, ($C_{6-12}$ aryl)-M-, 3- to 12-membered heterocyclyl, 5- to 12-membered heteroaryl, —N($R^a$)$_2$, —C(O)N($R^a$)$_2$, —OC(O)N($R^a$)$_2$, —S(O)$_2$N($R^a$)$_2$, —$NR^a$C(O)$R^b$, —C(O)$R^b$, and —OC(O)$R^b$;

$R^5$ is selected from the group consisting of H, unsubstituted $C_{1-6}$ alkyl, substituted $C_{1-6}$ alkyl, $C_{2-7}$ acyl, —($C_{1-6}$ alkylene)-OC(O)—($C_{1-6}$ alkyl), and —($C_{1-6}$ alkylene)-OC(O)—($C_{1-6}$ alkoxy);

each M is independently selected from a covalent bond, $NR^a$, O, S, $C_{1-6}$ alkylene, and 2- to 6-membered heteroalkylene;

each $R^a$ is independently selected from the group consisting of H and $C_{1-6}$ alkyl; and each $R^b$ is independently selected from the group consisting of $C_{1-6}$ alkyl and $C_{1-6}$ alkoxy;

provided that if L is S, $A^2$ is $CR^2$, $A^3$ is $CR^3$, $A^4$ is $CR^4$, and $A^5$ and $A^6$ are CH, then:

$R^4$ is other than methoxy, 4-bromophenyl, or 4-fluorophenyl when $R^2$ and $R^3$ are H, and $R^3$ is other than 4-bromophenyl or 4-fluorophenyl when $R^2$ and $R^4$ are H.

33. The method of embodiment 31 or embodiment 32, wherein $R^2$ and $R^3$ are independently selected from the group consisting of H and halogen 34. The method of any one of embodiments 31-33, wherein L is O.

35. The method of embodiment 31 or embodiment 32, wherein the compound is a triazole compound as described herein, a tautomer thereof, or a pharmaceutically acceptable salt thereof.

36. A method for inhibiting glycolate oxidase comprising contacting glycolate oxidase with an effective amount of a compound as recited in any one of embodiments 1-27 and 32-35.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound according to Formula I:

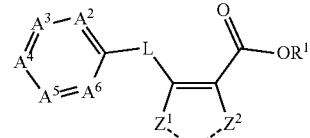

(I)

or a pharmaceutically acceptable salt thereof, wherein:

L is selected from the group consisting of O and S;

$A^2$ is selected from the group consisting of $CR^2$ and N;

$A^3$ is selected from the group consisting of $CR^3$ and N;

$A^4$ is selected from the group consisting of $CR^4$ and N;

$A^5$ and $A^6$ are independently selected from the group consisting of CH and N;

the dashed line connected to $Z^1$ is a single bond, $Z^1$ is $NR^5$, the dashed line connected to $Z^2$ is a double bond, and $Z^2$ is N, or the dashed line connected to $Z^1$ is a double bond, $Z^1$ is N, the dashed line connected to $Z^2$ is a single bond, and $Z^2$ is $NR^5$;

$R^1$ is selected from H, unsubstituted $C_{1-6}$ alkyl, substituted $C_{1-6}$ alkyl, —($C_{1-6}$ alkylene)-OC(O)—($C_{1-6}$ alkyl), and —($C_{1-6}$ alkylene)-OC(O)—($C_{1-6}$ alkoxy);

$R^2$ is selected from the group consisting of H and halogen;

$R^3$ is selected from the group consisting of H, halogen, $C_{1-12}$ alkyl, $C_{1-12}$ alkoxy, $C_{6-12}$ aryl, $C_{3-8}$ cycloalkyl, 3- to 12-membered heterocyclyl, and 5- to 12-membered heteroaryl;

$R^3$ is unsubstituted, or $R^3$ is substituted with one or more $R^{3a}$;

each $R^{3a}$ is independently selected from the group consisting of $C_{1-12}$ alkyl, $C_{1-12}$ alkoxy, $C_{1-12}$ haloalkyl, $C_{1-12}$ haloalkoxy, halogen, —OH, —$CO_2$H, —$SO_3$, —CN, —$NO_2$, —$N_3$, $C_{2-12}$ alkenyl, $C_{2-12}$ alkynyl, $C_{3-8}$ cycloalkyl, $C_{3-8}$ halocycloalkyl, ($C_{6-12}$ aryl)-M-, 3- to 12-membered heterocyclyl, 5- to 12-membered heteroaryl, —N($R^a$)$_2$, —C(O)N($R^a$)$_2$, —OC(O)N($R^a$)$_2$, —S(O)$_2$N($R^a$)$_2$, —$NR^a$C(O)$R^b$, —C(O)$R^b$, and —OC(O)$R^b$;

$R^4$ is selected from the group consisting of $C_{6-12}$ aryl and 5- to 12-membered heteroaryl;

$R^4$ is substituted with one or more $R^{4a}$;

each $R^{4a}$ is independently $C_{3-8}$ halocycloalkyl;

$R^5$ is selected from the group consisting of H, unsubstituted $C_{1-6}$ alkyl, substituted $C_{1-6}$ alkyl, $C_{2-7}$ acyl, —($C_{1-6}$ alkylene)-OC(O)—($C_{1-6}$ alkyl), and —($C_{1-6}$ alkylene)-OC(O)—($C_{1-6}$ alkoxy);

each M is independently selected from the group consisting of a covalent bond, $NR^a$, O, S, $C_{1-6}$ alkylene, and 2- to 6-membered heteroalkylene;

each $R^a$ is independently selected from the group consisting of H and $C_{1-6}$ alkyl; and each $R^b$ is independently selected from the group consisting of $C_{1-6}$ alkyl and $C_{1-6}$ alkoxy.

2. The compound of claim 1, or a pharmaceutically acceptable salt thereof, wherein the dashed line connected to $Z^1$ is a single bond, $Z^1$ is $NR^5$, the dashed line connected to $Z^2$ is a double bond, and $Z^2$ is N.

3. The compound of claim 1, or a pharmaceutically acceptable salt thereof, wherein the dashed line connected to $Z^1$ is a double bond, $Z^1$ is N, the dashed line connected to $Z^2$ is a single bond, and $Z^2$ is $NR^5$.

4. The compound of claim 1, or a pharmaceutically acceptable salt thereof, wherein $R^5$ is H.

5. The compound of claim 1, or a pharmaceutically acceptable salt thereof, having a structure according to Formula Ia:

6. The compound of claim 5, or a pharmaceutically acceptable salt thereof, wherein L is O.

7. The compound of claim 6, or a pharmaceutically acceptable salt thereof, wherein $R^2$ and $R^3$ are H.

8. The compound of claim 6, or a pharmaceutically acceptable salt thereof, wherein $R^4$ is selected from the group consisting of phenyl and biphenyl, each of which is substituted with $C_{3-8}$ halocycloalkyl.

9. The compound of claim 1, or a pharmaceutically acceptable salt thereof, wherein $R^2$ and $R^3$ are H.

10. The compound of claim 1, or a pharmaceutically acceptable salt thereof, wherein $R^4$ is selected from the group consisting of phenyl and biphenyl, each of which is substituted with $C_{3-8}$ halocycloalkyl.

11. The compound of claim 5, or a pharmaceutically acceptable salt thereof, wherein L is S.

12. The compound of claim 1, or a pharmaceutically acceptable salt thereof, wherein $R^1$ is H.

13. The compound of claim 1, or a pharmaceutically acceptable salt thereof, wherein $R^1$ is selected from the group consisting of unsubstituted $C_{1-6}$ alkyl and substituted $C_{1-6}$ alkyl.

14. The compound of claim 1, or a pharmaceutically acceptable salt thereof, wherein $R^1$ is selected from the group consisting of —($C_{1-6}$ alkylene)-OC(O)—($C_{1-6}$ alkyl) and —($C_{1-6}$ alkylene)-OC(O)—($C_{1-6}$ alkoxy).

15. The compound of claim 1, which is selected from the group consisting of tautomers thereof, and pharmaceutically acceptable salts thereof.

16. The compound of claim 8, or a pharmaceutically acceptable salt thereof, wherein $R^4$ is phenyl, substituted with $C_{3-8}$ halocycloalkyl.

17. The compound of claim 10, or a pharmaceutically acceptable salt thereof, wherein $R^4$ is phenyl, substituted with $C_{3-8}$ halocycloalkyl.

18. The compound of claim 15, represented by the formula:

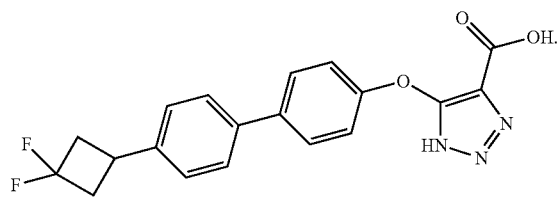 [SMILES: O=C(O)c1nn[nH]c1Oc1ccc(-c2ccc(C3CC(F)(F)C3)cc2)cc1]

19. A pharmaceutical composition comprising a compound according to claim 1, or a pharmaceutically acceptable salt thereof, and a pharmaceutically acceptable excipient.

20. A method for treating primary hyperoxaluria type I (PH1) comprising administering to a subject in need thereof a therapeutically effective amount of a compound according to claim 1.

21. A method for treating kidney stones comprising administering to a subject in need thereof a therapeutically effective amount of a compound according to claim 1.

22. The method of claim 20, wherein the compound is represented by the formula:

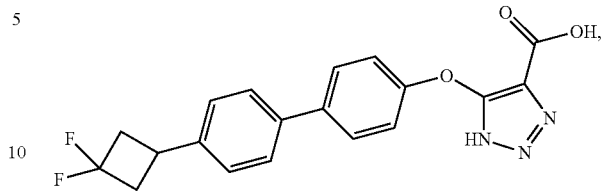

or a tautomer thereof, and/or a pharmaceutically acceptable salt thereof.

23. The method of claim 21, wherein the compound is represented by the formula:

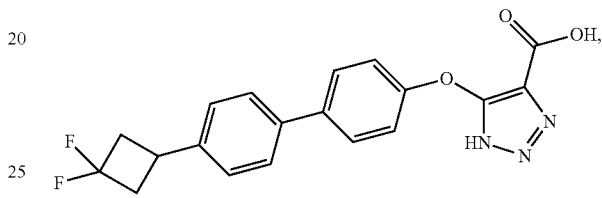

or a tautomer thereof, and/or a pharmaceutically acceptable salt thereof.

* * * * *